(12) United States Patent
Machhammer et al.

(10) Patent No.: US 7,897,812 B2
(45) Date of Patent: Mar. 1, 2011

(54) PROCESS FOR PREPARING ACROLEIN OR ACRYLIC ACID OR A MIXTURE THEREOF FROM PROPANE

(75) Inventors: Otto Machhammer, Mannheim (DE); Klaus Joachim Mueller-Engel, Stutensee (DE); Martin Dieterle, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 416 days.

(21) Appl. No.: 11/751,202

(22) Filed: May 21, 2007

(65) Prior Publication Data

US 2007/0276157 A1  Nov. 29, 2007

Related U.S. Application Data

(60) Provisional application No. 60/802,786, filed on May 24, 2006.

(30) Foreign Application Priority Data

May 24, 2006 (DE) ........................ 10 2006 024 901

(51) Int. Cl.
*C07C 51/16* (2006.01)
*C07B 41/00* (2006.01)
(52) U.S. Cl. .................................... 562/545; 568/469.9
(58) Field of Classification Search ........................ None
See application file for complete search history.

(56) References Cited

U.S. PATENT DOCUMENTS

| | | | |
|---|---|---|---|
| 3,161,670 A | 12/1964 | Adams | |
| 5,705,684 A * | 1/1998 | Hefner et al. | 562/545 |
| 6,166,263 A | 12/2000 | Etzkorn et al. | |
| 6,187,963 B1 | 2/2001 | Etzkorn et al. | |
| 6,781,017 B2 * | 8/2004 | Machhammer et al. | 568/470 |
| 7,238,827 B2 | 7/2007 | Hechler et al. | |
| 7,291,761 B2 | 11/2007 | Machhammer et al. | |
| 7,321,058 B2 | 1/2008 | Machhammer et al. | |
| 7,348,443 B2 | 3/2008 | Proll et al. | |
| 2004/0199001 A1 | 10/2004 | Schindler et al. | |
| 2006/0004226 A1 | 1/2006 | Machhammer et al. | |
| 2006/0004227 A1 | 1/2006 | Dieterle et al. | |
| 2006/0004229 A1 * | 1/2006 | Dieterle et al. | 562/527 |
| 2006/0258529 A1 | 11/2006 | Diefenbacher et al. | |
| 2007/0088092 A1 | 4/2007 | Klanner et al. | |
| 2007/0117998 A1 | 5/2007 | Machhammer et al. | |
| 2007/0123732 A1 | 5/2007 | Dieterle et al. | |
| 2007/0142689 A1 | 6/2007 | Hechler et al. | |
| 2008/0119673 A1 | 5/2008 | Hechler et al. | |

FOREIGN PATENT DOCUMENTS

| | | |
|---|---|---|
| DE | 33 13 573 A1 | 10/1983 |
| DE | 102 45 585 A1 | 4/2004 |
| DE | 103 16 039 A1 | 10/2004 |
| DE | 10 2004 032 129 A1 | 3/2005 |
| DE | 10 2005 009 885 A1 | 9/2006 |
| DE | 10 2005 009 891 A1 | 9/2006 |
| DE | 10 2005 010 111 A1 | 9/2006 |
| DE | 10 2005 013 039 A1 | 9/2006 |
| DE | 10 2005 022 798 A1 | 11/2006 |
| DE | 10 2005 049 699 A1 | 4/2007 |
| DE | 10 2005 052 923 A1 | 5/2007 |
| DE | 10 2005 056 377 A1 | 5/2007 |
| DE | 10 2005 061 626 A1 | 6/2007 |
| DE | 10 2006 015 235 A1 | 10/2007 |
| EP | 0 117 146 A1 | 8/1984 |
| EP | 0 731 077 A2 | 9/1996 |
| EP | 1 617 931 | 1/2006 |
| WO | WO 01/96270 A2 | 12/2001 |
| WO | WO 01/96271 A2 | 12/2001 |
| WO | WO 03/011804 A2 | 2/2003 |
| WO | WO 03/076370 A1 | 9/2003 |
| WO | WO 2004/078321 A1 | 9/2004 |

* cited by examiner

*Primary Examiner*—Karl J Puttlitz
(74) *Attorney, Agent, or Firm*—Oblon, Spivak, McClelland, Maier & Neustadt, L.L.P.

(57) ABSTRACT

A process for preparing acrolein or acrylic acid or a mixture thereof as the target product from propane, in which propane is partially dehydrogenated under heterogeneous catalysis in a reaction zone A, molecular hydrogen formed is at least partly combusted to water, any water present in the product gas A formed in reaction zone A is removed therefrom and product gas A is otherwise used to charge a reaction zone B in which propylene formed in reaction zone A is partially oxidized in the presence of remaining propane to give the target product. The target product is removed from the product gas B formed in reaction zone B and propane present in the remaining residual gas is absorbed therefrom into a solvent and, after release from the absorbate, recycled into reaction zone A.

37 Claims, No Drawings

PROCESS FOR PREPARING ACROLEIN OR ACRYLIC ACID OR A MIXTURE THEREOF FROM PROPANE

The present invention relates to a process for preparing acrolein or acrylic acid or a mixture thereof from propane, in which A) at least two gaseous propane-comprising feed streams, of which at least one comprises fresh propane, are fed to a first reaction zone A to form a reaction gas A;
in reaction zone A, reaction gas A is conducted through at least one catalyst bed in which partial heterogeneously catalyzed dehydrogenation of the propane forms molecular hydrogen and propylene;
molecular oxygen is fed to reaction zone A and, in reaction zone A, oxidizes at least a portion of molecular hydrogen present in reaction gas A to steam, and product gas A which comprises propylene, propane and steam is withdrawn from reaction zone A;

B) in a first separation zone I, steam present in product gas A is optionally removed by condensation partly or fully by indirect and/or direct cooling of product gas A to leave a product gas A*;

C) in a reaction zone B, product gas A or product gas A* is used, with feeding of molecular oxygen, to charge at least one oxidation reactor with a reaction gas B comprising propane, propylene and molecular oxygen, and the propylene present therein is subjected to a heterogeneously catalyzed partial gas phase oxidation to give acrolein or acrylic acid or a mixture thereof as the target product, and also product gas B comprising unconverted propane;

D) product gas B is conducted out of reaction zone B and, in a second separation zone II, target product present therein is removed to leave a propane-comprising residual gas;

E) a portion of residual gas having the composition of the residual gas is optionally recycled as a propane-comprising feed stream into reaction zone A;

F) in a separation zone III, propane present in residual gas, which has not been recycled into reaction zone A and from which steam present therein optionally has been removed beforehand partly or fully by condensation and/or any molecular hydrogen present therein optionally has been removed beforehand partly or fully by means of a separating membrane is absorbed into an organic solvent by absorption from the residual gas to form a propane-comprising absorbate; and G) in a separation zone IV, the propane is removed from the absorbate and recycled into reaction zone A as a propane-comprising feed stream.

Acrylic acid is an important commodity chemical which finds use, inter alia, as a monomer for preparing polymers which are used, for example, in disperse distribution in aqueous medium, as binders. A further field of use of acrylic acid polymers is that of superabsorbents in the hygiene sector and other fields of use. Acrolein is an important intermediate, for example for the preparation of glutaraldehyde, methionine, 1,3-propanediol, 3-picoline, folic acid and acrylic acid (cf., for example, U.S. Pat. Nos. 6,166,263 and 6,187,963).

Processes for preparing acrolein or acrylic acid or a mixture thereof from propane, in which, in a first reaction zone, propane is dehydrogenated partially to propylene under heterogeneous catalysis and the propylene formed is then partially oxidized in the presence of the unconverted propane (i.e. without removing the propylene from the propane remaining in the dehydrogenation beforehand, as recommended, for example, in EP-A 1 617 931 (cf. also WO 04/09041)) under heterogeneous catalysis to give acrolein or to give acrylic acid or to give a mixture thereof, are known (cf., for example, DE-A 33 13 573, EP-A 117 146, U.S. Pat. No. 3,161,670, DE-A 10 2004 032 129, EP-A 731 077, DE-A 10 2005 049 699, DE-A 10 2005 052 923, WO 01/96271, WO 03/011804, WO 03/076370, WO 01/96270, DE-A 10 2005 009 891, DE-A 10 2005 013 039, DE-A 10 2005 022 798, DE-A 10 2005 009 885, DE-A 10 2005 010 111, DE-A 102 455 85, DE-A 103 160 39, DE 10 2005 056377.5, DE 10 2005 049699.7, DE 10 2006 015235.2, DE 10 2005 061626.7 and the prior art cited in these documents).

A common feature of the processes described there is that, after the removal of the target product acrolein or acrylic acid or acrolein and acrylic acid from the product gas mixture of the propylene partial oxidation, at least a portion of the propane present in the residual gas from the remaining propane-comprising residual gas is recycled as cycle gas into the heterogeneously catalyzed partial dehydrogenation of propane to propylene.

Otherwise, the above prior art processes can be divided essentially into two groups. The processes of one of the two groups are characterized in that the constituents other than propane and propylene are removed by absorption from the product gas mixture of the heterogeneously catalyzed partial dehydrogenation before the propylene is subjected in the presence of the remaining propane to the partial oxidation to the desired target product (DE 10 2005 013039.9). A disadvantage of this procedure is that it generally requires at least three zones in which gas has to be compressed. Firstly, it typically requires compression of the product gas of the heterogeneously catalyzed partial dehydrogenation of the propane before it is subjected to the absorptive removal of the propylene and propane present therein, since an absorptive removal can normally be performed efficiently only under pressure. In addition, it generally requires compression of the oxygen source used for the heterogeneously catalyzed partial oxidation and, furthermore, it normally requires compression of the propane which remains in the heterogeneously catalyzed partial oxidation of the propylene and is recycled into the heterogeneously catalyzed partial dehydrogenation. The processes of the other of the two groups are characterized in that they recommend the use of the product gas mixture of the heterogeneously catalyzed partial dehydrogenation as such to charge the heterogeneously catalyzed propylene partial oxidation (cf., for example, DE-A 103 160 39). The basis of this procedure is, inter alia, the assumption that the molecular hydrogen formed in the heterogeneously catalyzed partial dehydrogenation of the propane does not have an adverse effect in the heterogeneously catalyzed partial oxidation of the propylene which follows (in contrast to the exothermic heterogeneously catalyzed oxydehydrogenation, which is forced by the presence of oxygen and in which free hydrogen is neither formed as an intermediate (the hydrogen pulled from the hydrocarbon to be dehydrogenated is pulled out directly as water ($H_2O$)) nor is detectable, the heterogeneously catalyzed dehydrogenation (for example that to be performed in reaction zone A) will be understood in this application to mean a ("conventional") dehydrogenation whose thermal character, in contrast to the oxydehydrogenation, is endothermic (an exothermic hydrogen combustion may be included in reaction zone A as a subsequent step) and in which free molecular hydrogen is formed at least as an intermediate; this generally requires different reaction conditions and different catalysts than for the oxydehydrogenation; in other words, the heterogeneously catalyzed partial dehydrogenation of the propane in reaction zone A in the process according to the invention proceeds necessarily with evolution of $H_2$). However, in-house investigations have shown that presence of increased amounts of molecular hydrogen in the reaction gas mixture for the heterogeneously catalyzed partial oxidation of propylene, while not having a significant effect on the by-product spectrum of the partial oxidation, do (presumably owing to the marked reduction potential of the molecular hydrogen) noticeably impair the lifetime of the catalysts to be used for the heterogeneously catalyzed partial gas phase oxidation.

In addition, molecular hydrogen burdens reaction gas B with a potentially explosive constituent having a specific diffusion behavior (certain construction materials are permeable to molecular hydrogen). Inseparably linked with the above-described problems is the use of an excess of molecular oxygen, which is advantageous for an increased catalyst lifetime in the partial oxidation of reaction zone B, relative to the target reaction stoichiometry, which of course brings increased explosion risks in the presence of molecular hydrogen in reaction zone B (when acrylic acid is the target product and the total amount of molecular oxygen required is added beforehand to reaction gas B, a molar ratio of molecular oxygen present in reaction gas B to propylene present therein of at least >1.5 is normally required (this already takes into account a low degree of full propylene combustion)).

In view of the prior art described, it was an object of the present invention to provide an improved process according to the preamble of the present document which has the disadvantages described in reduced form at worst.

Accordingly, a process has been found for preparing acrolein or acrylic acid or a mixture thereof from propane, in which A) at least two gaseous propane-comprising feed streams, of which at least one comprises fresh propane, are fed to a first reaction zone A to form a reaction gas A;
 in reaction zone A, reaction gas A is conducted through at least one fixed catalyst bed in which partial heterogeneously catalyzed dehydrogenation of the propane forms molecular hydrogen and propylene;
 molecular oxygen is fed to reaction zone A and, in reaction zone A, oxidizes at least a portion of molecular hydrogen present in reaction gas A to steam, and
 product gas A which comprises propylene, propane and steam is withdrawn from reaction zone A;

B) in a first separation zone I, steam present in product gas A is optionally removed by condensation partly or fully by indirect and/or direct cooling of product gas A to leave a product gas A*;

C) in a reaction zone B, product gas A or product gas A* is used, with feeding of molecular oxygen, to charge at least one oxidation reactor with a reaction gas B comprising propane, propylene and molecular oxygen, and the propylene present therein is subjected to a heterogeneously catalyzed partial gas phase oxidation to give acrolein or acrylic acid or a mixture thereof as the target product, and also product gas B comprising unconverted propane;

D) product gas B is conducted out of reaction zone B and, in a second separation zone II, target product present therein is removed to leave a propane-comprising residual gas;

E) a portion of residual gas having the composition of the residual gas is optionally recycled as a propane-comprising feed stream into reaction zone A (residual gas cycle gas);

F) in a separation zone III, propane present in residual gas which has not been recycled into reaction zone A and from which steam present therein optionally has been removed beforehand partly or fully by condensation and/or any molecular hydrogen present therein optionally has been removed beforehand partly or fully by means of a separating membrane is absorbed into an organic solvent by absorption from the residual gas to form a propane-comprising absorbate; and G) in a separation zone IV, the propane is removed from the absorbate and recycled into reaction zone A as a propane-comprising feed stream (propane cycle gas which preferably comprises steam);

which comprises oxidizing at least sufficient molecular hydrogen to steam in reaction zone A that the amount of hydrogen oxidized to steam in reaction zone A is at least 20 mol% of the amount of molecular hydrogen formed in reaction zone A.

Advantageously in accordance with the invention, at least some of the heat energy generated by the oxidation (combustion) of molecular hydrogen in reaction zone A will also be used, by indirect heat exchange with reaction gas A and/or product gas A as a heat carrier, to heat (the) constituents of the reaction gas A charge gas mixture (of the gaseous feed streams fed to reaction zone A).

Advantageously in accordance with the invention, the amount of hydrogen oxidized to steam in reaction zone A is at least 25 mol %, better at least 30 mol %, preferably at least 35 mol %, more preferably at least 40 mol %, even better at least 45 mol % and most preferably at least 50 mol %, based in each case on the amount of molecular hydrogen formed in reaction zone A.

In other words, processes according to the invention are also those in which, in reaction zone A, based on the amount of molecular hydrogen formed in reaction zone A, up to 55 mol %, or up to 60 mol %, or up to 65 mol %, or up to 70 mol %, or up to 75 mol %, or up to 80 mol %, or up to 85 mol %, or up to 90 mol %, or up to 95 mol %, or up to 100 mol % of molecular hydrogen is oxidized to steam.

When the fact that the combustion (oxidation) of molecular hydrogen to water affords about twice that amount of heat which is consumed for its formation in the course of the dehydrogenation of propane is taken into account in addition to the effect of molecular hydrogen as a constituent of reaction gas B on the catalyst lifetime in the partial oxidation, it is advantageous in terms of heat budget when the amount of molecular hydrogen combusted in reaction zone A in the process according to the invention, based on the amount of molecular hydrogen formed in reaction zone A, is from 30 to 70 mol %, better from 40 to 60 mol %.

A restricted content of molecular hydrogen in reaction gas B (i.e. a reaction gas B which still comprises molecular hydrogen) is also advantageous to a certain degree in that molecular hydrogen has the advantage of the highest thermal conductivity among the gases. According to Walter J. Moore, Physikalische Chemie [Physical chemistry], WDEG Verlag, Berlin (1973), page 171, the thermal conductivity under standard conditions is, for example, more than ten times as large as the thermal conductivity of carbon dioxide and about eight times as large as that of molecular nitrogen or of molecular oxygen.

It is this increased thermal conductivity which, according to Table I of DE-A 33 13 573, is responsible for the selectivity of $CO_x$ formation in the presence of molecular hydrogen in reaction zone B being significantly lower than in the absence of molecular hydrogen. Owing to more rapid heat removal from the reaction site in reaction zone B, it causes lower catalyst surface temperatures and accordingly a lower proportion of propylene full combustion. This is especially true when, as in the process according to the invention, molecular hydrogen which has the highest thermal conductivity and propane which has the highest thermal absorbency are involved synergistically together in the heat removal.

In principle, reaction gas B in the process according to the invention may, however, also no longer comprise any molecular hydrogen.

In principle, the product gas A which comprises propylene, propane and steam and is withdrawn from reaction zone A can be used as such to charge the at least one oxidation reactor in reaction zone B. However, it is advantageous in accordance with the invention to condense out at least a portion of the steam present in product gas A in a first separation zone I by direct and/or indirect cooling of product gas A and thus to remove it from product gas A to leave a product gas A* whose content of steam is lower than that of product gas A.

One reason for this is that the acrolein and/or acrylic acid target products have a significantly higher affinity for water than the constituents of product gas A, which is why target product removal from a product gas B comprising elevated amounts of steam is associated with a significant energy demand. Secondly, elevated amounts of steam in reaction gas B typically reduce the lifetime of the catalysts which generally comprise Mo in oxidic form and are used for the partial oxidation, since $H_2O$ promotes the sublimation of molybdenum oxides. In addition, steam removed between reaction zone A and reaction zone B reduces the total volume of reaction gas B and hence the energy demand to be expended to convey it through reaction zone B.

Advantageously, at least 5 mol %, better at least 10 mol %, even better at least 15 mol %, particularly advantageously at least 20 mol %, more advantageously at least 25 mol % or at least 30 mol %, even more advantageously at least 35 mol % or at least 40 mol %, better at least 45 mol % or at least 50 mol %, particularly advantageously at least 55 mol % or at least 60 mol %, preferably at least 65 mol % or at least 70 mol %, more preferably at least 75 mol % or at least 80 mol %, even more preferably at least 85 mol % or at least 90 mol %, in many cases at least 95 mol % or in the extreme case up to 100 mol % (but frequently not more than 80 mol %, or not more than 85 mol %, or not more than 90 mol %, or not more than 95 mol %, or not more than 98 mol %) of the steam present in product gas A is removed by condensation in separation zone 1 in the process according to the invention. A restricted (but not vanishing) steam content in reaction gas B is favorable in that it normally has an advantageous effect on the activity of the catalysts used for reaction zone B (especially in the case of multimetal oxides).

It is favorable for the process according to the invention that the removal of the water between reaction zone A and reaction zone B can be achieved by simple condensation.

Water removed between reaction zone A and reaction zone B may not only be water formed by the hydrogen oxidation in reaction zone A. Instead, steam may additionally also have been used as an inert diluent gas in reaction zone A and is, if appropriate, equally removed partly or fully in separation zone I.

Owing to the comparatively high boiling point of water, especially at elevated pressures, the aforementioned condensation can normally be achieved by simple direct and/or indirect cooling of product gas A. In principle, the condensation can be brought about by single-stage or multistage cooling. Appropriately in accordance with the invention, the condensative removal of the water will be brought about by multistage cooling. Advantageously from an application point of view, direct and indirect cooling will be employed in combination. Suitable indirect heat exchangers for the inventive purpose are in principle all known indirect heat exchanger types. Among these, preference is given to using tube bundle heat exchangers and plate heat exchangers. For example, in a first cooling stage, the product gas A withdrawn hot from reaction zone A (typical temperatures of product gas A are, for example, from 400 to 700° C., preferably from 500 to 600° C.; typical working pressures of product gas A are generally from >1 or 1.5 to 5 bar, or from 2 to 5 bar, preferably from 1.5 or 2 to 3 bar) can be conducted, in a first indirect heat exchanger (quite generally, hot product gas A withdrawn from reaction zone A can be used in the process according to the invention in order to heat at least some of the constituents or all constituents of the reaction gas A charge gas mixture (to the temperature desired in each case), and to simultaneously cool product gas A, by indirect heat exchange, if appropriate in a series of heat exchangers connected in series (for example two heat exchangers connected in series)), for example in co- or countercurrent to the gas stream which comprises propane and has been removed from the absorbate in separation zone IV (propane cycle gas), in order to bring it, as one of the propane-comprising feed streams conducted into reaction zone A, to the entrance temperature level desired for reaction zone A. This temperature level can, in a manner typical for the process according to the invention, for example, vary within the range from 400 to 600° C., preferably from 450 to 550° C. In a downstream second indirect heat exchanger, the product gas A cooled as described will appropriately be conducted, for example, in co- or in countercurrent to product gas A, from which the steam present therein has already been removed beforehand to the desired degree (in other words, it is conducted in co- or in countercurrent to product gas A*), in order to raise it again to a temperature level as is suitable and appropriate for the subsequent partial oxidation of the propylene present therein. When it leaves the second indirect heat exchanger, product gas A will generally still have a temperature above 100° C. In a third indirect heat exchanger, which is normally equipped as an air cooler (for example co- or countercurrent flow of product gas A to air), the temperature of product gas A will then be lowered to a temperature below 100° C. The removal of the steam can then be undertaken in the direct cooler which follows. The direct cooler (direct condenser) may be of a design known per se (for example it may correspond to a rectification column) and may have the customary internals (for example customary for rectification columns) for the purpose of enlarging the heat exchange surface area. In general, however, such internals will be dispensed with. Typically, the column body of the direct condenser is not insulated. Preference is given to all measures which increase the heat losses through the column wall, for example perforated sheets or cooling ribs welded on parallel to the column surface. The coolant used for the purpose of direct cooling of product gas A will advantageously be aqueous phase removed by condensation beforehand from other product gas A, which is appropriately, prior to use for direct cooling, cooled to temperatures of ≦35° C., preferably ≦30° C., in an indirect heat exchanger with the aid of cooling water (appropriately from an application point of view, surface water). In the direct cooler, product gas A and finely sprayed aqueous direct coolant can be conducted in co- or in countercurrent. In general, preference is given to cocurrent flow.

With the aid of separators known per se (for example by means of mechanical droplet separators), the aqueous phase and the remaining gaseous phase can be separated from one another. After cooling, to be performed as already described, of the removed aqueous phase, the aqueous phase can again be fed to the direct cooling of product gas A.

The temperature of the remaining gaseous phase (in the case described, it is the product gas A*) can be raised to a temperature appropriate for the subsequent partial oxidation of the propylene by subsequent indirect heat exchange (already described above) with product gas A still to be freed of steam. In principle, it is also possible in the process according to the invention for steam present in product gas A to be removed by condensation only from a portion thereof. The product gas A* thus formed can subsequently be used, as such or in a mixture with the portion of product gas A not treated by condensation (in the inventive sense, this mixture is likewise a product gas A*), to charge the heterogeneously catalyzed partial oxidation of propylene. A further advantageous effect of direct cooling of product gas A (for example with aqueous phase removed beforehand by condensation from product gas A, preferably cooled by indirect heat exchange) is generally that the direct cooling simultaneously brings about a deposition of any solid particles present in product gas A, which may, for example, be dehydrogenation catalyst particles stemming from the heterogeneously catalyzed partial dehydrogenation of propane, which, according to the teaching of DE-A 103 160 39, can have a troublesome effect in the subsequent heterogeneously catalyzed partial oxidation of propylene. This is especially true when the product gas A or product gas A* used to charge the partial oxidation still comprises molecular hydrogen. In other words, appropriately in accordance with the invention, a mechanical separating operation according to DE-A 103 160 39 is quite generally connected between reaction zone A and reaction zone B, even if only in the form of a direct cooling of reaction gas A to be performed as described.

The condensative removal of steam from product gas A in separation zone I is very particularly advantageous when it comprises a direct cooling of product gas A with aqueous phase preferably removed beforehand from product gas A and cooled (preferably by indirect heat exchange).

The aqueous phase removed by condensation as described will generally still comprise dissolved propane which can be recovered in a simple manner, for example, by heating the aqueous phase (if appropriate under reduced pressure) and can be recycled into reaction zone A as a further propane-comprising feed stream. The direct and/or indirect cooling of product gas A for the purpose of condensative removal of water present in product gas A is generally associated with a pressure drop therein of $\leq 1$ bar, usually $\leq 0.5$ bar, preferably $\leq 0.3$ bar.

The oxidation of molecular hydrogen to water in reaction zone A can be performed after the actual heterogeneously catalyzed partial dehydrogenation of propane and/or in the course of the heterogeneously catalyzed partial dehydrogenation of propane, for example when certain partial conversion values have been attained, based on the conversion of propane which arises in single pass of reaction gas A through reaction zone A. Advantageously in accordance with the invention, at least a portion of the hydrogen oxidized to water in reaction zone A is already oxidized to water before the target conversion desired (and end conversion attained) of propane in reaction zone A (based on single pass of reaction gas A through reaction zone A) has been attained.

This procedure is advantageous firstly in that it, by withdrawing molecular hydrogen from the equilibrium of the heterogeneously catalyzed dehydrogenation, shifts the equilibrium position toward the desired propylene formation. However, it is also additionally favorable in that the heat of reaction obtained in the hydrogen oxidation compensates again for the heat of reaction consumed in the dehydrogenation effected beforehand, and can provide heat of reaction for the subsequent further dehydrogenation. Advantageously in accordance with the invention, molecular hydrogen (at least in a portion) will be combusted with molecular oxygen in reaction zone A no later than when 90 mol %, better when 75 mol % of the total amount of molecular hydrogen formed in reaction zone A has been formed. Preferably in accordance with the invention, molecular hydrogen (at least in a portion) will be combusted with molecular oxygen in reaction zone A no later than when 65 mol %, or 55 mol %, or 45 mol % of the total amount of molecular hydrogen formed in reaction zone A has been formed.

The time at which molecular hydrogen is combusted in reaction zone A can be influenced firstly by where (when) molecular oxygen is fed into reaction zone A.

When a portion (whose composition corresponds to that of the residual gas) of the propane-comprising residual gas remaining in separation zone II is conducted as such (i.e. without passing through the separation zones III/IV) to reaction zone A, the charge gas mixture of reaction zone A may already comprise molecular oxygen, since the aforementioned residual gas generally still comprises molecular oxygen employed in excess in reaction zone B.

In addition, it can also be influenced by the configuration of the charge of reaction zone A with catalyst. Thus, reaction zone A may be charged locally with catalyst which exceptionally selectively catalyzes only the oxidation of molecular hydrogen with molecular oxygen to water. Other catalysts are capable of extremely selectively catalyzing the dehydrogenation. In general, those catalysts which are capable of catalyzing the dehydrogenation are also capable of catalyzing the hydrogen combustion, in which case they are normally capable of reducing the activation energy of the latter reaction particularly markedly.

In this document, fresh propane is understood to mean propane which has not yet taken part in a dehydrogenation in reaction zone A. In general, it is supplied as a constituent of crude propane (which preferably satisfies the specification according to DE-A 10246119 and DE-A 10245585) which also comprises small amounts of components other than propane.

Such crude propane is obtainable, for example, by processes described in DE-A 102005 022798. In general, in addition to fresh propane, the only further propane-comprising feed stream fed to reaction zone A in the process according to the invention is the propane removed from the absorbate in separation zone IV (and, if appropriate, a portion of residual gas cycle gas).

In the process according to the invention, preference is given to feeding fresh propane exclusively into reaction zone A, as a constituent of the charge gas mixture for reaction zone A. In principle, portions of the fresh propane can, for reasons of explosion safety, also be fed into the charge gas mixtures of the first and/or second oxidation stage of reaction zone B or at any other point in the process.

In this document, the loading of a catalyst bed which catalyzes a reaction step with reaction gas is understood to mean the amount of reaction gas in standard liters (=l (STP); the volume in liters that the corresponding amount of reaction gas would take up under standard conditions (0° C., 1 bar)) which is conducted through one liter of catalyst bed (for example fixed catalyst bed) per hour.

The loading may also be based only on one constituent of the reaction gas. In that case, it is the amount of this constituent in l (STP)/l·h which is conducted through one liter of the catalyst bed per hour (pure inert material beds are not counted toward the fixed catalyst bed). When the catalyst bed consists of a mixture of catalyst and inert shaped diluent bodies, the loading, when it is mentioned in this context, may also be based only on the volume unit of catalyst present.

In this document, an inert gas shall be understood generally to mean a reaction gas constituent which, under the condition of the corresponding reaction, behaves essentially as chemically inert and—each inert reaction gas constituent considered alone—remains chemically unchanged to an extent of more than 95 mol %, preferably to an extent of more than 97 mol % or to an extent of more than 99 mol %.

Useful sources for the molecular oxygen required in reaction zone A are, in addition to residual gas cycle gas stemming from separation zone II, molecular oxygen as such, or a mixture of molecular oxygen and a gas which behaves chemically inertly in reaction zone A (or a mixture of such inert gases) (for example noble gases such as argon, molecular nitrogen, steam, carbon dioxide, etc.). In other words, the molecular oxygen may be fed as a gas to reaction zone A which comprises not more than 50% by volume, preferably not more than 40% by volume or not more than 30% by volume, advantageously not more than 25% by volume or not more than 20% by volume, particularly advantageously not more than 15% by volume or not more than 10% by volume and more preferably not more than 5% by volume or not more than 2% by volume of other gases (constituents) (other than molecular oxygen). Since the oxygen demand in reaction zone A is comparatively low in comparison to that in reaction zone B in the process according to the invention, it is, however, also favorable to use air as the oxygen source for the oxygen demand in reaction zone A in the process according to the invention, especially for reasons of economic viability. From the point of view of minimal gas volumes to be conveyed and to be compressed, preference is given to the supply as pure oxygen into reaction zone A. Propane cycle gas recycled into reaction zone A (coming from separation zone IV) comprises molecular oxygen generally only in traces. The aforementioned applies essentially in the same way to the supply of the molecular oxygen required in reaction zone B. In other words, the supply of molecular oxygen as pure oxygen is advantageous both for the oxygen demand of reaction zone A and of reaction zone B especially because it does not burden the gas streams of the process according to the invention with inert gas, which has to be discharged again in the further course of the cycle process, over and above what is indispensible.

Typical reaction gases B with which reaction zone B can be charged in the process according to the invention have the following contents:
from 4 to 25% by volume of propylene,
from 6 to 70% by volume of propane,
from 0 to 60% by volume of $H_2O$,
from 5 to 60% by volume of $O_2$ and
from 0 to 20, preferably up to 10% by volume of $H_2$.

Reaction gases B preferred in accordance with the invention have the following contents:
from 7 to 25% by volume of propylene,
from 10 to 40% by volume of propane,
from 1 to 10% by volume of $H_2O$,
from 10 to 30% by volume of $O_2$ and
from 0 to 10% by volume of $H_2$.

Reaction gases B very particularly preferred in accordance with the invention for the aforementioned charge have the following contents:
from 15 to 25% by volume of propylene,
from 20 to 40% by volume of propane,
from 2 to 8% by volume of $H_2O$,
from 15 to 30% by volume of $O_2$ and
from 0 to 5% by volume of $H_2$.

The advantageousness of moderate propane contents in reaction gas B is evident, for example, from DE-A 102 45 585.

Within the aforementioned composition framework, it is favorable when the molar ratio $V_1$ of propane present in reaction gas B to propylene present in reaction gas B is from 1 to 9. It is also advantageous within the aforementioned composition framework when the ratio $V_2$ of molecular oxygen present in reaction gas B to propylene present in reaction gas B is from 1 to 2.5. In the context of the present invention, it is also advantageous within the aforementioned composition framework when the ratio $V_3$ of molecular hydrogen present in reaction gas B to propylene present in reaction gas B is from 0 to 0.80 or from 0 to 0.60 or from 0.1 to 0.50. Frequently, the ratio $V_3$ is also from 0.4 to 0.6. It is also advantageous within the aforementioned composition framework when the molar ratio $V_4$ of steam present in reaction gas B to the total molar amount of propane and propylene present in reaction gas B is from 0 or 0.001 to 10.

Particularly advantageously, $V_1$ in the reaction gas B used to charge reaction zone B (in the reaction gas B starting mixture) is from 1 to 7 or to 4, or from 2 to 6 and particularly advantageously from 2 to 5, or from 3.5 to 4.5. It is also preferred for the reaction gas B starting mixture when $V_2$ is from 1.2 to 2.0, or 1.4 or 1.8. Correspondingly, $V_4$ in the reaction gas B starting mixture is preferably from 0.015 to 5, better from 0.01 to 3, advantageously from 0.01 to 1 and particularly advantageously from 0.01 to 0.3 or to 0.1. Preference is given in accordance with the invention to nonexplosive reaction gas B starting mixtures.

What is crucial in answering the question of whether the reaction gas B starting mixture is explosive or not is whether combustion (ignition, explosion) initiated by a local ignition source (for example glowing platinum wire) spreads under the mixture present under certain conditions (pressure, temperature) or not (cf. DIN 51649 and the experiment description in WO 04/007405). When there is spreading, the mixture shall be classified here as explosive. When there is no spreading, the mixture is classified in this document as nonexplosive. When the starting reaction gas mixture of an inventive partial oxidation is nonexplosive, this normally also applies to the reaction gas mixtures formed therefrom in the course of the partial oxidation (cf. WO 04/007405).

Quite generally, it is typical for the process according to the invention that the total content in the reaction gas B starting mixture of constituents other than propylene, molecular hydrogen, steam, propane, molecular nitrogen and molecular oxygen is usually $\leq$20% by volume, or $\leq$15% by volume, or $\leq$10% by volume, or $\leq$5% by volume. Up to 80% by volume of these other constituents of the reaction gas B starting mixture may be ethane and/or methane. Otherwise, such contents may in particular be carbon oxides ($CO_2$, CO) and noble gas, but also traces of secondary component oxygenates such as formaldehyde, benzaldehyde, methacrolein, acetic acid, propionic acid, methacrylic acid, etc. Of course, ethylene, isobutene, n-butane and n-butenes are also included in these possible other constituents of the reaction gas B starting mixture. The content in the reaction gas B starting mixture of molecular nitrogen may vary within a wide range. In principle, this nitrogen content may be up to 70% by volume. In general, the content in the reaction gas B starting mixture of molecular nitrogen will be $\leq$65% by volume, or $\leq$60% by volume, or $\leq$50% by volume, or $\leq$40% by volume, or $\leq$30% by volume, or $\leq$20% by volume, or $\leq$10% by volume, or $\leq$5% by volume. In principle, the $N_2$ content of the reaction gas B starting mixture may be vanishingly small. A minimization of the $N_2$ content in the reaction gas B starting mixture minimizes the gas volume to be conveyed and to be compressed in the process according to the invention.

Conversely, a dilution of reaction gas B with molecular nitrogen reduces propionic acid by-product formation in reaction zone B.

In principle, all processes for heterogeneously catalyzed partial dehydrogenation of propane to propylene known in the prior art are useful for the heterogeneously catalyzed partial dehydrogenation of propane in reaction zone A, as known, for example, from the documents WO 03/076370, WO 01/96271, EP-A 117 146, WO 03/011804, EP-A 7 310 77, U.S. Pat. No. 3,162,60, WO 01/96270, DE-A 331 35 73, DE-A 102 45 585, DE-A 103 16 039, DE-A 10 2005 009891, DE-A 10 2005 013039, DE-A 10 2005 022 798, DE-A 10 2005 009 885, DE-A 10 2005 010 111, DE-A 10 2005 049 699, DE-A 10 2004 032 129, DE 10 2005 056377.5, DE 10 2006 017623.5, DE 10 2006 015235.2, DE 10 2005 061626.7 and DE 10 2005 057197.2, and also the prior art acknowledged in these documents (this is attributable to the fact that the oxidation (combustion) of the molecular hydrogen with molecular oxygen in reaction zone A can in principle follow any process for heterogeneously catalyzed partial dehydrogenation of propane. In principle, the heterogeneously catalyzed dehydrogenation of propane and the combustion of molecular hydrogen within reaction zone A can also be carried out in different reactors, for example reactors connected spatially in series. In this case, it is advantageous that the reaction gas B starting mixture in the process according to the invention does not necessarily comprise molecular oxygen. Quite generally, the process according to the invention in reaction zone A can be performed either in only a single reactor or, for example, in a series connection of more than one reactor. Based on single pass of the propane fed to reaction zone A through reaction zone A, reaction zone A can in principle be configured isothermally by controlled heat exchange with fluid (i.e. liquid or gaseous) heat carriers conducted outside reaction zone A. However, with the same reference basis, it can also be performed adiabatically, i.e. essentially without such controlled heat exchange with heat carriers conducted outside reaction zone A. In the latter case, the gross thermal character, based on single pass of the propane fed to reaction zone A through reaction zone A, by taking the measures recommended in the aforementioned documents and yet to be described below, may be configured endothermically (negative) or else autothermally (essentially zero) or exothermically (positive). It is equally possible to employ all catalysts recommended in the aforementioned documents (including the prior art acknowledged in these documents) in the process according to the invention. In principle, the heterogeneously catalyzed propane dehydrogenation in reaction zone A, irrespective of whether it is operated adiabatically and/or isothermally (it is also possible to alternate from adiabatic to isothermal along reaction zone A and vice versa), can be performed either in a fixed bed reactor (or in a plurality of fixed bed reactors, for example connected in series) or in a moving bed or fluidized bed reactor (the latter is suitable owing to its backmixing, especially for heating of the reaction gas A starting mixture to the reaction temperature in reaction zone A by hydrogen combustion in reaction gas A when molecular oxygen has already been supplied to the reaction gas A starting mixture).

Typically, the heterogeneously catalyzed partial dehydrogenation of propane to propylene requires comparatively high reaction temperatures. The achievable conversion of propane normally reaches the limit of the thermodynamic equilibrium. Typical reaction temperatures are from 300 to 800° C. or from 400 to 700° C., or from 450 to 650° C. One molecule of hydrogen is generated per molecule of propane dehydrogenated to propylene. According to the invention, the working pressure in the overall reaction zone A is appropriately from >1 to 5 bar, preferably from 1.5 to 4 bar and advantageously from 2 to 3 bar. In principle, the working pressure in reaction zone A may also be at higher or lower values than those mentioned above. High temperatures and removal of the $H_2$ reaction product shift the dehydrogenation equilibrium position in reaction zone A toward the propylene to be formed in reaction zone A.

Since the heterogeneously catalyzed dehydrogenation reaction proceeds with increasing volume, the conversion can be increased by lowering the partial pressure of the dehydrogenation products. This can be achieved in a simple manner, for example, by dehydrogenating under reduced pressure (however, performance at elevated pressure is generally advantageous for the catalyst lifetime) and/or by adding essentially inert diluent gases, for example steam, which normally constitutes an inert gas for the dehydrogenation reaction. As a further advantage, dilution with steam generally causes reduced cooking of the catalyst used, since the steam reacts with carbon formed by the principle of coal gasification. The heat capacity of the steam is also capable of compensating for some of the endothermicity of the dehydrogenation.

While steam in limited amounts is normally found to have a promoting effect for the activity of the partial oxidation catalysts in the downstream reaction zone B, an amount over and above this is disadvantageous in reaction zone B for the reasons already mentioned. According to the invention, at least a portion of the hydrogen additionally has to be oxidized to steam in reaction zone A. It is therefore advantageous in accordance with the invention when the amount of steam fed to reaction zone A, based on the reaction gas A fed to the catalyst charge of reaction zone A, is $\leq 20\%$ by volume, preferably $\leq 15\%$ by volume and more preferably $\leq 10\%$ by volume. In general, the amount of steam fed to reaction zone A, on the same basis, will normally, however, be $\geq 1\%$ by volume, in many cases $\geq 2\%$ by volume, or $\geq 3\%$ by volume and frequently 2 5% by volume.

Further diluents suitable for the heterogeneously catalyzed propane dehydrogenation are, for example, nitrogen, noble gases such as He, Ne and Ar, but also compounds such as CO, $CO_2$, methane and ethane. All diluents mentioned may be used either alone or in the form of different mixtures. When the aforementioned diluent gases are formed as a by-product in the cycle gas process according to the invention, or are supplied as fresh gas or a fresh gas constituent, the process according to the invention requires a discharge in a corresponding manner, which is why a corresponding fresh gas feed is less preferred in accordance with the invention. Such possible discharges are present in the different separation zones, in particular separation zones III and IV.

In principle, useful dehydrogenation catalysts for the heterogeneously catalyzed propane dehydrogenation are all of those known in the prior art. They can be divided roughly into two groups, specifically into those which are of oxidic nature (for example chromium oxide and/or aluminum oxide) and into those which consist of at least one generally comparatively noble metal (for example platinum) deposited on a generally oxidic support (for example zirconium dioxide, magnesium oxide, aluminum oxide, silicon dioxide, titanium dioxide, lanthanum oxide and/or cerium oxide). The dehydrogenation catalysts which may be used thus include all of those recommended in WO 01/96270, EP-A 731077, DE-A 10211275, DE-A 10131297, WO 99/46039, U.S. Pat. No. 4,788,371, EP-A 705 136, WO 99/29420, U.S. Pat. Nos. 4,220,091, 5,430,220, 5,877,369, EP-A 117 146, DE-A 199

37 196, DE-A 199 37 105, U.S. Pat. Nos. 3,670,044, 6,566,573, WO 94/29021 and DE-A 199 37 107. In particular, the catalysts according to example 1, example 2, example 3 and example 4 of DE-A 199 37 107 may be used. Finally, the catalysts of German application No. 10 2005 044916 should also be recommended as catalysts to be used for the dehydrogenation in reaction zone A. In the process according to the invention, these catalysts may be the sole catalysts used within reaction zone A, since they generally also catalyze the combustion of molecular hydrogen with molecular oxygen.

In principle, a catalytically active bed within reaction zone A may consist exclusively of catalytically active shaped bodies. However, it is of course also possible for a catalytically active bed within reaction zone A to consist of catalytically active shaped bodies diluted with inert shaped bodies. Such inert shaped bodies may be manufactured, for example, from fired clays (aluminum silicates) or steatite (for example C 220 from CeramTec), or other (preferably essentially free of pores) high-temperature ceramic materials such as aluminum oxides, silicon dioxide, titanium dioxide, magnesium oxide, lanthanum oxide, cerium oxide, zinc aluminum mixed oxide, thorium dioxide, zirconium dioxide, silicon carbide or other silicates such as magnesium silicate and mixtures of aforementioned materials.

Aforementioned materials are also useful for an inert top bed and, if appropriate, final bed of the fixed catalyst bed of the process according to the invention.

The dehydrogenation catalysts are those which comprise from 10 to 99.9% by weight of zirconium dioxide, from 0 to 60% by weight of aluminum oxide, silicon dioxide and/or titanium dioxide, and from 0.1 to 10% by weight of at least one element of the first or second main group, of an element of the third transition group, of an element of the eighth transition group of the Periodic Table of the Elements, lanthanum and/or tin, with the proviso that the sum of the percentages by weight adds up to 100% by weight.

Also particularly suitable is the dehydrogenation catalyst used in the working examples of this document.

In a preferred embodiment, aforementioned dehydrogenation catalysts comprise at least one element of transition group VIII, at least one element of main group I and II, and at least one element of main group III and/or IV, and at least one element of transition group III including lanthanides and actinides. As the element of transition group VIII, the active composition of the dehydrogenation catalysts preferably comprises platinum and/or palladium, more preferably platinum. As elements of main group I and II, the active composition of the aforementioned dehydrogenation catalysts preferably comprises potassium and/or cesium. As elements of transition group III including the lanthanides and actinides, the active composition of the aforementioned dehydrogenation catalysts preferably comprises lanthanum and/or cerium. As elements of main group III and/or IV, the active composition of the aforementioned dehydrogenation catalysts preferably comprises one or more elements from the group consisting of boron, gallium, silicon, germanium, tin and lead, more preferably tin. Most preferably, the active composition of the aforementioned dehydrogenation catalysts comprises at least one representative in each case from the aforementioned element groups.

Generally, the dehydrogenation catalysts may be catalyst extrudates (diameter typically from 0.1 or 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). To perform the heterogeneously catalyzed dehydrogenation in a fluidized bed (or moving bed), correspondingly more finely divided catalyst will be used. For reaction zone A, preference is given in accordance with the invention to the use of fixed catalyst beds.

In principle, neither with regard to the catalyst geometry to be used in the fixed catalyst beds (especially in the case of supported catalysts) nor with regard to the geometry of the inert shaped bodies to be used in the process according to the invention are there any restrictions. Particularly frequently used geometries are solid cylinders, hollow cylinders (rings), spheres, cones, pyramids and cubes, and also extrudates, wagonwheels, stars and monoliths.

The longest dimension of the shaped catalyst bodies and of the inert shaped bodies (longest direct line connecting two points on the shaped body surface) may be from 0.5 mm to 100 mm, often from 1.5 mm to 80 mm, and in many cases from 3 mm to 50 mm or to 20 mm.

In general, the dehydrogenation catalysts (especially those used by way of example in this document and those recommended in DE-A 19 937 107 (especially the exemplary catalysts of this DE-A)) are such that they are capable of catalyzing both the dehydrogenation of propane and the combustion of molecular hydrogen and of propane/propylene. The hydrogen combustion proceeds very much more rapidly both in comparison to the dehydrogenation of propane and in comparison to, for example, its combustion in the case of a competition situation over these catalysts (i.e. they cause by far the lowest activation energy for the combustion of molecular hydrogen under the given conditions). The combustion of propane/propylene generally proceeds in turn more rapidly than the dehydrogenation over these catalysts.

The aforementioned connection makes it possible to manage with the use of only one catalyst type in reaction zone A in the process according to the invention.

Advantageously, it should be ensured that, in reaction zone A, whenever reaction gas A comprises molecular oxygen and comes into contact with above-described catalysts, reaction gas A comprises at least twice the amount of molecular hydrogen relative to the amount of molecular oxygen present therein, since the risk of combustion of propane and/or propylene otherwise rises and the target product yield based on the converted propane raw material in the process according to the invention is reduced.

Of course, the catalysts used for the combustion of the molecular hydrogen to water in reaction zone A may also be those which specifically catalyze this reaction. Such catalysts are described, for example, in the documents U.S. Pat. Nos. 4,788,371, 4,886,928, 5,430,209, 5,530,171, 5,527,979 and 5,563,314.

To perform the heterogeneously catalyzed propane dehydrogenation, useful reactor types and process variants are in principle all of those known in the prior art. Descriptions of such process variants are present, for example, in all prior art documents cited with regard to the dehydrogenation catalysts, and also the prior art cited at the outset of this document.

A comparatively comprehensive description of dehydrogenation processes suitable in accordance with the invention is also present in Catalytica® Studies Division, Oxidative Dehydrogenation and Alternative Dehydrogenation Process, Study Number 4192 OD, 1993, 430 Ferguson Drive, Mountain View, Calif., 94043-5272 U.S.A.

Owing to the comparatively high reaction temperatures required for the heterogeneously catalyzed dehydrogenation of propane, small amounts of high-boiling, high molecular weight organic compounds up to and including carbon are generally formed in reaction zone A in the process according to the invention, which are deposited on the catalyst surface and hence deactivated. In order to minimize this disadvantageous accompanying phenomenon, the propane-containing reaction gas A to be passed over the catalyst surface at elevated temperature for heterogeneously catalyzed dehydrogenation can appropriately be diluted with steam. This is possible in a particularly elegant manner in the process according to the invention, for example, in a simple manner by carrying out the removal of the propane from the absorbate in separation zone IV by stripping by means of steam or by means of a steam-comprising gas (for example of an inert gas) and recycling the propane-laden stripping gas (the propane-laden steam) as propane cycle gas into reaction zone A. The steam would partly or fully eliminate carbon being deposited by the principle of coal gasification under the conditions which otherwise exist and thus prolong the catalyst lifetime.

Another means of eliminating deposited carbon compounds consists in flowing an oxygen-comprising gas (appropriately in the absence of hydrocarbons) through the dehydrogenation catalyst (and also any catalyst used separately for the hydrogen combustion) at elevated temperature from time to time and hence effectively burning off the deposited carbon. However, a certain suppression of the formation of carbon deposits, and hence a prolonging of the catalyst lifetime, is also possible by adding molecular hydrogen to the propane to be dehydrogenated under heterogeneous catalysis before it is conducted over the dehydrogenation catalyst at elevated temperature. This is possible in the process according to the invention, for example, by, if appropriate, in a simple manner, removing any molecular hydrogen still present in the residual gas occurring in separation zone II therefrom by means of a separating membrane upstream of separation zone III (or beyond separation zone III) and recycling it into reaction zone A. Of course, it is also possible at this point to use molecular hydrogen from another source. For example, the molecular hydrogen may also still be present in the residual gas cycle gas recycled, if appropriate, into reaction zone A.

Of course, the possibility also exists of adding a mixture of steam and molecular hydrogen to the propane to be dehydrogenated under heterogeneous catalysis.

Addition of molecular hydrogen to the heterogeneously catalyzed dehydrogenation of propane also reduces the undesired formation of allene (propadiene), propyne and acetylene as by-products.

This allows only fresh propane and propane cycle gas to be fed in the simplest case to reaction zone A to form a reaction gas A to be conducted through the at least one catalyst bed (in this document, also known as charge gas mixture of reaction zone A or reaction gas A starting mixture). The propane cycle gas may already comprise the amount of molecular oxygen (for example when the propane is removed by stripping from the absorbate in separation zone IV and the stripping gas comprises added molecular oxygen, for example in the form of air) which is required to bring about the hydrogen combustion required in accordance with the invention in reaction zone A. However, the reaction gas A starting mixture may also be composed only of fresh propane, propane cycle gas and residual gas cycle gas, in which case the latter may likewise comprise molecular oxygen.

In an advantageous manner, the propane cycle gas in the aforementioned cases will comprise just sufficient steam that it, together with the steam formed in the course of the hydrogen combustion in reaction zone A, can develop its advantageous properties for the overall process. In the above-described cases, there is not necessarily any need for the supply of further gaseous streams into reaction zone A. The conversion desired in reaction zone A proceeds in single pass of reaction gas A through it.

Of course, the reaction gas A to be conducted through the at least one fixed catalyst bed may be formed by adding, in addition to fresh propane, propane cycle gas and, if appropriate, residual gas cycle gas, additional steam and/or additional molecular hydrogen, in order to develop their advantageous action described in this document. The molar ratio of molecular hydrogen to propane in the charge gas mixture of reaction zone A is generally $\leqq 5$, usually $\leqq 3$, in many cases $\leqq 1$ or $\leqq 0.1$.

The molar ratio of steam to propane in the charge gas mixture of reaction zone A may, for example, be from $\geqq 0$ to 30. Appropriately, it will be from 0.05 to 2 and favorably from 0.1 to 0.5.

Moreover, it is also possible to add extra molecular oxygen (in pure form and/or as a mixture with inert gas) and/or extra inert gas as required to the charge gas mixture for reaction zone A. The conversion desired in reaction zone A can then again proceed in single pass of reaction gas A (of the charge gas of reaction zone A) through it, without further gaseous streams being supplied along the reaction path. In this document, the reaction path in reaction zone A shall be understood to mean the flow path of that propane through reaction zone A, as a function of the dehydrogenating conversion (the conversion in the heterogeneously catalyzed dehydrogenation) of this propane, which is fed to reaction gas A before its first pass through at least one catalyst bed of reaction zone A.

A suitable reactor form for such a heterogeneously catalyzed propane dehydrogenation with single pass of the charge gas mixture through reaction zone A and without intermediate gas feeding is, for example, the fixed bed tubular reactor or tube bundle reactor. In this reactor, the dehydrogenation catalyst is disposed in one reaction tube or in a bundle of reaction tubes as a fixed bed. When the combustion of hydrogen required in accordance with the invention in reaction zone A is such that the gross reaction proceeding in reaction zone A proceeds endothermically, the reaction tubes will appropriately be heated from outside in accordance with the invention (it will be appreciated that they may also be cooled if required). This can be effected, for example, by combusting a gas, for example a hydrocarbon such as methane, in the space surrounding the reaction tubes. It is favorable to apply this direct form of catalyst tube heating only to the first 20 to 30% of the fixed bed and to heat the remaining bed length to the required reaction temperature through the radiative heat released in the course of combustion. In this way, an approximately isothermal reaction is achievable. Suitable reaction tube internal diameters are from about 10 to 15 cm. A typical dehydrogenation tube bundle reactor comprises from 300 to 1000 or more reaction tubes. The temperature in the reaction tube interior varies within the range from 300 to 800° C., preferably within the range from 400 to 700° C. Advantageously, reaction gas A starting mixture is fed to the tubular reactor preheated to the reaction temperature. It is possible that product gas (mixture) A leaves the reaction tube with a temperature lower by 50 to 100° C. However, this outlet temperature may also be higher or at the same level. In the aforementioned procedure, the use of oxidic dehydrogenation catalysts based on chromium oxide and/or aluminum oxide is appropriate. The dehydrogenation catalyst is usually employed undiluted. On the industrial scale, a plurality of such tube bundle reactors can be operated in parallel and their product gases A used in a mixture to charge reaction zone B. If appropriate, it is also possible for only two of these reactors to be in dehydrogenation operation, while the catalyst charge is regenerated in the third reactor.

A single pass of the charge gas through reaction zone A can also be effected in a moving bed or fluidized bed reactor, as described, for example, in DE-A 102 45 585 and the literature cited on this subject in this document.

In principle, reaction zone A of the process according to the invention may also consist of, for example, two sections. Such a construction of reaction zone A is advisable especially when the charge gas for reaction zone A does not comprise any molecular oxygen.

In this case, the actual heterogeneously catalyzed dehydrogenation can be effected in the first section and, after an intermediate supply of molecular oxygen and/or a mixture of molecular oxygen and inert gas, the heterogeneously catalyzed combustion of hydrogen required in accordance with the invention can be effected in the second section.

Quite generally, reaction zone A in the process according to the invention will appropriately be operated in such a way that, based on a single pass through reaction zone A, from $\geq 5$ mol % to $\leq 60$ mol %, preferably from $\geq 10$ mol % to $\leq 50$ mol %, more preferably from $\geq 15$ mol % to $\leq 40$ mol %, and most preferably from $\geq 20$ mol % to $\leq 35$ mol % of the total amount of propane fed to reaction zone A is converted in a dehydrogenating manner in reaction zone A. Such a restricted conversion in reaction zone A is normally sufficient in accordance with the invention because the remaining amount of unconverted propane functions substantially as a diluent gas in the downstream reaction zone B and, in the further course of the inventive procedure, can be recycled substantially without loss into reaction zone A. The advantage of a procedure with relatively low propane conversion is that, on single pass of reaction gas A through reaction zone A, the amount of heat required for the endothermic dehydrogenation is comparatively low and comparatively low reaction temperatures are sufficient to achieve the conversion.

Advantageously in accordance with the invention, it may, as already addressed, be appropriate to carry out the propane dehydrogenation in reaction zone A (quasi-)adia-batically (for example with comparatively low propane conversion). This means that the charge gas mixture for reaction zone A will generally first be heated to a temperature of from 500 to 700° C. (or from 550 to 650° C.) (for example by direct firing of the surrounding wall). Normally, a single adiabatic pass through a catalyst bed will then be sufficient in order to achieve both the desired dehydrogenating conversion and the combustion of hydrogen required in accordance with the invention, in the course of which the reaction gas, depending on the quantitative ratio of endothermic dehydrogenation and exothermic combustion of hydrogen will be heated, be cooled or behave in a thermally neutral manner in the gross evaluation. Preference is given in accordance with the invention to an adiabatic operating mode in which the reaction gas cools by from about 30 to 200° C. in single pass. If required, in a second section of reaction zone A, hydrogen formed in the dehydrogenation can be postcombusted under heterogeneous catalysis with intermediately fed molecular oxygen. This combustion can equally be carried out adiabatically.

Remarkably, especially in adiabatic operation, a single shaft furnace reactor which is flowed through axially and/or radially by reaction gas A is sufficient as a fixed bed reactor.

In the simplest case, this is a single closed reaction volume, for example a vessel, whose internal diameter is from 0.1 to 10 m, possibly even from 0.5 to 5 m, and in which the fixed catalyst bed is placed on a support device (for example a grid). The reaction volume which has been charged with catalyst and is substantially heat-insulated in adiabatic operation is flowed through axially by the hot reaction gas A comprising propane. The catalyst geometry may be either spherical or annular or extrudate-shaped. Since the reaction volume can be realized in this case by a very inexpensive apparatus, all catalyst geometries which have a particularly low pressure drop are preferable. These are in particular catalyst geometries which lead to a large cavity volume or are in structured form, for example monoliths or honeycombs. To realize radial flow of reaction gas A comprising propane, the reactor may, for example, consist of two concentric cylindrical grids disposed in a shell and the catalyst bed may be arranged in their annular gap. In the adiabatic case, the metal shell would in turn be thermally insulated if appropriate.

Suitable inventive catalyst charges for a heterogeneously catalyzed propane dehydrogenation are especially also the catalysts disclosed in DE-A 199 37 107, in particular all of those disclosed by way of example, and mixtures thereof with geometric shaped bodies inert with respect to the heterogeneously catalyzed dehydrogenation.

After a prolonged operating time, the aforementioned catalysts can be regenerated, for example, in a simple manner by, at an entrance temperature of from 300 to 600° C., frequently from 400 to 550° C., initially passing air (preferably) diluted with nitrogen and/or steam over the catalyst bed in first regeneration stages. The catalyst (bed) loading with regeneration gas (e.g. air) may, for example, be from 50 to 10 000 h$^{-1}$ and the oxygen content of the regeneration gas may be from 0.1 or 0.5 to 20% by volume.

In subsequent further regeneration stages, it is possible to use air as the regeneration gas under otherwise identical regeneration conditions. Appropriately from application point of view, it is recommended to flush the catalyst with inert gas (for example N$_2$) before it is regenerated.

Subsequently, it is generally advisable to regenerate with pure molecular hydrogen or with molecular hydrogen diluted with inert gas (preferably steam and/or nitrogen) (the hydrogen content should be $\geq 1$% by volume) under otherwise identical conditions.

The heterogeneously catalyzed propane dehydrogenation in reaction zone A of the process according to the invention can be operated with comparatively low propane conversion ($\leq 30$ mol %) in all cases at the same catalyst (bed) loadings (relating both to the reaction gas overall and to propane present therein) as the variants with high propane conversion ($\geq 30$ mol %). This loading with reaction gas A may, for example, be from 100 to 40 000 or to 10 000 h$^{-1}$, frequently from 300 to 7000 h$^{-1}$, i.e. in many cases from about 500 to 4000 h$^{-1}$. The aforementioned loadings can also be applied to any catalyst beds used specifically for hydrogen combustion in reaction zone A.

In a particularly elegant manner, the heterogeneously catalyzed propane dehydrogenation in reaction zone A (especially in the case of propane conversions of from 15 to 35 mol % based on single pass) can be implemented in a tray reactor, which is why reaction zone A preferably comprises at least one such reactor.

This reactor comprises more than one catalyst bed catalyzing the dehydrogenation in spatial succession. The catalyst bed number may be from 1 to 20, appropriately from 2 to 8, but also from 3 to 6. Increased propane conversions can be achieved increasingly readily with increasing number of trays. The catalyst beds are preferably arranged in radial or axial succession. Appropriately from an application point of view, the fixed catalyst bed type is used in such a tray reactor.

In the simplest case, the fixed catalyst beds in a shaft furnace reactor are arranged axially or in the annular gaps of concentric cylindrical grids. However, it is also possible to arrange the annular gaps in segments one above another and to conduct the gas, after it has passed radially through one segment, into the next segment above it or below it.

Appropriately, reaction gas A is subjected to intermediate heating in the tray reactor on its way from one catalyst bed to the next catalyst bed, for example by passing it over heat exchanger surfaces (e.g. ribs) heated with hot gases or by passing it through pipes heated with hot combustion gases (if required, it is also possible to effect intermediate cooling in a corresponding manner).

When the tray reactor is otherwise operated adiabatically, it is sufficient especially for propane conversions of $\leq 30$ mol %, in particular when using the catalysts described in DE-A 199 37 107, especially those of the exemplary embodiments, to conduct the reaction gas mixture into the dehydrogenation reactor preheated to a temperature of from 450 to 550° C. (preferably from 450 to 500° C.) and to keep it in this temperature range within the tray reactor. This means that the entire propane dehydrogenation can thus be realized at extremely low temperatures, which is found to be particularly favorable for the lifetime of the fixed catalyst beds between two regenerations. For higher propane conversions, the reaction gas mixture is appropriately conducted into the dehydrogenation reactor preheated to higher temperatures (these may be up to 700° C.) and kept in this elevated temperature range within the tray reactor.

It is even more elegant to carry out the above-outlined intermediate heating in a direct way (enables an autothermal method). To this end, a limited amount of molecular oxygen is added to reaction gas A either before it flows through the first catalyst bed (for example as a constituent of residual gas cycle gas and/or of propane cycle gas) (in that case, reaction gas A starting mixture should advantageously comprise added molecular hydrogen) and/or between the downstream catalyst beds. It is thus possible (generally catalyzed by the dehydrogenation catalysts themselves) to bring about the combustion, required in accordance with the invention, of molecular hydrogen which is present in reaction gas A, has been formed in the course of the heterogeneously catalyzed propane dehydrogenation and/or has been added to reaction gas A in a particularly selective and controlled manner (it may also be appropriate from an application point of view to insert catalyst beds in the tray reactor which are charged with catalyst which particularly specifically (selectively) catalyzes the combustion of hydrogen (examples of useful such catalysts include those of the documents U.S. Pat. Nos. 4,788,371, 4,886,928, 5,430,209, 5,530,171, 5,527,979 and 5,563,314; for example, such catalyst beds may be accommodated in the tray reactor in alternation to the beds comprising dehydrogenation catalyst; these catalysts are also suitable for the above-described hydrogen combustion in a second section of reaction zone A)). Depending on the amount of molecular hydrogen combusted, the heat of reaction released thus allows an exothermic operating mode overall, or an autothermal operating mode overall (the gross thermal character is substantially zero), or an endothermic operating mode overall for the heterogeneously catalyzed propane dehydrogenation. As the selected residence time of the reaction gas in the catalyst bed increases, propane dehydrogenation is thus possible at decreasing or substantially constant temperature, which enables particularly long lifetimes between two regenerations and is preferred in accordance with the invention.

Especially when molecular hydrogen is combusted both in the course of the heterogeneously catalyzed dehydrogenation of propane (phase 1) and after the heterogeneously catalyzed dehydrogenation of propane (phase 2), it is appropriate in accordance with the invention first to cool the reaction gas of reaction zone A present after completion of the heterogeneously catalyzed dehydrogenation, in the amount in which it is fed to the final hydrogen combustion in reaction zone A (a portion can be recycled as dehydrogenation cycle gas into reaction zone A as one of the propane-comprising feed streams), by indirect heat exchange with the constituents of the reaction gas A charge mixture other than propane cycle gas and dehydrogenation cycle gas, and, after the final combustion of molecular hydrogen in reaction zone A, to cool product gas A likewise by indirect heat exchange, but with propane cycle gas, before it is treated further. This is especially true when reaction zone A is configured exothermically overall.

Generally, oxygen feeding as described above should be undertaken in accordance with the invention in such a way that the oxygen content of reaction gas A, based on the amount of molecular hydrogen present therein, is from 0.5 to 50, or to 40, or to 30% by volume, preferably from 10 to 25% by volume. Useful oxygen sources include, as already stated, both pure molecular oxygen (preferred in accordance with the invention) or molecular oxygen diluted with inert gas, for example CO, $CO_2$, $N_2$ and/or noble gases, but especially also air. Preferably in accordance with the invention, the molecular oxygen is fed in as gas which comprises not more than 30% by volume, preferably not more than 25% by volume, advantageously not more than 20% by volume, more advantageously not more than 15% by volume, better not more than 10% by volume and more preferably not more than 5% by volume of other gases (other than molecular oxygen). Particularly advantageously, the oxygen feeding described is effected in pure form.

Since the combustion of 1 mol of molecular hydrogen to $H_2O$ affords about twice as much energy (approx. 240 kJ/mol) as the dehydrogenation of 1 mol of propane to propylene and $H_2$ consumes (approx. 120 kJ/mol), an autothermal configuration of reaction zone A in the adiabatic tray reactor as described can be combined efficiently with the contemplated advantage of the inventive procedure, given that it entails precisely the combustion of an amount of hydrogen of about 50 mol % of the amount of molecular hydrogen formed in the dehydrogenation in reaction zone A.

However, the advantage of the process according to the invention does not only come into effect when an amount of hydrogen of about 50 mol % of the amount of molecular hydrogen formed in reaction zone A is combusted in reaction zone A. Instead, this advantage comes into effect even when an amount of hydrogen of from 25 to 95 mol %, or to 100 mol %, or from 30 to 90 mol %, or from 35 to 85 mol %, or from 40 to 80 mol %, or from 45 to 75 mol %, or from 50 to 70 mol %, or from 35 to 65 mol %, or from 40 to 60 mol %, or from 45 to 55 mol % of the amount of molecular hydrogen formed in reaction zone A is combusted in reaction zone A to give water (preferably in the above-described operating mode of an adiabatic tray reactor).

In general, feeding of oxygen as described above should be undertaken such that the oxygen content of reaction gas A, based on the amount of propane and propylene present therein, is from 0.01 or 0.5 to 3% by volume.

The isothermicity of the heterogeneously catalyzed propane dehydrogenation can be improved further by incorporating closed (for example tubular) internals which have favorably, but not necessarily, been evacuated before filling in the spaces between the catalyst beds in the tray reactor. Such internals may also be placed into the particular catalyst bed. These internals comprise suitable solids or liquids which evaporate or melt above a certain temperature and consume heat as they do so, and, when the temperature falls below this value, condense again and release heat as they do so.

Another means of heating the charge gas mixture for the heterogeneously catalyzed propane dehydrogenation in reaction zone A to the required reaction temperature consists in combusting a portion of the propane and/or $H_2$ present therein by means of molecular oxygen present in the charge gas mixture on entry into reaction zone A (for example over suitable specific combustion catalysts, for example by simply passing it through and/or passing it over) and, by means of the heat of combustion thus released, bringing about the heating to the reaction temperature desired for the dehydrogenation (such a procedure is (as already mentioned) advantageous especially in a fluidized bed reactor).

Preferably in accordance with the invention, reaction zone A will be configured adiabatically (externally thermally insulated).

In accordance with the above, reaction zone A of the process according to the invention can be configured as described in the documents DE-A 10 2004 032 129 and DE-A 10 2005 013 39, but with the difference that the charge gas mixture of reaction zone A used is a mixture of fresh propane, steam-comprising propane cycle gas and (if appropriate molecular oxygen-comprising) residual gas cycle gas. Reaction zone A is implemented as a (preferably adiabatic) tray reactor in which catalyst beds (preferably fixed beds) are arranged in radial or axial succession. Advantageously, the number of catalyst bed trays in such a tray reactor is three. Preference is given to carrying out the heterogeneously catalyzed partial propane dehydrogenation autothermally. To this end, a limited amount of molecular oxygen or such a mixture comprising it with inert gas is added to the charge gas mixture of reaction zone A beyond the first (fixed) catalyst bed passed through and between the (fixed) catalyst beds downstream of the first (fixed) catalyst bed in flow direction (for example as described in DE 10 2006 017623.5). Thus, generally catalyzed by the dehydrogenation catalysts themselves, limited combustion of hydrogen formed in the course of the heterogeneously catalyzed propane dehydrogenation (and, if appropriate, of propane and/or propylene to a minor extent at most) will be brought about, whose exothermic thermal character essentially maintains the dehydrogenation temperature.

Appropriately, the partial heterogeneously catalyzed dehydrogenation of propane is essentially operated distributed over the three catalyst trays such that the conversion of the propane conducted into the reactor, based on single reactor pass, is approx. 20 mol % (it will be appreciated that it may also be 30 mol %, or 40 mol %, or 50 mol % or more in the process according to the invention). The selectivity of propylene formation achieved is regularly 90 mol %. The maximum contribution of a single tray to the conversion migrates from the front backward in flow direction with increasing operating time. In general, the catalyst charge is regenerated before the third tray in flow direction provides the maximum contribution to the conversion. Advantageously, the regeneration is effected when the carbonization of all trays has attained an identical extent.

Finally, in a (fixed) catalyst bed arranged downstream of the dehydrogenation, after preceding intermediate oxygen feeding, essentially sole combustion of molecular hydrogen can also be effected. This can in principle go to such a degree that the product gas A which then leaves reaction zone A essentially no longer comprises any molecular hydrogen.

It is quite generally favorable for the above-described heterogeneously catalyzed partial dehydrogenation of propane when the loading on the total amount of catalyst (sum over all beds) with the total amount of propane and propylene is $\geq 500$ l (STP)/l·h and $\leq 20\,000$ l (STP)/l·h (typical values are from 1500 l (STP)/l·h to 2500 l (STP)/l·h). The maximum reaction temperature within an individual fixed catalyst bed is advantageously kept at from 500° C. to 600° C. (or to 650° C.).

A disadvantage of the above-described process with a reaction gas A charge mixture which already comprises molecular oxygen is that virtually all catalysts which catalyze the dehydrogenation of propane also catalyze the combustion (full oxidation of propane and propylene to carbon oxides and steam) of propane and propylene with molecular oxygen.

In addition to the measure of adding a molecular hydrogen-comprising gas to the reaction gas A charge gas mixture as already described, this can be counteracted according to DE-A 102 11 275 by dividing the product gas withdrawn from the dehydrogenation zone (which can be followed in reaction zone A by another zone for combustion of molecular hydrogen) into two portions of identical composition in order to feed only one of the two portions (if appropriate after preceding partial or full combustion of molecular hydrogen present therein) to the partial oxidation as product gas A or product gas A*, while the other portion is recycled into the dehydrogenation as a constituent of reaction gas A (generally of the reaction gas A charge gas mixture). The molecular hydrogen present in this dehydrogenation cycle gas coming from the dehydrogenation itself is then intended to protect the propane and, if appropriate, propylene present in the charge gas mixture for reaction zone A from the molecular oxygen which is likewise present therein. This protection is based on the fact that, as already stated, the combustion, normally catalyzed heterogeneously by the same catalysts, of molecular hydrogen to water is preferred kinetically over the full combustion of propane and/or propylene.

Following the teaching of DE-A 102 11 275, the dehydrogenation cycle gas circulation will appropriately be realized by the jet pump principle (it is also referred to as loop mode; propane cycle gas may function as the motive jet). The aforementioned document also addresses the possibility of adding molecular hydrogen additionally to the charge gas mixture for reaction zone A as further oxidation protection (this may, for example, be molecular hydrogen which has been removed by means of a separating membrane from residual gas which stems from separation zone II and still comprises molecular hydrogen).

Typical reaction gas A charge gas mixtures (reaction gases A forming in reaction zone A) in processes according to the invention have the following contents:

from 55 to 80% by volume of propane,
from 0.1 to 20% by volume of propylene,
from 0 to 10% by volume of $H_2$,
from 0 to 5% by volume of $O_2$,
from 0 to 20% by volume of $N_2$, and
from 5 to 15% by volume of $H_2O$.

Reaction gas A charge gas mixtures preferred for the process according to the invention (the gas mixture which enters the first fixed catalyst bed in reaction zone A in flow direction of reaction gas A) have the following contents:

from 55 to 80% by volume of propane,
from 0.1 to 20% by volume of propylene,
from 2 to 10% by volume of $H_2$,
from 1 to 5% by volume of $O_2$,
from 0 to 20% by volume of $N_2$, and
from 5 to 15% by volume of $H_2O$.

The proportion of the constituents of the reaction gas A charge gas mixtures other than the listed constituents is generally in total $\leq 10\%$ by volume and preferably $\leq 6\%$ by volume.

Typical product gases A have the following contents:
from 30 to 50% by volume of propane,
from 15 to 30% by volume of propylene,
from 0 to 10% by volume of $H_2$, preferably from 0 to 6% by volume of $H_2$,
from 10 to 25% by volume of $H_2O$,
from 0 to 1% by volume of $O_2$, and
from 0 to 35% by volume of $N_2$.

The proportion of the constituents of the product gases A other than the constituents listed is generally $\leq 10\%$ by volume.

The temperature of the product gas A withdrawn from reaction zone A is typically from 300 to 800° C., preferably from 400 to 700° C. and more preferably from 450 to 650° C.

The pressure of the product gas A leaving reaction zone A is generally from >1 to 5 bar, preferably from 1.5 to 4 bar and advantageously from 2 to 3 bar.

According to the invention, product gas A is then used, either without further secondary component removal (but preferably after mechanical removal of solid particles present therein according to the teaching of DE-A 10 316 039) or after condensative removal (brought about by direct and/or indirect cooling) of a portion or of the entirety of the steam present in product gas A (i.e. as product gas A*), to charge the at least one oxidation reactor in reaction zone B with reaction gas B.

Irrespective of whether a condensative removal of water from product gas A is undertaken, it is appropriate in accordance with the invention to cool the hot product gas A before its further use in reaction zone B at least by indirect heat exchange with propane cycle gas (and if appropriate other constituents of the reaction gas A charge gas mixture (normally excluding dehydrogenation cycle gas) and thus to heat propane cycle gas (and if appropriate the other constituents of the reaction gas A charge gas mixture).

Otherwise, for the use of product gas A or of product gas A* to charge the at least one oxidation reactor in reaction zone B, it is sufficient to add that amount of molecular oxygen which is required for the attainment of the objective in reaction zone B to product gas A or to product gas A*.

This addition can, as already stated, in principle be effected as pure oxygen or as a mixture (for example air) of molecular oxygen and one or more gases which behave chemically inertly in reaction zone B (for example $N_2$, $H_2O$, noble gases, $CO_2$) (also referred to in this document as primary oxygen sources). Preferably in accordance with the invention, it is effected as gas which comprises not more than 30% by volume, preferably not more than 25% by volume, advantageously not more than 20% by volume, particularly advantageously not more than 15% by volume, better not more than 10% by volume and more preferably not more than 5% by volume or not more than 2% by volume of other gases other than molecular oxygen. Very particularly advantageous at this point is the use of pure oxygen.

Normally, the amount of molecular oxygen added is such that the molar ratio of molecular oxygen present to propylene present in the charge gas for reaction zone B (reaction gas B starting mixture) is $\geq 1$ and $\leq 3$. Before the molecular oxygen-comprising gas is added to product gas A or product gas A*, its temperature has advantageously been adjusted to a value of from 250 to 370° C., particularly advantageously from 270 to 320° C. The gas comprising the molecular oxygen is present in the feed to reaction gas A or reaction gas A* compressed to a pressure which is normally above the pressure of reaction gas A or A* (if appropriate up to 1 bar), so that the gas comprising the molecular oxygen can be throttled in a simple manner into reaction gas A or A* (when the oxygen source used is air, it is normally compacted by using a radial compressor, as described, for example, by DE-A 103 53 014). The temperature of the gas comprising the molecular oxygen is normally such that the desired temperature (frequently from 240 to 300° C.) for the reaction gas B charge mixture is established. In general, this temperature of the molecular oxygen-comprising gas is from 100 to 200° C.

Typical reaction gas B charge gas mixtures comprise:
from 10 to 40% by volume of propane,
from 5 to 25% by volume of propylene,
from 0 to 10% by volume of $H_2$,
from 10 to 30% by volume of $O_2$, and
from 1 to 10% by volume of $H_2O$.

Preferred reaction gas B charge gas mixtures comprise:
from 15 to 40% by volume of propane,
from 7 to 20% by volume of propylene,
from 0 to 6% by volume of $H_2$,
from 15 to 30% by volume of $O_2$, and
from 1 to 7% by volume of $H_2O$.

In the process according to the invention, the entrance pressure of reaction gas B into the at least one oxidation reactor of reaction zone B will normally appropriately be from >1 bar to 4 bar, usually from 1.3 bar to 3 bar, in many cases from 1.5 to 2.5 bar.

In a manner known per se, the heterogeneously catalyzed gas phase partial oxidation of propylene to acrylic acid with molecular oxygen proceeds in principle in two steps successive along the reaction coordinate, of which the first leads to acrolein, and the second from acrolein to acrylic acid.

This reaction sequence in two steps successive in time opens up the possibility in a manner known per se of terminating the process according to the invention in reaction zone B at the stage of acrolein (the stage of predominant acrolein formation) and undertaking the target product removal at this stage, or continuing the process according to the invention up to predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the fixed catalyst bed, are appropriately adjusted in an optimizing manner in each of the two oxidation stages.

Although the multimetal oxides comprising the elements Mo, Fe, Bi which are particularly suitable as active compositions for the catalysts of the first oxidation stage (propylene→acrolein) are also capable to a certain extent of catalyzing the second oxidation stage (acrolein→acrylic acid), preference is normally given for the second oxidation stage to catalysts whose active composition is at least one multimetal oxide comprising the elements Mo and V.

The process, to be carried out in reaction zone B in accordance with the invention, for the heterogeneously catalyzed partial oxidation of propylene over fixed catalyst beds whose catalysts have, as an active composition, at least one multimetal oxide comprising the elements Mo, Fe and Bi is thus suitable in particular as a one-stage process for preparing acrolein (and acrylic acid if appropriate) or as the first reaction stage for the two-stage preparation of acrylic acid.

The realization of the one-stage heterogeneously catalyzed partial oxidation of propylene to acrolein and acrylic acid if appropriate or the two-stage heterogeneously catalyzed partial oxidation of propylene to acrylic acid using a reaction gas B obtained in accordance with the invention may specifically be carried out as described in the documents EP-A 70 07 14

(first reaction stage; as described there, but also in corresponding countercurrent mode of salt bath and starting reaction gas mixture over the tube bundle reactor), EP-A 70 08 93 (second reaction stage; as described there, but also in corresponding countercurrent mode), WO 04/085369 (especially this document is regarded as being an integral part of this document) (as a two-stage process), WO 04/85363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (one-stage or two-stage), WO 04/085368 (as a two-stage process), DE 10 2004 021 764 (two-stage), WO 04/085362 (first reaction stage), WO 04/085370 (second reaction stage), WO 04/085365 (second reaction stage), WO 04/085367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage (propylene to acrolein) is a reaction gas B generated in accordance with the invention. Regarding the remaining parameters, the procedure is as in the working examples of the documents mentioned (especially regarding the fixed catalyst beds and reactant loading of the fixed catalyst beds). When the procedure in the aforementioned working examples of the prior art is in two stages and there is secondary oxygen feeding (secondary air feeding in a manner less preferred in accordance with the invention) between the two reaction stages, the feeding is undertaken in an appropriate manner, but is adjusted in its amount to the effect that the molar ratio of molecular oxygen to acrolein in the charge gas mixture of the second reaction stage corresponds to that in the working examples of the documents mentioned.

Advantageously in accordance with the invention, the amounts of oxygen in reaction zone B are such that product gas B still comprises unconverted molecular oxygen (appropriately from $\geq 0.5$ to 6% by volume, advantageously from 1 to 5% by volume, preferably from 2 to 4% by volume). In the case of a two-stage procedure, the aforementioned applies to each of the two oxidation stages.

Multimetal oxide catalysts particularly suitable for the particular oxidation stage have been described many times before and are well known to those skilled in the art. For example, EP-A 253 409 refers on page 5 to corresponding US patents.

Favorable catalysts for the particular oxidation stage are also disclosed by DE-A 44 31 957, DE-A 10 2004 025 445 and DE-A 44 31 949. This is especially true of those of the general formula I in the two aforementioned preceding documents. Particularly advantageous catalysts for the particular oxidation stage are disclosed by the documents DE-A 103 25 488, DE-A 103 25 487, DE-A 103 53 954, DE-A 103 44 149, DE-A 103 51 269, DE-A 103 50 812 and DE-A 103 50 822.

For the inventive reaction stage for the heterogeneously catalyzed gas phase partial oxidation of propylene to acrolein or acrylic acid or a mixture thereof, useful multimetal oxide compositions are in principle all multimetal oxide compositions comprising Mo, Bi and Fe as the active composition.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700 714.

Also suitable for this reaction stage are the multimetal oxide catalysts comprising Mo, Bi and Fe which are disclosed in the documents Research Disclosure No. 497012 of Aug. 29, 2005 (inadvertently, in the working examples there, the specific surface area was reported mistakenly in cm$^2$/g instead of correctly in m$^2$/g with the same numerical value), DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10$ $SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide If catalyst according to example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and, if appropriate, acrylic acid can be encompassed by the general formula IV $$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form (for example in fluidized bed reactors).

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein (and acrylic acid if appropriate)" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinders, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 29 09 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length ×internal diameter). The fineness of the catalytically active oxide compositions to be applied to the surface of the support body is of course adjusted to the desired coating thickness (cf. EP-A 714 700).

Multimetal oxide active compositions to be used for the step from propylene to acrolein (and if appropriate acrylic acid) are also compositions of the general formula V

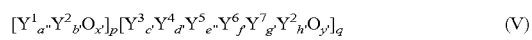  (V)

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1{}_{a'}Y^2{}_{b'}O_{x'}$ which are delimited from their local environment owing to their different composition from their local environment, and whose maximum diameter (longest direct line passing through the center of the region and connecting two points on the surface (interface) of the region) is from 1 nm to 100 µm, frequently from 10 nm to 500 nm or from 1 µm to 50 or 25 µm.

Particularly advantageous multimetal oxide compositions V suitable in accordance with the invention are those in which $Y^1$ is only bismuth.

Among these, preference is given in turn to those of the general formula VI

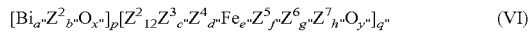

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h'' from 0 to 1,
x'',y''=numbers which are determined by the valency and frequency of the elements in VI other than oxygen,
p'',q''=numbers whose p''/q'' ratio is from 0.1 to 5, preferably from 0.5 to 2, and very particular preference is given to those compositions VI in which $Z^2{}_{b''}$=(tungsten)$_{b''}$ and $Z^2{}_{12}$=(molybdenum)$_{12}$.

It is also advantageous when at least 25 mol % (preferably at least 50 mol % and more preferably 100 mol %) of the total proportion of $[Y^1{}_{a'}Y^2{}_{b'}O_{x'}]_p([Bi_{a''}Z^2{}_{b''}O_{x''}]_{p''})$ of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1{}_{a'}Y^2{}_{b'}O_{x'}[Bi_{a''}Z^2{}_{b''}O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as an upstream bed which protects them and/or heats the gas mixture.

For the second step (the second reaction stage), the heterogeneously catalyzed gas phase partial oxidation of acrolein to acrylic acid, useful active compositions for the catalysts required are, as already stated, in principle all multimetal oxide compositions comprising Mo and V, for example those of DE-A 100 46 928.

A multitude thereof, for example those of DE-A 198 15 281, can be encompassed by the general formula VIII

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from O to 0.2,
f=from 0 to 1 and
n=a number which is determined by the valency and frequency of the elements in VII other than oxygen.

However, multimetal oxides VII which are very particularly preferred in accordance with the invention are those of the general formula VIII

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5,
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form (for example in a fluidized bed reactor) or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length× internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step are also compositions of the general formula IX $$[D]_p[E]_q \quad (IX)$$

in which the variables are each defined as follows:
$D=Mo_{12}V_{a''}Z^1_{b''}Z^2_{c''}Z^3d\text{-}Z^4_{e''}Z^5_{f''}Z^6_{g''}O_{x''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a''=from 1 to 8,
b''=from 0.2 to 5,
c'', =from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements in IX other than oxygen and
p,q=numbers other than zero whose p/q ratio is from 160:1 to 1:1, and which are obtainable by separately performing a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The performance of the partial oxidation of the process according to the invention, from propylene to acrolein (and acrylic acid if appropriate), may be carried out with the catalysts described, for example, in a one-zone multiple catalyst tube fixed bed reactor, as described by DE-A 44 31 957. In this case, reaction gas mixture and heat carrier (heat exchange medium) may be conducted in cocurrent or in countercurrent viewed over the reactor.

The reaction pressure is typically in the range from 1 to 3 bar and the overall space velocity on the fixed catalyst bed of reaction gas B is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or $\geq$140 l (STP)/l·h, or $\geq$150 l (STP)/l·h, or $\geq$160 l (STP)/l·h are particularly preferred in accordance with the invention, since the inventive starting reaction gas mixture for reaction zone B, owing to the presence of unconverted propane and, if appropriate, molecular hydrogen, causes favorable hotspot behavior (all of the aforementioned applies irrespective of the specific selection of the fixed bed reactor).

The flow to the one-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may, as already stated, be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 30 or up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Research Disclosure No. 497012 of Aug. 29, 2005, example 1 of DE-A 100 46 957 or according to example 3 of DE-A 100 46 957 and the inert material used is steatite rings having the geometry 7 mm×7 mm×4 mm (external diameter×height×internal diameter). With regard to the salt bath temperature, the statements of DE-A 4 431 957 apply.

However, the performance of the partial oxidation in reaction zone B, from propylene to acrolein (and acrylic acid if appropriate), may also be carried out with the catalysts described, for example, in a two-zone multiple catalyst tube fixed bed reactor, as described by DE-A 199 10 506, DE-A 10 2005 009 885, DE-A 10 2004 032 129, DE-A 10 2005 013 039 and DE-A 10 2005 009 891, and also DE-A 10 2005 010 111. In both of the above-described cases (and quite generally in the process according to the invention), the propene conversion achieved in single pass is normally at values of $\geq$90 mol %, or $\geq$95 mol %, and the selectivity of acrolein formation at values of $\geq$90 mol %. Advantageously in accordance with the invention, the inventive partial oxidation of propene to acrolein, or acrylic acid or mixtures thereof, is effected as described in EP-A 1 159 244 and most preferably as described in WO 04/085363 and in WO 04/085362.

The documents EP-A 1 159 244, WO 04/085363 and WO 04/085362 are considered to be an integral part of this document.

In other words, a partial oxidation of propylene to acrolein (and acrylic acid if appropriate) to be carried out in reaction zone B can be carried out particularly advantageously over a fixed catalyst bed having increased propylene loading and at least two temperature zones.

In this regard, reference is made, for example, to EP-A 1 159 244 and WO 04/085362.

The performance of the second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture and heat carrier can be conducted in cocurrent viewed over the reactor. In general, the product gas mixture of the preceding inventive propylene partial oxidation to acrolein is in principle conducted as such (if appropriate after intermediate cooling (this may be effected indirectly or directly by, for example, secondary oxygen addition (or secondary air addition in a manner less preferred in accordance with the invention)) thereof), i.e. without secondary component removal, into the second reaction stage, i.e. into the acrolein partial oxidation.

The molecular oxygen required for the second step, the acrolein partial oxidation, may already be present in the reaction gas B starting mixture for the propylene partial oxidation to acrolein. However, it may also be added partly or fully directly to the product gas mixture of the first reaction stage, i.e. the propylene partial oxidation to acrolein (this can be effected in the form of secondary air, but may preferably be effected in the form of pure oxygen or of mixtures of inert gas and oxygen (with preferably $\leq$50% by volume, or $\leq$40% by volume, or $\leq$30% by volume, or $\leq$20% by volume, or $\leq$10% by volume, or $\leq$5% by volume, or $\leq$2% by volume)). For pressure and temperature of the secondary oxygen source, the same applies as was stated for the primary oxygen source.

Irrespective of the procedure, the charge gas mixture (starting reaction gas mixture) of such a partial oxidation of acrolein to acrylic acid advantageously has the following contents:

from 3 to 25% by volume of acrolein,
from 5 to 65% by volume of molecular oxygen,
from 6 to 70% by volume of propane,
from 0 to 20% by volume of molecular hydrogen,
from 8 to 65% by volume of steam and
from 0 to 70% by volume of molecular nitrogen.

The aforementioned starting reaction gas mixture preferably has the following contents:

from 5 to 20% by volume of acrolein,
from 5 to 15% by volume of molecular oxygen,
from 10 to 40% by volume of propane,
from 0 to 10% by volume of molecular hydrogen and
from 5 to 30% by volume of steam.

The aforementioned starting reaction gas mixture most preferably has the following contents:

from 10 to 20% by volume of acrolein,
from 7 to 15% by volume of molecular oxygen,
from 20 to 40% by volume of propane,
from 3 to 10% by volume of molecular hydrogen and
from 15 to 30% by volume of steam.

The nitrogen content in the aforementioned mixtures will generally be $\leq 20\%$ by volume, preferably $\leq 15\%$ by volume, more preferably $\leq 10\%$ by volume and most preferably $\leq 5\%$ by volume. The ratio of the molar amounts of $O_2$ and acrolein present in the charge gas mixture for the second oxidation stage, $O_2$: acrolein, is, advantageously in accordance with the invention, generally $\geq 0.5$ and $\leq 2$, frequently $\geq 1$ and $\leq 1.5$.

The $CO_2$ content of the charge gas mixture for the second oxidation stage will generally be $\leq 5\%$ by volume.

As in the first reaction stage (propylene→acrolein), the reaction pressure in the second reaction stage (acrolein→acrylic acid) too is typically in the range from >1 to 4 bar, preferably from 1.3 to 3 bar, in many cases from 1.5 to 2.5 bar, and the total space velocity on the fixed catalyst bed of (starting) reaction gas mixture is preferably from 1500 to 4000 or to 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 135 l (STP)/l·h, or $\geq 140$ l (STP)/l·h, or $\geq 150$ l (STP)/l·h, or $\geq 160$ l (STP)/l·h are particularly preferred, since the starting reaction gas mixture to be used in accordance with the invention, owing to the presence of propane and, if appropriate, molecular hydrogen, likewise results in favorable hotspot behavior.

The temperature of the charge gas mixture for the second oxidation stage is generally from 220 to 270° C.

The acrolein conversion based on single pass of the reaction gas mixture through the fixed catalyst bed of the second oxidation stage is appropriately normally $\geq 90$ mol % and the accompanying selectivity of acrylic acid formation $\geq 90$ mol %.

The flow to the one-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes from bottom to top as follows:

first, to a length of from 50 to 80 or to 70% of the catalyst tube length, either only catalyst or a mixture of catalyst and inert material, the latter, based on the mixture, making up a proportion by weight of up to 30 (or 20) % by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the catalyst bed and high steam contents of the charge gas mixture), section B may also consist of two successive catalyst dilutions (for the purpose of minimizing hotspot temperature and hotspot temperature sensitivity). From bottom to top, first with up to 30 (or 20) % by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally $\geq 90$ mol %, or $\geq 95$ mol % or $\geq 99$ mol %.

However, the performance of the partial oxidation of acrolein to acrylic acid may also be carried out with the catalysts described, for example, in a two-zone multiple catalyst tube fixed bed reactor as described in DE-A 199 10 508. For the acrolein conversion, the above statements apply. Also in the case in which an acrolein partial oxidation as described above is carried out as the second reaction stage of a two-stage propylene partial oxidation to acrylic acid in a two-zone multiple catalyst tube fixed bed reactor, the charge gas mixture (starting reaction gas mixture) will appropriately be obtained directly by using the product gas mixture of the partial oxidation directed to the first step (propylene→acrolein) (if appropriate after indirect or direct (for example by supplying secondary oxygen) intermediate cooling thereof (as has already been described above). The oxygen required for the acrolein partial oxidation is preferably added in the form of pure molecular oxygen (if appropriate also in the form of air or in the form of a mixture of molecular oxygen and an inert gas having an inert gas fraction of preferably $\leq 50\%$ by volume, more preferably s 40% by volume, or $\leq 30\%$ by volume, or $\leq 20\%$ by volume, even better $\leq 10\%$ by volume, or $\leq 5\%$ by volume, or $\leq 2\%$ by volume) and, for example, added directly to the product gas mixture of the first step of the two-stage partial oxidation (propylene→acrolein). However, it may also, as already described, already be present in the starting reaction gas mixture for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant loading on the catalyst bed, as is quite generally the case, preference is given to cocurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input temperature and their output temperature is generally $\leqq 5°$ C. As already mentioned, both steps of the partial oxidation of propylene to acrylic acid may also be implemented in one reactor over one charge, as described in DE-A 101 21 592.

It should also be mentioned here that a portion of the reaction gas B starting mixture for the first step ("propylene→acrolein") may be residual gas coming from separation zone II.

For the sake of completeness, it should be emphasized here that fresh propane may be metered additionally into both the charge gas mixture for the first oxidation stage and the charge gas mixture for the second oxidation stage, or else only one of the two. It is not preferred in accordance with the invention, but it may be favorable in some cases, in order to rule out ignitability of the charge gas mixtures.

Overall, a tube bundle reactor within which the catalyst charge changes appropriately along the individual catalyst tubes with completion of the first reaction step (such two-stage propylene partial oxidations in a single reactor are taught, for example, by EP-A 911 313, EP-A 979 813, EP-A 990 636 and DE-A 28 30 765) forms the simplest implementation form of two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert material bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first oxidation zone. The reaction temperature in the first reaction stage (propylene→acrolein) is generally from 300 to 450° C., preferably from 320 to 390° C. The reaction temperature in the second reaction stage (acrolein→acrylic acid) is generally from 200 to 370° C., frequently from 220 to 330° C. The reaction pressure in both oxidation zones is appropriately from >1 to 4 bar, advantageously from 1.3 to 3 bar. The loading (l(STP)/l·h) on the oxidation catalysts of reaction gas in both reaction stages is frequently from 1500 to 2500 l (STP)/l·h or to 4000 l (STP)/l·h. The loading of propylene or acrolein may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry has an advantageous effect on the kinetics of the particular gas phase partial oxidation and on the catalyst lifetime.

In principle, it is also possible to realize the heterogeneously catalyzed gas phase partial oxidation of propylene to acrylic acid to be carried out in accordance with the invention in a single one-zone tube bundle reactor as follows. Both reaction steps proceed in an oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon oxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (this is less preferred in accordance with the invention), either pure molecular oxygen or molecular oxygen diluted with inert gas such as $CO_2$, CO, noble gases, $N_2$ and/or saturated hydrocarbons. Preferably in accordance with the invention, the oxygen source comprises $\leqq 50\%$ by volume, preferably $\leqq 40\%$ by volume, more preferably $\leqq 30\%$ by volume, even more preferably $\leqq 20\%$ by volume, better s 10% by volume or $\leqq 5\%$ by volume, or $\leqq 2\%$ by volume of gases other than molecular oxygen.

Useful materials for the inert shaped diluent bodies in the catalyst beds for the two oxidation stages are those which have also been recommended for the dilution of the catalyst beds in reaction zone A.

In the process according to the invention, metering of, for example, cold oxygen source to the product gas mixture of the first partial oxidation stage can also bring about cooling thereof by a direct route before it is used further as a constituent of a starting reaction gas mixture for the second partial oxidation stage.

Advantageously in accordance with the invention, the partial oxidation of acrolein to acrylic acid is effected as described in EP-A 1 159 246 and most preferably as described in WO 04/085365 and in WO 04/085370. However, preference is given in accordance with the invention to using, as the starting reaction gas mixture comprising acrolein, a starting reaction gas mixture which is the product gas mixture of an inventive first-stage partial oxidation of propylene to acrolein, which has if appropriate been supplemented with sufficient secondary air that the ratio of molecular oxygen to acrolein in the resulting starting reaction gas mixture is in each case from 0.5 to 1.5. The documents EP-A 1 159 246, WO 04/08536 and WO 04/085370 are considered to be an integral part of this document.

In other words, the inventive partial oxidation of acrolein to acrylic acid can be carried out with increased acrolein loading advantageously over a fixed catalyst bed which has at least two temperature zones.

Overall, a two-stage partial oxidation of propylene to acrylic acid will preferably be carried out as described in EP-A 1 159 248 or in WO 04/085367 or WO 04/085369.

The product gas B which leaves the partial oxidation to be carried out in accordance with the invention (after the first and/or the second oxidation stage) comprises substantially acrolein or acrylic acid or a mixture thereof as the target product, unconverted propane, if appropriate molecular hydrogen, steam (formed as a by-product and/or used additionally as a diluent gas), any unconverted molecular oxygen (with a view to the lifetime of the catalysts used, it is typically favorable when the oxygen content in the product gas mixture of both partial oxidation stages is, for example, still from at least 1.5 to 4% by volume), and also other by-products or secondary components having higher and lower boiling points than water (for example CO, $CO_2$, lower aldehydes, lower alkanecarboxylic acids (e.g. acetic acid, formic acid and propionic acid), maleic anhydride, benzaldehyde, aromatic carboxylic acids and aromatic carboxylic anhydrides (e.g. phthalic anhydride and benzoic acid), in some cases further hydrocarbons, for example $C_4$ hydrocarbons (e.g. butene-1 and possibly other butenes), and in some cases further inert diluent gases, for example $N_2$). Useful processes for removing target product present in product gas B, which is generally accompanied simultaneously by removal of water and secondary components having higher boiling points than water for the process according to the invention in the second separation zone II are in principle all processes known in this regard in the prior art. An essential feature of these processes is that the target product is converted from the gaseous to the condensed phase, for example by absorptive and/or condensative measures, and the condensates or absorbates are subsequently worked up by extractive, distillative, crystallative, and/or desorptive measures for the purpose of further target product removal. Together with the target product and/or following the conversion of the target product to the condensed phase, these processes typically also convert steam and secondary components having higher boiling points than water present in reaction gas B to the condensed phase and hence remove them (preferably in accordance with the invention, an amount of steam is converted in separation zone II to the condensed phase which is at least 70 mol %, preferably at least 80 mol %, better at least 90 mol % and more preferably at least 95 mol % of the amount of steam formed in reaction zone B (or more preferably of the entire amount present in product gas B)).

Useful absorbents include, for example, water, aqueous solutions and/or organic solvents (for example mixtures of diphenyl and diphenyl ether, or of diphenyl, diphenyl ether and o-dimethyl phthalate). This "condensation" (removal) of target product, water and secondary components having higher boiling points than water normally leaves a residual gas which is not converted to the condensed phase and comprises constituents of product gas B which have a lower boiling point than water and are comparatively difficult to condense. These are typically those components in particular whose boiling point at standard pressure (1 bar) is $\leq -30°$ C. (their total content in residual gas is generally $\geq 60\%$ by volume, frequently $\geq 70\%$ by volume, in many cases $\geq 80\%$ by volume, but usually $\leq 90\%$ by volume). These include primarily unconverted propane, carbon dioxide, any unconverted propylene, any unconverted molecular oxygen, if appropriate molecular hydrogen, and other secondary components having lower boiling points than water, for example CO, ethane, methane, in some cases $N_2$, in some cases noble gases (e.g. He, Ne, Ar etc.). To a slight extent, the residual gas may also comprise acrylic acid, acrolein and/or $H_2O$. Preferably in accordance with the invention, the residual gas comprises $\leq 10\%$ by volume, advantageously $\leq 5\%$ by volume and particularly advantageously $\leq 3\%$ by volume of steam. This afore-mentioned residual gas normally forms (based on the amount of propane present therein) at least the majority (typically at least 80% or at least 90% or at least 95% or more) of the residual gas formed in the second separation zone II and is referred to in this document as (main) residual gas.

Especially when the target product is condensed by absorbing by means of one organic solvent, at least a second residual gas comprising unconverted propane and any unconverted propylene is generally obtained in separation zone II (based on propane present therein, its amount in comparison to the amount of (main) residual gas is normally substantially lower (generally $\leq 20\%$, usually $\leq 10\%$, or $\leq 5\%$, or $\leq 1\%$)). This is attributable to the condensed phase which forms also absorbing a certain amount of unconverted propane and any unconverted propylene.

In the further course of the extractive, distillative, crystallative and/or desorptive removal of the target product (within separation zone II) from the condensed phase, this unconverted propane and, if appropriate, propylene is normally recovered as a constituent of at least one further gas phase and is referred to in this document as (secondary) residual gas.

In this case, the sum of (main) residual gas and (secondary) residual gas forms the total amount of residual gas remaining in separation zone II. When no (secondary) residual gas is obtained in separation zone II, the (main) residual gas is automatically the total amount of residual gas (also known as (total) residual gas).

Preferably in accordance with the invention, the target product is converted from product gas B to the condensed phase by fractional condensation. This is especially true when the target product is acrylic acid. However, suitable processes for target product removal are in principle, for example, all of the absorptive and/or condensative processes for "target product condensation" and further workup of the "condensate" described in the documents DE-A 102 13 998, DE-A 22 63 496, U.S. Pat. No. 3,433,840 (processes described in the aforementioned documents are especially recommended for acrolein removal), EP-A 1 388 533, EP-A 1 388 532, DE-A 102 35 847, EP-A 792 867, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 1 041 062, EP-A 117 146, DE-A 43 08 087, DE-A 43 35 172, DE-A 44 36 243, DE-A 199 24 532, DE-A 103 32 758 and DE-A 199 24 533. An acrylic acid removal can also be undertaken as in EP-A 982 287, EP-A 982 289, DE-A 103 36 386, DE-A 101 15 277, DE-A 196 06 877, DE-A 197 40 252, DE-A 196 27 847, EP-A 920 408, EP-A 1 068 174, EP-A 1 066 239, EP-A 1 066 240, WO 00/53560, WO 00/53561, DE-A 100 53 086 and EP-A 982 288. Preference is given to removing as in FIG. 7 of WO/0196271 or as described in DE-A 10 2004 032 129 and their equivalent patents. Favorable removal methods are also the processes described in the documents WO 04/063138, WO 04/35514, DE-A 102 43 625 and DE-A 102 35 847. The further processing of crude acrylic acid obtained can be effected, for example, as described in the documents WO 01/77056, WO 03/041832, WO 02/055469, WO 03/078378 and WO 03/041833.

Typically, product gas B is fed to separation zone II with the working pressure with which it leaves reaction zone B.

A common feature of the above separating processes is (as already mentioned) that a stream of residual gas which comprises mainly those constituents of product gas B whose boiling point at standard pressure (1 bar) is lower than that of water and is usually $\leq -30°$ C. (i.e. the constituents which are difficult to condense or else volatile) normally remains, for example, at the top of the particular separating column comprising separating internals, into whose lower section product gas B is fed, for example, normally after preceding direct and/or indirect cooling thereof. However, residual gas may, for example, also still comprise constituents such as steam and acrylic acid.

In the lower section of the separating column, normally mainly the less volatile constituents of product gas B are obtained, including the particular target product, in condensed phase. Condensed aqueous phase is generally removed via side draw and/or via the bottom.

Typically, (main) residual gas comprises the following contents:
from 1 to 20% by volume of $H_2O$,
from 0 to 80% by volume of $N_2$,
from 10 to 90% by volume of propane,
from 0 to 20% by volume of $H_2$,
from 0 to 10% by volume of $O_2$,
from 1 to 20% by volume of $CO_2$ and
from $\geq 0$ to 5% by volume of CO.

The content of acrolein and acrylic acid is generally in each case <1% by volume.

Preferred (main) residual gases comprise:
from 1 to 5% by volume of $H_2O$,
from 10 to 80% by volume of propane,
from 0 to 5% by volume of $N_2$,
from 0 to 20% by volume of $H_2$,
from 1 to 10% by volume of $O_2$,
from 0 to 5% by volume of CO and
from 1 to 15% by volume of $CO_2$.

Typically, the residual gas leaves separation zone II in the process according to the invention with a pressure of $\geq 1$ bar and $\leq 3$ bar, preferably $\leq 2.5$ bar and generally $\leq 2$ bar. The temperature of the residual gas is normally $\leq 100°$ C., generally $\leq 50°$ C. (but typically $\geq 0°$ C.).

Appropriately from an application point of view, propane present in residual gas is absorbed in separation zone III appropriately at a pressure of from 5 to 50 bar, preferably from 10 to 25 bar. In a compression zone, the residual gas leaving separation zone II will normally be compressed to the pressure advantageous for the absorptive removal of the propane (this is advantageously effected in several stages). Preferably in accordance with the invention, a compression of the residual gas is carried out in a first compression stage with the aid of a multistage, for example, turbocompressor (radial compressor; for example of the MH4B type from Mannesmann DEMAG, Germany) (also referred to here as residual gas compressor) to a working pressure which corresponds essentially to that in reaction zone A (for example from 1.20 bar to 2.40 bar; in general, the compression is effected in the first compression stage to a pressure which is somewhat above the working pressure employed in reaction zone A). This heats the residual gas by, for example, up to 50° C. When it is not the entirety of residual gas that is subjected to propane absorption, the residual gas compressed as described is appropriately divided into two portions of identical composition. The proportion of the smaller portion may, for example, be up to 49%, preferably not more than up to 40%, or up to 30%, or up to 20%, or up to 10% of the total amount. It may also be $\geq 10\%$ and $\geq 49\%$ of the total amount.

This portion is available as residual gas cycle gas immediately for recycling into reaction zone A. The other portion is compressed further to the working pressure contemplated for the propane absorption. This can in principle be effected in just one further compression stage. However, advantageously in accordance with the invention, at least two further compression stages will be used for this purpose. This is because of the fact that the compression of a gas (as already noted in the first compression stage) is associated with a temperature increase thereof. Conversely, the decompression (expansion) of "propane-scrubbed" residual gas (which has, if appropriate, been subjected to an $H_2$ membrane removal) is associated with cooling thereof. When such a decompression is likewise carried out in several stages, an indirect heat exchange between heated, compressed, unscrubbed residual gas and cooled, expanded, "propane-scrubbed" residual gas can be undertaken before the next stage in each case. Such a heat exchange (which may be additionally supported by indirect air cooling of the compressed residual gas) can also be employed before a first expansion (as a consequence of the indirect heat exchange, condensations of any steam still present in the residual gas may occur therein). Advantageously from an application point of view, the aforementioned expansions are carried out in (advantageously likewise multistage) expansion turbines (this serves for the recovery of compression energy; in other words, the mechanical energy obtained in the expansion can in all cases (especially in the examples and comparative examples) be utilized either directly as an additional or main drive for one of the compressors and/or to generate electricity). Depending on the compression or expansion stage, the difference between entrance and exit pressure may, for example, be from 2 to 15 bar.

Before the propane present in the compressed residual gas, in a separation zone III, is taken up absorptively from the compressed residual gas into an organic solvent (scrubbed out of the compressed residual gas with the aid of an organic solvent (absorbent)), the compressed residual gas can be subjected in a further separation zone to another membrane separation, in order to remove at least a portion of any molecular hydrogen still present therein. Separating membranes suitable in this regard are, for example, aromatic polyimide membranes, for example those from UBE Industries Ltd. Among the latter, membrane types A, B-H, C and D in particular are useful. For such a removal, particular preference is given to the use of a UBE Industries Ltd. B-H polyimide membrane. The hydrogen permeation rate for $H_2$ for this membrane at 60° C. is $0.7 \cdot 10^{-3}$ [STP·cc/cm$^2$·sec·cm Hg]. For this purpose, the compressed residual gas can be passed through the membrane which generally has a tubular shape (but a plate or wound module are also useful) and which is permeable only to the molecular hydrogen. The molecular hydrogen thus removed may be used further in other chemical syntheses or at least partly recycled into reaction zone A (appropriately as a constituent of the reaction gas A charge gas mixture).

The membrane separation of molecular hydrogen from compressed residual gas is appropriate in accordance with the invention because it is carried out preferably likewise under high pressure (for example from 5 to 50 bar, typically from 10 to 25 bar). It is therefore advantageous in accordance with the invention to carry out a hydrogen membrane separation to be performed if appropriate from residual gas either immediately before the propane absorption (propane scrubbing) or, alternatively (and preferably in accordance with the invention), immediately after the propane scrubbing (propane absorption) of the residual gas, in order to twice utilize the pressure level which has been increased once in an advantageous manner. In addition to plate membranes, wound membranes or capillary membranes, tube membranes (hollow fiber membranes) in particular are useful for the hydrogen removal. Their internal diameter may, for example, be from a few μm to a few mm. For this purpose, analogously to the tubes of a tube bundle reactor, for example, a bundle of such tube membranes is cast into one plate in each case at each end of the tube. Outside the tube membrane, reduced pressure (<1 bar) preferably prevails. The residual gas under elevated pressure (or of "propane-scrubbed" residual gas) is conducted toward one of the two plate ends and forced through the tube interior to the tube outlet present at the opposite plate end. Along the flow path thus defined in the tube interior, molecular hydrogen is released outward through the $H_2$-permeable membrane.

The performance of the absorption of the propane (propylene unconverted in the course of the partial oxidation in reaction zone B is generally absorbed together with the propane) from the remaining residual gas is essentially subject to no restrictions at all. A simple means for this purpose consists, for example, in contacting the remaining residual gas (which, appropriately in accordance with the invention, has a temperature of from 10 to 100° C., preferably from 10 to 70° C.) at a pressure of from 5 to 50 bar, preferably from 10 to 25 bar, with an organic solvent (preferably hydrophobic) whose temperature is advantageously from 0 to 100° C., preferably from 20 to 50° C., or to 40° C., and in which propane and propylene are absorbed (appropriately preferentially over the other constituents of the remaining residual gas) (for example by simply passing it through).

For example, subsequent desorption (flash evaporation), rectification and/or stripping with a gas which behaves inertly with respect to reaction zone A (for example $N_2$) and/or is required as a reactant in this reaction zone (for example air or another mixture of molecular oxygen and inert gas; preferably steam or a mixture of steam and molecular oxygen, or a mixture of steam and air) can remove the propane and, if appropriate, propylene in a mixture from the absorbate in a separation zone IV, which can be recycled as propane-comprising feed stream into reaction zone A.

Suitable absorbents for the above-described absorptive removal are in principle all absorbents which are capable of absorbing propane and propylene. The absorbent is preferably an organic solvent which is hydrophobic and/or high-boiling. Advantageously, this solvent has a boiling point (at a standard pressure of 1 bar) of at least 120° C., preferably of at least 180° C., preferentially of from 200 to 350° C., in particular from 250 to 300° C., more preferably from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not comprise any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin-distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols comprising from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyl-diphenylmethane and its isomers, 2-methyl-2'-benzyldiphenylmethane, 2-methyl-4'-benzyldiphenylmethane and 4-methyl-2'-benzyldiphenylmethane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example from Bayer Aktiengesellschaft). Frequently, this solvent mixture comprises a solvent such as dimethyl phthalate added in an amount of from 0.1 to 25% by weight based on the entire solvent mixture. Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent is ≦300 g/mol. Also suitable are the paraffin oils, described in DE-A 33 13 573, having from 8 to 16 carbon atoms. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type. If they comprise a small residual aromatics content, this may, prior to the use described, advantageously be reduced by rectification and/or adsorption and be lowered to values significantly below 1000 ppm by weight. Further suitable commercial products are n-paraffin ($C_{13}$-$C_{17}$) or Mihagol®5 from Erdbl-Raffinerie-Emsland GmbH, LINPAR®14-17 from CONDEA Augusta S.p.A. (Italy) or SASOL Italy S.p.A., normal paraffins (heavy) $C_{14}$-$C_{18}$ from SLOVNAFT in Slovakia.

The contents (reported in area percent of gas chromatography analysis) in the aforementioned products of linear hydrocarbons are typically:

total $C_9$ to $C_{13}$: less than 1%; $C_{14}$: 30 to 40%; $C_{15}$: 20 to 33%; $C_{16}$: 18 to 26%; $C_{17}$: Up to 18%; C, 18: <2%.

A typical composition of the product from SASOL is:

$C_{13}$: 0.48%; $C_{14}$: 39.8%; $C_{15}$: 20.8%; $C_{16}$: 18.9%; $C_{17}$: 17.3%; $C_{18}$: 0.91%; C: 0.21%.

A typical composition of the product from Haltermann is:

$C_{13}$: 0.58%; $C_{14}$: 33.4%; $C_{15}$: 32.8%; $C_{16}$: 25.5%; $C_{17}$: 6.8%; $C_{\geq 18}$: <0.2%.

In continuous operation, the composition of the absorbent will change correspondingly as a result of the process.

The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000 $m^2/m^3$, or to 750 $m^2/m^3$, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and, if appropriate, propylene may be removed from the absorbent (from the absorbate) by stripping, flash evaporation (flashing) and/or distillation (rectification).

The propane and propylene are preferably removed from the absorbent by stripping and/or desorption. The desorption may be carried out in a customary manner by means of a pressure and/or temperature change, for example at a pressure of from 0.1 to 10 bar, or from 1 to 5 bar, or from 1 to 3 bar, and a temperature of from 0 to 200° C., in particular from 20 to 100° C., more preferably from 30 to 70° C., especially preferably from 30 to 50° C. A stripping gas preferred for the stripping is steam. A useful alternative is molecular nitrogen or a mixture of molecular nitrogen and steam. However, carbon dioxide or mixtures thereof with steam and/or nitrogen are also stripping gases suitable in accordance with the invention. Particularly suitable for the stripping are also bubble columns with and without internals.

The propane and, if appropriate, propylene can also be removed from the absorbent (from the absorbate) by means of a distillation or rectification, in which case the columns familiar to the person skilled in the art and having structured packings, random packings or corresponding internals may be used. Possible conditions in the distillation or rectification are a pressure of from 0.01 to 5 bar, or from 0.1 to 4 bar, or from 1 to 3 bar, and a temperature (in the bottom) of from 50 to 300° C., in particular from 150 to 250° C.

Before it is used to charge reaction zone A, a propane cycle gas obtained from the absorbate by stripping can be sent to a further process stage in separation zone IV, in order, for example, to reduce the losses of entrained absorbent (for example separation in demisters and/or depth filters) and thus to protect the reaction zone simultaneously from absorbent. Such a removal of the absorbent can be effected by all process variants known to those skilled in the art. An example of an embodiment of such a removal preferred in the process according to the invention is the quenching of the exit stream from the stripping apparatus with water. In this case, the absorbent is washed out of this laden exit stream with water and the exit stream is simultaneously laden with water. This washing, i.e. the quenching, can be effected, for example, at the top of a desorption column by means of a liquid collecting tray, by counterspraying of water or in a dedicated apparatus. To promote the separating effect, it is possible to install internals which increase the quench surface area in the quench chamber, as are known to those skilled in the art from rectifications, absorptions and desorptions.

A decompression of the absorbate comprising the propane (and if appropriate propylene) to the pressure appropriate for the removal of propane (and if appropriate propylene) can be performed in the process according to the invention, for example, by means of a valve or by means of an inverse pump. The mechanical energy released in the case of the inverse pump is, appropriately in accordance with the invention, also used to recompress absorbent freed of propane (and if appropriate propylene) (for example in the desorption column or in the stripping column). Generally, absorbate freed of propane can be reused as absorbent (appropriately in accordance with the invention, recompressed to the absorption pressure by means of a pump) to remove propane from residual gas in separation zone III.

Particularly advantageously in accordance with the invention, the propane is removed from the absorbate in separation zone IV at a pressure of from 1.5 or 2 to 5 bar, preferably from >2 to 5 bar, more preferably from 2.5 to 4.5 bar and most preferably from 3 to 4 bar.

A propane removal from the absorbate at the aforementioned working pressures is very particularly advantageous because propane cycle gas obtained at these working pressures can be recycled directly into reaction zone A. Such propane cycle gas can be used as the motive jet for a dehydrogenation cycle gas flow by the jet pump principle according to the teaching of DE-A 102 11 275. Appropriately in accordance with the invention, the propane cycle gas is, appropriately in accordance with the invention, heated to temperatures appropriate to reaction zone A by indirect heat exchange with hot reaction gas A and/or hot product gas A beforehand.

Typical contents of propane cycle gases obtained from the propane-comprising absorbate by desorption and/or stripping by means of steam in separation zone IV may, in the process according to the invention, be as follows:
from 80 to 99.99 mol % of propane,
from 0 to 5 mol % of propylene, and
from 0 to 20 mol % of $H_2O$.
In many cases, the contents of propane cycle gas are:
from 80 to 99 mol % of propane,
from 1 to 4 mol % of propylene, and
from 2 to 15 mol % of $H_2O$.

In the case that, aside from fresh propane (as a constituent of crude propane) and propane cycle gas and, if appropriate, dehydrogenation cycle gas, (appropriately compressed) residual gas cycle gas and/or a(nother) molecular oxygen-comprising gas is/are additionally fed to reaction zone A, the crude propane and the residual gas cycle gas and/or the molecular oxygen-comprising gas are, appropriately from an application point of view, mixed beforehand to give a first gas mixture and this first gas mixture (preferably after it has been heated by indirect heat exchange with hot reaction gas A and/or product gas A) is mixed with propane cycle gas or a mixture thereof with dehydrogenation cycle gas (preferably likewise after corresponding heating by indirect heat exchange with hot reaction gas A and/or product gas A) and the resulting gas mixture is conducted into reaction zone A as reaction gas A charge gas mixture. Advantageously, molecular hydrogen is also added to the resulting gas mixture before it is fed into reaction zone A as reaction gas A charge gas mixture.

The requirement for molecular oxygen-comprising gas in the process according to the invention is, appropriately from an application point of view, taken (covered) from a common source.

According to the invention, the crude propane is appropriately evaporated by means of condensate obtained in separation zone II (for example acid water) by indirect heat exchange (the condensate cooled in doing so may be used for direct cooling in separation zone II in order to obtain new condensate). Alternatively, other liquid phase (which appropriately has a temperature of from 20 to 40° C., preferably from 25 to 35° C.) may also be used as the heat carrier for the indirect heat exchange for the purpose of evaporating crude propane. To further heat the crude propane, indirect heat exchange with hot steam (which may be available, for example, at 5 bar and 152° C.), which is typically obtained plentifully as a by-product in the process according to the invention (for example in the course of removal of the process heat obtained in the course of the partial oxidation), is generally employed.

If required, a small amount of absorbent is discharged continuously from separation zone IV and replaced by fresh absorbent. The discharged absorbent can be worked up by rectification to give fresh absorbent. The residual gas which has been decompressed as described, "propane-scrubbed" beforehand and then, if appropriate, subjected to a membrane hydrogen removal is generally sent to residue incineration (offgas incineration). It is also possible for high boilers removed in separation zone II and aqueous condensates (for example acid water) formed in separation zone II and, if appropriate, between separation zone II and separation zone III to be conducted into this incineration which is, if appropriate, supported by feeding natural gas and performed using air as the source for combustion oxygen. The hot offgas of this incineration is typically used in indirect heat exchange with water to generate steam and then generally released into the atmosphere. Normally, it is composed exclusively of molecular oxygen, molecular nitrogen, molecular hydrogen and carbon dioxide. Finally, it should be emphasized that whenever condensed phases comprising acrylic acid and/or acrolein occur in the process according to the invention, the same polymerization inhibitor is added. Useful such polymerization inhibitors are in principle all known process inhibitors. Particularly suitable in accordance with the invention are, for example, phenothiazine and the methyl ether of hydroquinone. Presence of molecular oxygen increases the effectiveness of the polymerization inhibitors.

Acrolein obtained by the process according to the invention can be converted to the acrolein subsequent products mentioned in the documents U.S. Pat. Nos. 6,166,263 and 6,187,963. These include 1,3-propanediol, methionine, glutaraldehyde and 3-picoline.

Preference is given to processes according to the invention which have the maximum working pressure in separation zone III.

Advantageously, for the working pressures P (determined in each case at the entrance into the particular zone) in the different zones of the process according to the invention, the following correlations (relationships) apply:

$$P_{reaction\ zone\ A} > P_{separation\ zone\ I} >$$
$$P_{reaction\ zone\ B} > P_{separation\ zone\ I} <$$
$$P_{separation\ zone\ III} > P_{separation\ zone\ IV} >$$
$$P_{reaction\ zone\ A}.$$

although separation zone I can also be dispensed with.

It is also advantageous for the process according to the invention to keep the temperature of reaction gases A, especially when they comprise molecular oxygen, at values of $\leq 460°$ C., preferably $\leq 440°$ C. outside catalyst and/or inert beds, in order thus to minimize undesired combustion reactions and thermal decompositions, especially of propane.

EXAMPLES AND COMPARATIVE EXAMPLES

I. Long-term Operation of a Heterogeneously Catalyzed Two-stage Partial Oxidation of Propylene to Acrylic Acid in the Absence and in the Presence of Molecular Hydrogen
A) General experimental setup of the reaction apparatus
Reactor for the First Oxidation Stage The reactor consisted of a jacketed cylinder of stainless steel (cylindrical guide tube surrounded by a cylindrical outer vessel). The wall thicknesses were always from 2 to 5 mm. The internal diameter of the outer cylinder was 91 mm. The internal diameter of the guide tube was approx. 60 mm.

At the top and bottom, the jacketed cylinder was concluded by a lid and base respectively.

The catalyst tube (total length 400 cm, internal diameter 26 mm, external diameter 30 mm, wall thickness 2 mm, stainless steel) was accommodated in the guide tube of the cylindrical vessel such that it just protruded in each case through the lid and base at the upper and lower end thereof (in a sealed manner). The heat exchange medium (salt melt consisting of 53% by weight of potassium nitrate, 40% by weight of sodium nitrite and 7% by weight of sodium nitrate) was enclosed in the cylindrical vessel. In order to ensure very uniform thermal boundary conditions at the outer wall of the catalyst tube over the entire length of catalyst tube within the cylindrical vessel (400 cm) the heat exchange medium was pumped in circulation by means of a propeller pump.

An electrical heater attached to the outer jacket regulated the temperature of the heat exchange medium to the desired level. Otherwise, there was air cooling.

Reactor charge: Viewed over the first-stage reactor, the salt melt and the charge gas mixture of the first-stage reactor were conducted in cocurrent. The charge gas mixture entered the first-stage reactor at the bottom. It was conducted into the reaction tube with a temperature of 165° C. in each case.

The salt melt entered the cylindrical guide tube at the bottom with a temperature $T^{in}$ and left the cylindrical guide tube at the top with a temperature $T^{out}$ which was up to 2° C. above $T^{in}$.

$T^{in}$ was adjusted so as to always give rise to a propylene conversion of 97.8±0.1 mol % in single pass at the outlet of the first oxidation stage.

Catalyst tube charge:

(from the bottom upward) Section A: length 90 cm
  Upstream bed of steatite spheres of diameter 4-5 mm.
Section B: length 100 cm
  Catalyst charge of a homogeneous mixture of 30% by weight of steatite rings of geometry 5 mm×3 mm×2 mm (external diameter×length×internal diameter) and 70% by weight of unsupported catalyst from section C.
Section C: length 200 cm
  Catalyst charge of annular (5 mm×3 mm×2 mm=external diameter×length×internal diameter) unsupported catalyst according to example 1 of DE-A 100 46 957 (stoichiometry: $[Bi_2W_2O_9 x2WO_3]_{0.5}$ $[Mo_{12}CO_{5.5}Fe_{2.94}Si_{1.59}K_{0.08}O_x]_1$).
Section D: length 10 cm
  Downstream bed of steatite rings of geometry 7 mm×3 mm×4 mm (external diameter×length×internal diameter)

Intermediate Cooling And Intermediate Oxygen Feeding (Pure O$_2$ as Secondary Gas)

For the purpose of intermediate cooling (indirectly by means of air), the product gas mixture leaving the first fixed bed reactor was conducted through a connecting tube (length 40 cm, internal diameter 26 mm, external diameter 30 mm, wall thickness 2 cm, stainless steel, wound around by 1 cm of insulating material) which was mounted centrally to a length of 20 cm, charged with an inert bed of steatite rings of geometry 7 mm×3 mm×4 mm (external diameter×length×internal diameter) and was flanged directly onto the first-stage catalyst tube.

The product gas mixture always entered the connecting tube at a temperature of $>T^{in}$ (first stage) and left it with a temperature above 200° C. and below 270° C.

At the end of the connecting tube, molecular oxygen at the pressure level of the product gas mixture was metered into the cooled product gas mixture. The resulting gas mixture (charge gas mixture for the second oxidation stage) was conducted directly into the second-stage catalyst tube to which the abovementioned connecting tube was likewise flanged by its other end. The amount of molecular oxygen metered in was such that the molar ratio of $O_2$ present in the resulting gas mixture to acrolein present in the resulting gas mixture was 1.3.

Reactor for the Second Oxidation Stage

A catalyst tube fixed bed reactor was used which was of identical design to that for the first oxidation stage. Salt melt and charge gas mixture were conducted in cocurrent viewed over the reactor. The salt melt entered at the bottom, the charge gas mixture likewise. The entrance temperature $T^{in}$ of the salt melt was adjusted so as always to result in an acrolein conversion of 99.3±0.1 mol % in single pass at the outlet of the second oxidation stage. Tout of the salt melt was up to 2° C. above $T^{in}$.

The catalyst tube charge (from the bottom upward) was:

Section A: Length 70 cm
  Preliminary bed of steatite rings of geometry 7 mm×3 mm×4 mm (external diameter×length×internal diameter).

Section B: Length 100 cm
  Catalyst charge of a homogeneous mixture of 30% by weight of steatite rings of geometry 7 mm×3 mm×4 mm (external diameter×length ×internal diameter) and 70% by weight of coated catalyst from section C.

Section C: Length 200 cm
  Catalyst charge of annular (7 mm×3 mm×4 mm=external diameter×length×internal diameter) coated catalyst according to preparation example 5 of DE-A 10046928 (stoichiometry: $Mo_{12}V_3W_{1.2}Cu_{2.4}O_x$).

Section D: Length 30 cm
  Downstream bed of steatite spheres of diameter 4-5 mm.

B) Results achieved as a function of the composition of the charge gas mixture of the first oxidation stage (the propene loading was set to 150 l (STP)/l·h; the selectivity of acrylic acid formation was always ≧94 mol %).

a) The composition of the charge gas mixture for the first oxidation stage was substantially:
  7% by volume of propylene,
  12% by volume of $O_2$,
  20% by volume of $H_2$,
  5% by volume of $H_2O$ and
  56% by volume of $N_2$.

At the start of the reaction apparatus charged freshly with catalyst, the entrance temperatures were:
  $T^{in}$ (first oxidation stage): 320° C.
  $T^{in}$ (second oxidation stage): 268° C.

After an operating time of 3 months, the entrance temperatures were:
  $T^{in}$ (first oxidation stage): 330° C.
  $T^{in}$ (second oxidation stage): 285° C.

b) The composition of the charge gas mixture for the first oxidation stage was substantially:
  7% by volume of propylene,
  12% by volume of $O_2$,
  5% by volume of $H_2O$ and
  76% by volume of $N_2$.

At the start of the reaction apparatus charged freshly with catalyst, the entrance temperatures were:
  $T^{in}$ (first oxidation stage): 320° C.
  $T^{in}$ (second oxidation stage): 268° C.

After an operating time of 3 months, the entrance temperatures were:
  $T^{in}$ (first oxidation stage): 324° C.
  $T^{in}$ (second oxidation stage): 276° C.

II. First Illustrative Process for Preparing Acrylic Acid from Propane (a Steady Operating State is Described)

Reaction zone A consists of a shaft furnace reactor which has been designed as a tray reactor and configured adiabatically and has three fixed catalyst beds arranged successively in flow direction. The particular fixed catalyst bed is a bed, placed onto a stainless steel wire mesh, of (arranged in the sequence specified in flow direction) inert material (bed height: 26 mm; steatite spheres of diameter of from 1.5 to 2.5 mm) and a mixture of fresh dehydrogenation catalyst and steatite spheres (diameter from 1.5 to 2.5 mm) in a bed volume ratio of dehydrogenation catalyst: steatite spheres=1:3 (alternatively, it is, though, also possible at this point for the same amount of catalyst to be used undiluted).

Upstream of each fixed bed is disposed a static gas mixer. The dehydrogenation catalyst is a Pt/Sn alloy which has been promoted with the elements Cs, K and La in oxidic form and which has been applied to the outer and inner surface of $ZrO_2 \cdot SiO_2$ mixed oxide support extrudates (mean length (Gaussian distribution in the range from 3 mm to 12 mm with maximum at approx. 6 mm): 6 mm, diameter: 2 mm) in the element stoichiometry (mass ratio including support)
  $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 10219879).

The heterogeneously catalyzed partial propane dehydrogenation is carried out in the tray reactor described in straight pass with dehydrogenation cycle gas mode. The loading of the total amount of catalyst (calculated without inert material) of all trays with propane is 1500 l (STP)/l·h.

7.30 m³ (STP)/h of reaction gas A charge gas mixture (starting mixture; P=2.13 bar) are fed to the first catalyst bed in flow direction and have the following contents:
  propane 61.22% by volume,
  propylene 12.17% by volume,
  ethylene 0.86% by volume,
  methane 2.56% by volume,
  $H_2$ 3.78% by volume,
  $O_2$ 2.10% by volume,
  $H_2O$ 12.08% by volume,
  CO 0.38% by volume, and
  $CO_2$ 3.35% by volume.

The reaction gas A charge gas mixture is a mixture of a first (2.34 m³ (STP)/h) and a second (4.96 m³ (STP)/h) gas mixture which is obtained by combining the two gas mixtures by means of a static mixer. The first gas mixture has a temperature of 400° C. and a pressure of 2.13 bar and is composed of:
  1.19 m³ (STP)/h of compressed residual gas cycle gas (T=70° C., P=2.40 bar),
  1.05 m³ (STP)/h of crude propane which comprises propane (fresh propane) to an extent of >98% by volume (T=237° C., P=2.90 bar), and
  0.098 m³ (STP)/h of $O_2$ (T=139° C., P=2.33 bar, purity >99% by volume).

Indirect heat exchange in a first heat exchanger with product gas A conducted out of reaction zone A and in the direction of reaction zone B establishes the temperature of 400° C. The second gas mixture is composed of:
  3.68 m³ (STP)/h of dehydrogenation cycle gas (T=551° C., P=2.05 bar) and
  1.28 m³ (STP)/h of propane cycle gas (T=400° C., P=3.26 bar).

It has a pressure of 2.13 bar and a temperature of 506° C. Indirect heat exchange with the product gas A cooled to a temperature of 435° C. in the first heat exchanger establishes the temperature of the propane cycle gas. The dehydrogenation cycle gas flow is effected according to the jet pump principle (cf. DE-A 10211275), the propane cycle gas heated to 400° C. functioning as the motive jet.

The entrance temperature of the reaction gas A charge gas mixture and the bed height of the first catalyst bed flowed through by the reaction gas A charge gas mixture are adjusted such that reaction gas A leaves this catalyst bed with a temperature of 515° C. and a pressure of 2.11 bar with the following contents:

propane 55.8% by volume,
propylene 15.85% by volume,
ethylene 0.88% by volume,
methane 2.89% by volume,
$H_2$ 3.78% by volume,
$O_2$ 0% by volume,
$H_2O$ 15.5% by volume, and
$CO_2$ 3.67% by volume.

The leaving amount is 7.46 $m^3$ (STP)/h.

Beyond the first catalyst bed, 0.12 $m^3$ (STP)/h of molecular oxygen (purity >99% by volume) is metered into reaction gas A (T=139° C., P=2.33 bar). The metered addition is effected by throttling, so that the resulting pressure of the resulting reaction gas A is still 2.11 bar.

The bed height of the second catalyst bed is such that reaction gas A leaves the second catalyst bed with a temperature of 533° C. and a pressure of 2.08 bar with the following contents:

propane 49.2% by volume,
propylene 19.24% by volume,
ethylene 1.04% by volume,
methane 3.14% by volume,
$H_2$ 4.43% by volume,
$O_2$ 0% by volume,
$H_2O$ 17.98% by volume, and
$CO_2$ 3.52% by volume.

The leaving amount is 7.79 $m^3$ (STP)/h.

Upstream of the static mixer disposed upstream of the third catalyst bed, 0.13 $m^3$ (STP)/h of molecular oxygen (purity >99% by volume) is metered into this reaction gas A (T=139° C., throttled in at a pressure of 2.33 bar). The resulting pressure of the resulting reaction gas A is still 2.08 bar.

The bed height of the third catalyst bed is such that reaction gas A leaves the third catalyst bed as product gas A with a temperature of 551° C. and a pressure of 2.05 bar with the following contents:

propane 42.19% by volume,
propylene 22.79% by volume,
ethylene 1.14% by volume,
methane 3.42% by volume,
$H_2$ 5.28% by volume,
$O_2$ 0% by volume,
$H_2O$ 20.32% by volume, and
$CO_2$ 3.36% by volume.

The leaving amount is 8.17 $m^3$ (STP)/h.

Product gas A is divided into two portions of identical composition by a flow divider. The first portion is 3.68 $m^3$ (STP)/h and the second portion is 4.49 $m^3$ (STP)/h. The first portion is recycled into reaction zone A as a constituent of the reaction gas A charge gas mixture. For the purpose of dehydrogenation cycle gas flow of the first portion, the propane cycle gas heated as described is used as the motive jet to operate a jet pump, the conveying direction of the motive jet decompressed through a motive nozzle via a mixing zone and a diffuser pointing in the direction of the entrance to reaction zone A, and the suction nozzle pointing in the direction of the first flow portion of product gas A, and the "suction nozzle—mixing zone—diffuser" connection forming the sole connecting line between the first portion of product gas A to be recycled and the access to reaction zone A. The second portion of product gas A is conducted out of reaction zone A and first cooled from 551° C. to 435° C. by a first indirect heat exchange with the first gas mixture, composed of compressed residual gas cycle gas, crude propane and molecular oxygen, involved in the reaction gas A starting mixture (charge gas mixture). As this is done, the working pressure in the product gas A conducted out of reaction zone A falls from 2.05 bar to 1.95 bar. At the same time, the first gas mixture is heated from 164° C. to 506° C. and suffers a pressure drop of from 2.40 bar to 2.13 bar.

In a downstream second indirect heat exchange with propane cycle gas from separation zone IV, product gas A is cooled from 435° C. to 335° C. As this is done, the working pressure in product gas A falls to 1.94 bar. Conversely, the temperature of the propane cycle gas rises from 69° C. to 400° C.

Subsequently, 0.76 $m^3$ (STP)/h of steam is removed by condensation from the product gas A cooled to 335° C. To this end, the product gas A cooled to 335° C. is first conducted in indirect heat exchange to 3.73 $m^3$ (STP)/h of product gas A* (T=40° C., P=1.68 bar) from which the appropriate amount of steam has already been removed by condensation, and thus cooled to 108° C. The temperature of product gas A* simultaneously increases to 305° C. In a downstream air cooler, product gas A (T=108° C., P=1.94 bar) is cooled to 54° C. by indirect heat exchange with external air (the working pressure of product gas A falls to 1.73 bar) and thereafter already has biphasicity.

Direct cooling with sprayed aqueous condensate which has been cooled (to 29° C.) and removed beforehand from product gas A by appropriate direct cooling removes the aforementioned amount of steam from product gas A by condensation to obtain a product gas A* (P=1.68 bar, T=40° C., 3.73 $m^3$ (STP)/h). This is heated to 305° C. as described above. 1.39 $m^3$ (STP)/h of molecular oxygen (purity >99% by volume, T=139° C., P=2.33 bar) are then throttled into the product gas A*. This forms a reaction gas B starting mixture (charge gas mixture) which has a temperature of 288° C. and a working pressure of 1.63 bar.

The reaction gas B starting mixture (charge gas mixture) has the following contents:

propane 37.01% by volume,
propylene 19.99% by volume,
ethylene 0.99% by volume,
methane 2.99% by volume,
$H_2$ 4.63% by volume,
$O_2$ 26.79% by volume,
$H_2O$ 3.14% by volume, and
$CO_2$ 2.95% by volume.

This is used to charge reaction zone B.

The first oxidation stage in flow direction of reaction gas B is a multitube reactor having two temperature zones. The reaction tubes are configured as follows: V2A steel; external diameter 30 mm, wall thickness 2 mm, internal diameter 26 mm, length 350 cm. From the top downward, the reaction tubes are charged as follows:

Section 1: Length 50 cm
   Steatite rings of geometry 7 mm×7 mm×4 mm (external diameter×length×internal diameter) as an upstream bed.
Section 2: Length 140 cm
   Catalyst charge of a homogeneous mixture of 20% by weight (alternatively 30% by weight) of steatite rings of geometry 5 mm×3 mm×2 mm (external diameter×length×internal diameter) and 80% by weight (alternatively 70% by weight) of unsupported catalyst from section 3.

Section 3: Length 160 cm
  Catalyst charge of annular (5 mm×3 mm×2 mm=external diameter×length×internal diameter) unsupported catalyst according to example 1 of DE-A 100 46 957 (stoichiometry: $[Bi_2W_2O_9\text{-}2WO_3]_{0.5}[Mo_{12}CO_{5.5}Fe_{2.94}Si_{1.59}K_{0.08}O_x]_1)$.
  Alternatively, it is also possible here to use one of the catalysts EUC 1 to EUC 11 from Research Disclosure No. 497012 of Aug. 29, 2005 (the specific surface areas of the active compositions are reported there mistakenly in $cm^2/g$; however, the correct dimension is $m^2/g$ with the same numerical value).

From the top downward, the first 175 cm are thermostated by means of a salt bath A pumped in countercurrent to reaction gas B. The second 175 cm are thermostated by means of a salt bath B pumped in countercurrent to reaction gas B.

The second oxidation stage in flow direction of reaction gas B is likewise a multitube reactor having two temperature zones. The reaction tubes are charged from the top downward as follows:

Section 1: Length 20 cm
  Steatite rings of geometry 7 mm×7 mm×4 mm (external diameter×length×internal diameter) as an upstream bed.
Section 2: Length 90 cm
  Catalyst charge of a homogeneous mixture of 25% by weight (alternatively 30% by weight) of steatite rings of geometry 7 mm×3 mm×4 mm (external diameter×length×internal diameter) and 75% by weight (alternatively 70% by weight) of coated catalyst from section 4.
Section 3: Length 50 cm
  Catalyst charge of a homogeneous mixture of 15% by weight (alternatively 20% by weight) of steatite rings of geometry 7 mm×3 mm×4 mm (external diameter×length×internal diameter) and 85% by weight (alternatively 80% by weight) of coated catalyst from section 4.
Section 4: Length 190 cm
  Catalyst charge of annular (7 mm×3 mm×4 mm=external diameter×length×internal diameter) coated catalyst according to preparation example 5 of DE-A 100 46 928 (stoichiometry: $Mo_2V_3W_{1.2}Cu_{2.4}O_x$).

From the top downward, the first 175 cm are thermostated by means of a salt bath C pumped in countercurrent to the reaction gas. The second 175 cm are thermostated by means of a salt bath D pumped in countercurrent to the reaction gas.

In both oxidation stages, the salt baths are each conducted in a meandering manner around the reaction tubes by virtue of deflecting plates.

Between the two oxidation stages is disposed a tube bundle heat exchanger cooled by means of salt bath, with which the product gas of the first oxidation stage can be cooled. Upstream of the entry into the second oxidation stage is disposed a valve for the supply of molecular oxygen (purity >99% by volume).

The propylene loading on the catalyst charge of the first oxidation stage is selected to be 130 l(STP)/l·h. The salt melts (53% by weight of $KNO_3$, 40% by weight of $NaNO_2$, 7% by weight of $NaNO_3$) have the following entrance temperatures:
  $T_A$=324° C. $T_B$=328° C.
  $T_C$=265° C. $T_D$=269° C.

Sufficient molecular oxygen (139° C., 2.33 bar) is metered (throttled) into the product gas mixture of the first oxidation stage that the molar $O_2$: acrolein ratio in the resulting charge gas mixture for the second oxidation stage is 0.73. The acrolein loading on the catalyst charge of the second oxidation stage is 110 l(STP)/l·h. The pressure at the entrance to the second oxidation stage is 1.57 bar. Reaction gas B leaves the intermediate cooler with a temperature of 260° C. and the entrance temperature of the charge gas mixture into the second oxidation stage is 256° C. The product gas mixture of the first oxidation stage has the following contents:
  acrolein 16.84% by volume,
  acrylic acid 1.13% by volume,
  propane 36.88% by volume,
  propylene 0.99% by volume,
  methane 2.99% by volume,
  $H_2$ 4.61% by volume,
  ethylene 0.99% by volume,
  $O_2$ 4.32% by volume,
  $H_2O$ 23.96% by volume,
  CO 0.847% by volume, and
  $CO_2$ 4.93% by volume Before entry into the aftercooler, the temperature of the product gas of the first oxidation stage is 335° C.

The product gas mixture of the second oxidation stage (product gas B) has a temperature of 270° C. and a pressure of 1.55 bar, and also the following contents:
  acrolein 0.089% by volume,
  acrylic acid 17.02% by volume,
  acetic acid 0.46% by volume,
  propane 36.79% by volume,
  propylene 0.99% by volume,
  methane 2.98% by volume,
  ethylene 0.99% by volume,
  $H_2$ 4.59% by volume,
  $O_2$ 2.69% by volume,
  $H_2O$ 24.57% by volume,
  CO 1.35% by volume and
  $CO_2$ 5.91% by volume As described in WO 2004/035514, product gas B (5.15 $m^3$ (STP)/h) is fractionally condensed in a tray column (separation zone II).

As the first fuel, 13.7 g/h of high boilers (polyacrylic acids (Michael adducts), etc.) are fed to the residue incineration.

From the second collecting tray above the feed of product gas B into the tray column, 2.80 kg/h of a condensed crude acrylic acid are withdrawn which has a temperature of 15° C. and 96.99% by weight of acrylic acid. As described in WO 2004/035514, this is suspension-crystallized after addition of a small amount of water, the suspension crystals are separated from the mother liquor in hydraulic scrubbing columns and the mother liquor is recycled into the condensation column as described in WO 2004/035514. The purity of the washed suspension crystals is >99.87% by weight of acrylic acid and is suitable immediately for preparing water-"superabsorbing" polymers for use in the hygiene sector.

The amount of acid water condensate withdrawn from the third collecting tray above the feed of product gas B into the condensation column but not recycled into the condensation column is 1.10 kg/h, has a temperature of 33° C. and has the following contents:
  0.80% by weight of acrolein,
  4.92% by weight of acrylic acid,
  5.73% by weight of acetic acid and
  87.0% by weight of water.

It is likewise fed to the residue incineration (5.49 $m^3$ (STP)/h of air are fed into the residue incineration as the oxygen source).

At the top of the condensation column, 2.98 $m^3$ (STP)/h of residual gas leave separation zone II with a temperature of 33° C. and a pressure of 1.20 bar and the following contents:
  acrolein 0.03% by volume,
  acrylic acid 0.02% by volume,
  acetic acid 0.01% by volume,
  propane 63.7% by volume, propylene 1.72% by volume,
$H_2$ 6.90% by volume,
methane 5.16% by volume,
ethylene 1.72% by volume,
$O_2$ 4.68% by volume,
$H_2O$ 2.07% by volume,
CO 2.34% by volume and
$CO_2$ 10.18% by volume In the first compressor stage of a multistage radial compressor, the residual gas is compressed from 1.20 bar to 2.40 bar, in the course of which the temperature of the residual gas rises to 70° C. The compressed residual gas is then divided into two portions of identical composition. The first portion (1.19 m³ (STP)/h) is fed as (compressed) residual gas cycle gas to the formation of the charge gas mixture for reaction zone A. The other portion (1.79 m³ (STP)/h) is compressed from 2.40 bar to 6.93 bar in a second compressor stage. This heats it to 130° C.

In an indirect heat exchanger, it is cooled to 113° C. without condensate being formed (coolant is the "propane-scrubbed" residual gas (it is also referred to hereinafter as "offgas") which, after being heated from 30 to 86° C. in an indirect heat exchanger, is decompressed starting from 20 bar in the first expansion stage of a multistage expansion turbine and cooled at the same time). This heats the offgas (0.58 m³ (STP)/h). In a second expansion stage, the offgas is decompressed to 1.10 bar (it then has a temperature of 25° C.) and then fed to residue incineration.

In an indirect air cooler, the compressed residual gas (P=6.93 bar and T=113° C.) is cooled to 59° C. In a third compressor stage, it is compressed from 6.93 bar to 20 bar, which simultaneously heats it to 11 6° C.

In a downstream indirect heat exchanger, it is cooled to 107° C. (coolant is the "propane-scrubbed" residual gas which is heated at the same time from 30° C. to 86° C.) without condensate being formed. In a subsequent further indirect heat exchanger, the residual gas at 107° C. is cooled to 35° C. (coolant is surface water at approx. 25° C.; instead of surface water, it is always also possible in this document to use other cooling water); this condenses 29 g/h of water out of the residual gas. This aqueous condensate (which is preferably separated with droplet separators) is likewise sent to residue incineration and incinerated therein together with the other residues mentioned (with supply of 5.49 m³ (STP)/h of air, as already stated). The hot incineration gases are cooled to generate steam (52 bar, 267° C., 4.6 kg/h) and released into the environment.

The residual gas which now still comprises 1.75 m³ (STP)/h of propane (20 bar, 35° C.) are fed into the lower section of a column with random packing (separation zone III). At the top of this scrubbing column, 12.96 kg/h of technical tetradecane with an introduction temperature of 30° C. (P=20 bar), of the PKWF 4/7 af type from Haltermann, Germany, are introduced as absorbent (gas chromatography analysis by means of F/D detection gives rise to the following GC area % composition at the start (fresh):
n-tridecane 7.6%,
n-tetradecane 47.3%,
n-pentadecane 7.0%,
n-hexadecane 3.2%,
n-heptadecane 14.1% and
total residue 20.7%.

At the top of the scrubbing column, "propane-scrubbed" residual gas (offgas) escapes, which, at a pressure of 20 bar and a temperature of 30° C. and an amount of 0.58 m³ (STP)/h, has the following contents:
propane 1.97% by volume,
propylene 0.049% by volume,
methane 15.95% by volume,
ethylene 5.32% by volume,
$H_2$ 21.29% by volume,
$O_2$ 14.46% by volume,
$H_2O$ 0.82% by volume,
CO 7.23% by volume and
$CO_2$ 31.43% by volume.

This offgas is decompressed as described and subjected to indirect heat exchange and then fed to residue incineration or incinerated by means of a flare.

15.27 kg/h of absorbate which has a pressure of 20 bar and a temperature of 59° C. are withdrawn from the bottom of the "propane scrubbing column" which is neither externally heated nor cooled. It comprises 14.79% by weight of propane and 0.38% by weight of propylene.

Before the absorbate is conducted to the top of the downstream desorption column, it is heated to 69° C. in an indirect heat exchanger. The heat carrier used is the liquid effluent from the desorption column (12.96 kg/h) which has a temperature of 80° C. at a pressure of 3.26 bar and still comprises 0.09% by weight of dissolved propane. By means of a pump, it is compressed back to 20 bar, and, after indirect cooling with surface water (25° C.) to 30° C., it is recycled to the propane absorption at the top of the "propane scrubbing column".

After being heated to 69° C., the absorbate (for example in an inverse pump or by means of a valve) is decompressed to a pressure of 3.26 bar (the mechanical energy released in the case of the inverse pump is appropriately also used to recompress absorbent freed of propane in the desorption column (the liquid effluent of the desorption column)), and the biphasic mixture obtained is conducted into the desorption column at the top.

0.1 kg/h of steam is fed with a pressure of 5 bar and a temperature of 152° C. as stripping gas into the desorption column (likewise a column with random packing) from the bottom in countercurrent to the absorbate descending from the top of the desorption column.

Disposed in the desorption column is a heating coil through which steam of temperature 152° C., P=5.00 bar in an amount of 0.5 kg/h is likewise conducted in countercurrent to the steam ascending in the desorption column.

At the top of the desorption column, 1.28 m³ (STP)/h of propane cycle gas which have a temperature of 69° C. and a working pressure of 3.26 bar escape. After heating to 400° C. by indirect heat exchange with product gas A of temperature T=435° C., the propane cycle gas is used as the motive jet to operate the jet pump, with which the dehydrogenation cycle gas and the propane cycle gas are fed to the charging of reaction zone A with reaction gas A starting mixture.

The propane cycle gas has the following contents:
propane 88.45% by volume,
propylene 2.39% by volume, and
$H_2O$ 8.66% by volume.

III. Second Illustrative Process for Preparing Acrylic Acid from Propane (a Steady Operating State is Described)

Reaction zone A is a tray reactor as described under II. The heterogeneously catalyzed partial propane dehydrogenation is carried out in the tray reactor described in straight pass with dehydrogenation cycle gas mode. The loading of the total amount of catalyst (calculated without inert material) of all trays with propane is 1500 l (STP)/l·h.

8.23 m³ (STP)/h of reaction gas A charge gas mixture (starting mixture; P=1.84 bar) are fed to the first catalyst bed in flow direction and have the following contents:
propane 64.20% by volume,
propylene 16.0% by volume, methane 1.39% by volume,
ethylene 0.46% by volume,
H$_2$ 2.76% by volume,
O$_2$ 1.06% by volume, and
H$_2$O 13.13% by volume.

The reaction gas A charge gas mixture is a mixture of a first (1.15 m$^3$ (STP)/h) and a second (7.08 m$^3$ (STP)/h) gas mixture which is obtained by combining the two gas mixtures by means of a static mixer. The first gas mixture has a temperature of 450° C. and a pressure of 1.84 bar and is composed of:
1.06 m$^3$ (STP)/h of crude propane which comprises propane (fresh propane) to an extent of >98% by volume (T=237° C., P=2.90 bar), and
0.087 m$^3$ (STP)/h of O$_2$ (T=143° C., P=1.84 bar, purity >99% by volume).

Indirect heat exchange in a first heat exchanger with product gas A conducted out of reaction zone A and in the direction of reaction zone B establishes the temperature of 450° C.

The second gas mixture is composed of:
5.04 m$^3$ (STP)/h of dehydrogenation cycle gas (T=540° C., P=1.73 bar) and
2.04 m$^3$ (STP)/h of propane cycle gas (T=400° C., P=3.26 bar).

It has a pressure of 1.84 bar and a temperature of 486° C. Indirect heat exchange with the product gas A cooled to a temperature of 476° C. in the first heat exchanger establishes the temperature of the propane cycle gas. The dehydrogenation cycle gas flow is effected according to the jet pump principle (cf. DE-A 10211275), the propane cycle gas heated to 400° C. functioning as the motive jet.

The entrance temperature of the reaction gas A charge gas mixture and the bed height of the first catalyst bed flowed through by the reaction gas A charge gas mixture are adjusted such that reaction gas A leaves this catalyst bed with a temperature of 503° C. and a pressure of 1.81 bar with the following contents:
propane 60.7% by volume,
propylene 18.19% by volume,
methane 1.59% by volume,
ethylene 0.53% by volume,
H$_2$ 2.94% by volume,
O$_2$ 0% by volume, and
H$_2$O 15.0% by volume.

The leaving amount is 8.35 m$^3$ (STP)/h.

Beyond the first catalyst bed, 0.13 m$^3$ (STP)/h of molecular oxygen (purity >99% by volume) is metered into reaction gas A (T=143° C., P=2.40 bar). The metered addition is effected by throttling, so that the resulting pressure of the resulting reaction gas A is still 1.81 bar.

The bed height of the second catalyst bed is such that reaction gas A leaves the second catalyst bed with a temperature of 520° C. and a pressure of 1.78 bar with the following contents:
propane 54.2% by volume,
propylene 21.3% by volume,
methane 1.90% by volume,
ethylene 0.63% by volume,
H$_2$ 3.61% by volume,
O$_2$ 0% by volume, and
H$_2$O 17.3% by volume.

The leaving amount is 8.70 m$^3$ (STP)/h.

Upstream of the static mixer disposed upstream of the third catalyst bed, 0.17 m$^3$ (STP)/h of molecular oxygen (purity >99% by volume) is metered into this reaction gas A (T=143° C., throttled in at a pressure of 1.78 bar). The resulting pressure of the resulting reaction gas is still 1.78 bar.

The bed height of the third catalyst bed is such that reaction gas A leaves the third catalyst bed as product gas A with a temperature of 540° C. and a pressure of 1.73 bar with the following contents:
propane 46.30% by volume,
propylene 25.12% by volume,
ethylene 0.75% by volume,
methane 2.27% by volume,
H$_2$ 4.50% by volume,
O$_2$ 0% by volume, and
H$_2$O 20.05% by volume.

The leaving amount is 9.17 m$^3$ (STP)/h.

A flow divider divides product gas A into two portions of identical composition. The first portion is 5.04 m$^3$ (STP)/h and the second portion is 4.13 m$^3$ (STP)/h.

The first portion is recycled into reaction zone A as a constituent of the reaction gas A charge gas mixture. For the purpose of dehydrogenation cycle gas flow of the first portion, the propane cycle gas heated as described is used as the motive jet to operate a jet pump, the conveying direction of the motive jet decompressed through a motive nozzle via a mixing zone and a diffuser pointing in the direction of the entrance to reaction zone A, and the suction nozzle pointing in the direction of the first flow portion of product gas A and the "suction nozzle—mixing zone—diffuser" connection forming the sole connecting line between the first portion of product gas A to be recycled and the access to reaction zone A.

The second portion of product gas A is conducted out of reaction zone A and first cooled from 540° C. to 476° C. by a first indirect heat exchange with the first gas mixture, composed of crude propane and molecular oxygen, involved in the reaction gas A starting mixture (charge gas mixture). The working pressure of product gas A is essentially retained.

At the same time, the first gas mixture is heated from 235° C. to 450° C., while the working pressure of this gas mixture of 1.84 bar is essentially retained.

In a downstream second indirect heat exchange with propane cycle gas from separation zone IV, product gas A is cooled from 476° C. to 307° C. Conversely, the temperature of the propane cycle gas rises from 69° C. to 400° C.

Subsequently, 0.52 m$^3$ (STP)/h of steam is removed by condensation from the product gas A cooled to 307° C. To this end, the product gas A cooled to 307° C. is first conducted in indirect heat exchange to 3.60 m$^3$ (STP)/h of product gas A* (T=54° C., P=1.73 bar) from which the appropriate amount of steam has already been removed by condensation, and thus cooled to 111° C. The temperature of product gas A* simultaneously increases to 277° C.

Direct cooling with sprayed aqueous condensate which has been cooled (to 29° C.) and removed beforehand from product gas A by appropriate direct cooling removes the aforementioned amount of steam from product gas A by condensation to obtain a product gas A* (P=1.73 bar, T=54° C., 3.60 m$^3$ (STP)/h). This is heated to 277° C. as described above. 1.39 m$^3$ (STP)/h of molecular oxygen (purity >99% by volume, T=143° C., P=2.40 bar) are then throttled into the product gas A*. This forms a reaction gas B starting mixture (charge gas mixture) which has a temperature of 262° C. and a working pressure of 1.63 bar.

The reaction gas B starting mixture (charge gas mixture) has the following contents:
propane 38.26% by volume,
propylene 20.77% by volume,
ethylene 0.62% by volume,
methane 1.87% by volume, H$_2$ 3.73% by volume,
O$_2$ 27.53% by volume, and
H$_2$O 6.20% by volume.

This is used to charge reaction zone B which has the same structure as that from II.

The propylene loading on the catalyst charge of the first oxidation stage is selected to be 164 l(STP)/l·h. The salt melts (53% by weight of KNO$_3$, 40% by weight of NaNO$_2$, 7% by weight of NaNO$_3$) have the following entrance temperatures:
$T_A$=331° C. $T_B$=339° C.
$T_C$=275° C. $T_D$=282° C.

Sufficient molecular oxygen (143° C., 2.40 bar) is metered (throttled) into the product gas mixture of the first oxidation stage that the molar O$_2$: acrolein ratio in the resulting charge gas mixture for the second oxidation stage is 0.72. The acrolein loading on the catalyst charge of the second oxidation stage is 139 l(STP)/l·h. The pressure at the entrance to the second oxidation stage is 1.57 bar.

Reaction gas B leaves the intermediate cooler with a temperature of 260° C. and the entrance temperature of the charge gas mixture into the second oxidation stage is 256° C.

The product gas mixture of the first oxidation stage has the following contents:
acrolein 17.51% by volume,
acrylic acid 1.18% by volume,
propane 38.12% by volume,
propylene 1.03% by volume,
methane 1.86% by volume,
H$_2$ 3.71% by volume,
ethylene 0.62% by volume, O$_2$ 4.18% by volume,
H$_2$O 27.83% by volume,
CO 0.88% by volume, and
CO$_2$ 2.07% by volume.

Before entry into the aftercooler, the temperature of the product gas of the first oxidation stage is 335° C.

The product gas mixture of the second oxidation stage (product gas B) has a temperature of 270° C. and a pressure of 1.55 bar, and also the following contents:
acrolein 0.089% by volume,
acrylic acid 17.67% by volume,
acetic acid 0.52% by volume,
propane 37.99% by volume,
propylene 1.02% by volume,
methane 1.86% by volume,
ethylene 0.62% by volume,
H$_2$ 3.70% by volume,
O$_2$ 2.61% by volume,
H$_2$O 28.42% by volume,
CO 1.41% by volume and
CO$_2$ 3.10% by volume.

As described in WO 2004/035514, product gas B (5.03 m$^3$ (STP)/h) is fractionally condensed in a tray column (separation zone II).

As the first fuel, 13.9 g/h of high boilers (polyacrylic acids (Michael adducts), etc.) are fed to the residue incineration.

From the second collecting tray above the feed of product gas B into the tray column, 2.82 kg/h of a condensed crude acrylic acid are withdrawn which has a temperature of 15° C. and 96.99% by weight of acrylic acid. As described in WO 2004/035514, this is suspension-crystallized after addition of a small amount of water, the suspension crystals are separated from the mother liquor in hydraulic scrubbing columns and the mother liquor is recycled into the condensation column as described in WO 2004/035514. The purity of the washed suspension crystals is >99.87% by weight of acrylic acid and is suitable immediately for preparing water-"superabsorbing" polymers for use in the hygiene sector.

The amount of acid water condensate withdrawn from the third collecting tray above the feed of product gas B into the condensation column but not recycled into the condensation column is 1.24 kg/h, has a temperature of 33° C. and has the following contents:
0.73% by weight of acrolein,
4.95% by weight of acrylic acid,
5.16% by weight of acetic acid and
88.1% by weight of water.

At the top of the condensation column, 2.72 m$^3$ (STP)/h of residual gas leave separation zone II with a temperature of 33° C. and a pressure of 1.20 bar and the following contents:
acrolein 0.03% by volume,
acrylic acid 0.02% by volume,
acetic acid 0.01% by volume,
propane 70.26% by volume,
propylene 1.91% by volume,
ethylene 1.15% by volume,
H$_2$ 6.93% by volume,
methane 3.44% by volume,
O$_2$ 4.83% by volume,
H$_2$O 2.11% by volume,
CO 2.59% by volume and
CO$_2$ 5.73% by volume.

In the first compressor stage of a multistage radial compressor, the residual gas is compressed from 1.20 bar to 6.93 bar, in the course of which the temperature of the residual gas rises to 127° C.

In an indirect heat exchanger, it is cooled to 114° C. without condensate being formed (coolant is the "propane-scrubbed" residual gas (also referred to hereinafter as "offgas") which, after being heated from 30° C. to 84° C. in an indirect heat exchanger, is decompressed starting from 20 bar in the first expansion stage of a multistage expansion turbine and cooled at the same time). This heats the offgas (0.69 m$^3$ (STP)/h). In a second expansion stage, the offgas is decompressed to 1.10 bar (it then has a temperature of 18° C.) and then fed to residue incineration.

In an indirect air cooler, the compressed residual gas (P=6.93 bar and T=114° C.) is cooled to 59° C. In a further compressor stage, it is compressed from 6.93 bar to 20 bar, which simultaneously heats it to 114° C. In a downstream indirect heat exchanger, it is cooled to 107° C. (coolant is the "propane-scrubbed" residual gas which is heated at the same time from 30° C. to 84° C.) without condensate being formed. In a further indirect heat exchanger downstream, the residual gas at 107° C. is cooled to 35° C. (coolant is surface water at approx. 25° C.).

This condenses 44.8 g/h of water out of the residual gas. This aqueous condensate is likewise fed to residue incineration and incinerated therein together with the other residues mentioned (with supply of 5.95 m$^3$ (STP)/h of air). The hot combustion gases are cooled to obtain steam (52 bar, 267° C., 5.16 kg/h) and released into the environment.

The residual gas which now still comprises 2.67 m$^3$ (STP)/h of propane (20 bar, 35° C.) is conducted into the lower section of a column with random packing (separation zone At the top of this scrubbing column, 20.39 kg/h of technical tetradecane from Haltermann, Germany (as described in II) are introduced with an introduction temperature of 30° C. (P=20 bar).

At the top of the scrubbing column, "propane-scrubbed" residual gas (offgas) escapes, which, at a pressure of 20 bar and a temperature of 30° C. and an amount of 0.69 m$^3$ (STP)/h, has the following contents:

propane 1.38% by volume,
propylene 0.04% by volume,
ethylene 4.48% by volume,
methane 13.44% by volume,
$H_2$ 27.12% by volume,
$O_2$ 18.89% by volume,
$H_2O$ 1.04% by volume,
CO 10.16% by volume and
$CO_2$ 22.44% by volume.

This offgas is decompressed as described and subjected to indirect heat exchange and then fed to residue incineration or incinerated by means of a flare.

24.27 kg/h of absorbate which have a pressure of 20 bar and a temperature of 61° C. are withdrawn from the bottom of the "propane scrubbing column" which is neither externally cooled nor heated. It comprises 15.63% by weight of propane and 0.41% by weight of propylene.

Before the absorbate is conducted to the top of the downstream desorption column, it is heated to 69° C. in an indirect heat exchanger. The heat carrier used is the liquid effluent from the desorption column (20.39 kg/h) which has a temperature of 80° C. at a pressure of 3.26 bar and still comprises 0.089% by weight of dissolved propane. By means of a pump, it is compressed back to 20 bar, and, after indirect cooling with surface water (25° C.) to 30° C., it is recycled to the propane absorption at the top of the "propane scrubbing column".

After being heated to 69° C., the absorbate (for example in an inverse pump or by means of a valve) is decompressed to a pressure of 3.26 bar (the mechanical energy released in the case of the inverse pump is appropriately also used to recompress absorbent freed of propane in the desorption column (the liquid effluent of the desorption column)), and the biphasic mixture obtained is conducted into the desorption column at the top.

0.1 kg/h of steam is fed with a pressure of 5 bar and a temperature of 152° C. as stripping gas into the desorption column (likewise a column with random packing) from the bottom in countercurrent to the absorbate descending from the top of the desorption column.

Disposed in the desorption column is a heating coil through which steam of temperature 152° C., P=5.00 bar in an amount of 0.8 kg/h is likewise conducted in countercurrent to the steam ascending in the desorption column.

At the top of the desorption column, 2.04 m³ (STP)/h of propane cycle gas which have a temperature of 69° C. and a working pressure of 3.26 bar escape. After heating to 400° C. by indirect heat exchange with product gas A of temperature T=476° C., the propane cycle gas is used as the motive jet to operate the jet pump, with which the dehydrogenation cycle gas and the propane cycle gas in the mixture are fed to the charging of reaction zone A with reaction gas A starting mixture.

The propane cycle gas has the following contents:
propane 93.07% by volume,
propylene 2.52% by volume, and
$H_2O$ 3.40% by volume.

IV. Third Illustrative Process for Preparing Acrylic Acid from Propane (a Steady Operating State is Described)

Reaction zone A is a tray reactor as described under II.

The heterogeneously catalyzed partial propane dehydrogenation is carried out in the tray reactor described in straight pass without dehydrogenation cycle gas mode. The loading of the total amount of catalyst (calculated without inert material) of all trays with propane is 1500 l (STP)/l·h.

3.80 m³ (STP)/h of reaction gas A charge gas mixture (starting mixture; T=418° C.; P=1.77 bar) are fed to the first catalyst bed in flow direction and have the following contents:
propane 75.21% by volume,
propylene 1.35% by volume,
methane 0.01% by volume,
$H_2$ 8.60% by volume,
$O_2$ 4.32% by volume,
$N_2$ 0.96% by volume,
$H_2O$ 7.68% by volume,
CO 0.02% by volume, and
$CO_2$ 0.83% by volume.

The reaction gas A charge gas mixture is a mixture of a first (1.59 m³ (STP)/h) and a second (2.21 m³ (STP)/h) gas mixture which is obtained by combining the two gas mixtures by means of a static mixer. The first gas mixture has a temperature of 450° C. and a pressure of 1.77 bar and is composed of:
1.02 m³ (STP)/h of crude propane which comprises propane (fresh propane) to an extent of >98% by volume (T=237° C., P=2.90 bar),
0.16 m³ (STP)/h of $O_2$ (T=143° C., P=1.77 bar, purity >99% by volume), and
0.41 m³ (STP)/h of gas which comprises predominantly molecular hydrogen and is removed from the "propane-scrubbed" residual gas (offgas) by membrane separation (T=30° C.; it is throttled to 1.77 bar).

Indirect heat exchange in a first heat exchanger with product gas A conducted out of reaction zone A and in the direction of reaction zone B establishes the temperature of 450° C.

The second gas mixture is propane cycle gas (2.21 m³ (STP)/h; 400° C.; 1.77 bar). Indirect heat exchange with the product gas A cooled to a temperature of 500° C. in the first heat exchanger establishes the temperature of the propane cycle gas.

The entrance temperature of the reaction gas A charge gas mixture and the bed height of the first catalyst bed flowed through by the reaction gas A charge gas mixture are adjusted such that reaction gas A leaves this catalyst bed with a temperature of 507° C. and a pressure of 1.76 bar with the following contents:
propane 64.42% by volume,
propylene 9.10% by volume,
ethylene 0.079% by volume,
methane 0.33% by volume,
$H_2$ 7.63% by volume,
$O_2$ 0% by volume,
$N_2$ 0.92% by volume,
$H_2O$ 15.69% by volume,
CO 0% by volume, and
$CO_2$ 0.82% by volume.

The leaving amount is 3.95 m³ (STP)/h.

Beyond the first catalyst bed, 0.13 m³ (STP)/h of molecular oxygen (purity >99% by volume) is metered into reaction gas A (T=143° C., P=2.40 bar). The metered addition is effected by throttling, so that the resulting pressure of the resulting reaction gas A is still 1.76 bar.

The bed height of the second catalyst bed is such that reaction gas A leaves the second catalyst bed with a temperature of 544° C. and a pressure of 1.75 bar with the following contents:
propane 51.72% by volume,
propylene 15.97% by volume,
ethylene 0.149% by volume,
methane 0.60% by volume,
$H_2$ 8.68% by volume,
$O_2$ 0% by volume,
$N_2$ 0.85% by volume, $H_2O$ 20.26% by volume,
CO 0% by volume, and
$CO_2$ 0.76% by volume.

The leaving amount is 4.29 m³ (STP)/h.

Upstream of the static mixer disposed upstream of the third catalyst bed, 0.12 m³ (STP)/h of molecular oxygen (purity >99% by volume) is metered into this reaction gas A (T=143° C., throttled in at a pressure of 1.75 bar). The resulting pressure of the resulting reaction gas is still 1.75 bar.

The bed height of the third catalyst bed is such that reaction gas A leaves the third catalyst bed as product gas A with a temperature of 571° C. and a pressure of 1.73 bar with the following contents:
propane 40.12% by volume,
propylene 22.2% by volume,
ethylene 0.22% by volume,
methane 0.87% by volume,
$H_2$ 10.11% by volume,
$O_2$ 0% by volume,
$N_2$ 0.79% by volume,
$H_2O$ 23.96% by volume,
CO 0% by volume, and
$CO_2$ 0.70% by volume.

Product gas A is conducted out of reaction zone A and first cooled from 571° C. to 500° C. by a first indirect heat exchange with the first gas mixture which is involved in the reaction gas A starting mixture (charge gas mixture) and is composed of crude propane, molecular hydrogen-comprising gas and molecular oxygen. The working pressure of product gas A is essentially retained. This heats the first gas mixture from 213° C. to 450° C., while the working pressure of this gas mixture of 1.77 bar is essentially retained.

In a subsequent second indirect heat exchange with propane cycle gas from separation zone IV, product gas A is cooled from 500° C. to 337° C. Conversely, the temperature of the propane cycle gas rises from 69° C. to 400° C.

Subsequently, 0.79 m³ (STP)/h of steam is separated by condensation from product gas A cooled to 337° C. To this end, the product gas A cooled to 307° C. is first conducted in indirect heat exchange to 3.85 m³ (STP)/h of product gas A* (T=54° C.; P=1.73 bar) from which the appropriate amount of steam has already been removed by condensation beforehand, and thus cooled to 120° C.

The temperature of product gas A* simultaneously increases to 307° C.

Direct cooling with sprayed aqueous condensate which has been cooled (to 29° C.) and removed beforehand from product gas A by appropriate direct cooling removes the aforementioned amount of steam from product gas A by condensation to obtain a product gas A* (P=1.73 bar, T=54° C., 3.85 m³ (STP)/h).

This is heated to 307° C. as described above. 1.41 m³ (STP)/h of molecular oxygen (purity >99% by volume, T=143° C., P=2.40 bar) are then throttled into the product gas A*. This forms a reaction gas B starting mixture (charge gas mixture) which has a temperature of 290° C. and a working pressure of 1.63 bar.

The reaction gas B starting mixture (charge gas mixture) has the following contents:
propane 35.35% by volume,
propylene 19.60% by volume,
ethylene 0.19% by volume,
methane 0.76% by volume,
$H_2$ 8.91% by volume,
$O_2$ 26.60% by volume,
$N_2$ 0.69% by volume,
$H_2O$ 6.27% by volume,
CO 0% by volume, and
$CO_2$ 0.62% by volume.

This is used to charge reaction zone B which has the same structure as that from II. The propylene loading on the catalyst charge of the first oxidation stage is selected to be 130 l (STP)/l·h. The salt melts (53% by weight of $KNO_3$, 40% by weight of $NaNO_2$, 7% by weight of $NaNO_3$) have the following entrance temperatures:
$T_A$=322° C. $T_B$=327° C.
$T_C$=261° C. $T_D$=268° C.

Sufficient molecular oxygen (143° C., 2.40 bar) is metered (throttled) into the product gas mixture of the first oxidation stage that the molar $O_2$: acrolein ratio in the resulting charge gas mixture for the second oxidation stage is 0.745. The acrolein loading on the catalyst charge of the second oxidation stage is 110 l (STP)/l·h. The pressure at the entrance to the second oxidation stage is 1.57 bar. Reaction gas B leaves the intermediate cooler with a temperature of 260° C. and the entrance temperature of the charge gas mixture into the second oxidation stage is 256° C.

The product gas mixture of the first oxidation stage has the following contents:
acrolein 16.51% by volume,
acrylic acid 1.11% by volume,
propane 35.23% by volume,
propylene 0.98% by volume,
ethylene 0.19% by volume,
methane 0.76% by volume,
$H_2$ 8.88% by volume,
$O_2$ 4.57% by volume,
$N_2$ 0.69% by volume,
$H_2O$ 26.66% by volume,
CO 0.83% by volume, and
$CO_2$ 2.56% by volume.

Before entry into the aftercooler, the temperature of the product gas of the first oxidation stage is 335° C.

The product gas mixture of the second oxidation stage (product gas B) has a temperature of 270° C. and a pressure of 1.55 bar, and also the following contents:
acrolein 0.08% by volume,
acrylic acid 16.71% by volume,
acetic acid 0.495% by volume,
propane 35.20% by volume,
propylene 0.89% by volume,
ethylene 0.19% by volume,
methane 0.76% by volume,
$H_2$ 8.87% by volume,
$O_2$ 2.86% by volume,
$N_2$ 0.69% by volume,
$H_2O$ 27.28% by volume,
CO 1.33% by volume, and
$CO_2$ 3.54% by volume.

As described in WO 2004/035514, product gas B (5.29 m³ (STP)/h) is fractionally condensed in a tray column (separation zone II).

As the first fuel, 13.8 g/h of high boilers (polyacrylic acids (Michael adducts), etc.) are fed to the residue incineration.

From the second collecting tray above the feed of product gas B into the tray column, 2.80 kg/h of a condensed crude acrylic acid are withdrawn which has a temperature of 15° C. and 96.99% by weight of acrylic acid. As described in WO 2004/035514, this is suspension-crystallized after addition of a small amount of water, the suspension crystals are separated from the mother liquor in hydraulic scrubbing columns and the mother liquor is recycled into the condensation column as described in WO 2004/035514.

The purity of the washed suspension crystals is >99.87% by weight of acrylic acid and is suitable immediately for preparing water-"superabsorbing" polymers for use in the hygiene sector.

The amount of acid water condensate withdrawn from the third collecting tray above the feed of product gas B into the condensation column but not recycled into the condensation column is 1.25 kg/h, has a temperature of 33° C. and has the following contents:
  0.72% by weight of acrolein,
  4.95% by weight of acrylic acid,
  5.09% by weight of acetic acid and
  88.24% by weight of water.

At the top of the condensation column, 2.98 m$^3$ (STP)/h of residual gas leave separation zone II with a temperature of 33° C. and a pressure of 1.20 bar and the following contents:
  acrolein 0.02% by volume,
  acrylic acid 0.02% by volume,
  propane 62.39% by volume,
  propylene 1.73% by volume,
  ethylene 0.34% by volume,
  methane 1.35% by volume,
  $H_2$ 16.23% by volume,
  $O_2$ 5.05% by volume,
  $N_2$ 1.27% by volume,
  $H_2O$ 1.92% by volume,
  CO 2.36% by volume, and
  $CO_2$ 6.33% by volume.

In the first compressor stage of a multistage radial compressor, the residual gas is compressed from 1.20 bar to 6.93 bar, in the course of which the temperature of the residual gas rises to 134° C.

In an indirect heat exchanger, it is cooled to 123° C. without condensate being formed (coolant is the "propane-scrubbed" residual gas (also referred to hereinafter as "offgas") which, after removal of molecular hydrogen by means of a separating membrane and after being heated from 30° C. to 102° C. in an indirect heat exchanger, is decompressed starting from 20 bar in the first expansion stage of a multistage expansion turbine and cooled at the same time). This heats the offgas (0.59 m$^3$ (STP)/h). In a second expansion stage, the offgas is decompressed to 1.10 bar (it then has a temperature of 23° C.) and then fed to residue incineration.

In an indirect air cooler, the compressed residual gas (P=6.93 bar and T=134° C.) is cooled to 59° C. In a further compressor stage, it is compressed from 6.93 bar to 20 bar, which simultaneously heats it to 117° C. In a downstream indirect heat exchanger, it is cooled to 110° C. (coolant is the "propane-scrubbed" residual gas, on completion of $H_2$ membrane removal, which is heated at the same time from 30° C. to 102° C.) without condensate being formed. In a further indirect heat exchanger downstream, the residual gas at 110° C. is cooled to 35° C. (coolant is surface water at approx. 25° C.).

This condenses 44.2 g/h of water out of the residual gas. This aqueous condensate is likewise fed to residue incineration and incinerated therein together with the other residues mentioned with supply of 4.12 m$^3$ (STP)/h of air. The hot combustion gases are cooled to obtain steam (52 bar, 267° C., 3.41 kg/h) and released into the environment.

The residual gas which now still comprises 2.93 m$^3$ (STP)/h of propane (20 bar, 35° C.) is conducted into the lower section of a column with random packing (separation zone III). At the top of this scrubbing column, 21.62 kg/h of technical tetradecane from Haltermann, Germany (as described in II) are introduced with an introduction temperature of 30° C. (P=20 bar).

At the top of the scrubbing column, "propane-scrubbed" residual gas (offgas) escapes, which, at a pressure of 20 bar and a temperature of 30° C. and an amount of 1.01 m$^3$ (STP)/h, has the following contents:
  propane 0.92% by volume,
  propylene 0.03% by volume,
  ethylene 0.99% by volume,
  methane 3.99% by volume,
  $H_2$ 47.97% by volume,
  $O_2$ 14.94% by volume,
  $N_2$ 3.75% by volume,
  $H_2O$ 0.78% by volume,
  CO 6.95% by volume and
  $CO_2$ 18.69% by volume.

This "propane-scrubbed" offgas is conducted to a bundle of cast tube membranes (external pressure: 1.77 bar; B-H polyimide membrane from UBE Industries Ltd.) and leaves them (P=20 bar; T=30° C.) with release of 0.41 m$^3$ (STP)/h of a gas stream (permeate stream) which has the following contents:
  ethylene 0.02% by volume,
  methane 0.059% by volume,
  $H_2$ 79.15% by volume,
  $O_2$ 1.53% by volume,
  $N_2$ 8.83% by volume,
  $H_2O$ 1.52% by volume,
  CO 0.22% by volume, and
  $CO_2$ 7.68% by volume.

This gas stream is fed to (throttled into) the first gas mixture to generate the reaction gas A charge gas mixture.

The remaining offgas is decompressed as described and subjected to indirect heat exchange, and then fed to residue incineration or incinerated in a flare.

25.40 kg/h of absorbate which have a pressure of 20 bar and a temperature of 59° C. are withdrawn from the bottom of the "propane scrubbing column" which is neither externally cooled nor heated. It comprises 14.40% by weight of propane and 0.38% by weight of propylene.

Before the absorbate is conducted to the top of the downstream desorption column, it is heated to 69° C. in an indirect heat exchanger. The heat carrier used is the liquid effluent from the desorption column (21.62 kg/h) which has a temperature of 80° C. at a pressure of 3.26 bar and still comprises 0.09% by weight of dissolved propane. By means of a pump, it is compressed back to 20 bar, and, after indirect cooling with surface water (25° C.) to 30° C., it is recycled to the propane absorption at the top of the "propane scrubbing column".

After being heated to 69° C., the absorbate (for example in an inverse pump or by means of a valve) is decompressed to a pressure of 3.26 bar (the mechanical energy released in the case of the inverse pump is appropriately also used to recompress absorbent freed of propane in the desorption column (the liquid effluent of the desorption column)), and the biphasic mixture obtained is conducted into the desorption column at the top.

0.2 kg/h of steam is fed with a pressure of 5 bar and a temperature of 152° C. as stripping gas into the desorption column (likewise a column with random packing) from the bottom in countercurrent to the absorbate descending from the top of the desorption column.

Disposed in the desorption column is a heating coil through which steam of temperature 152° C., P=5.00 bar in an amount of 0.8 kg/h is likewise conducted in countercurrent to the steam ascending in the desorption column.

At the top of the desorption column, 2.21 m³ (STP)/h of propane cycle gas which have a temperature of 69° C. and a working pressure of 3.26 bar escape.

After heating to 400° C. by indirect heat exchange with product gas A of temperature T=476° C., the propane cycle gas is fed to the charging of reaction zone A with reaction gas A starting mixture.

The propane cycle gas has the following contents:
propane 83.73% by volume,
propylene 2.32% by volume, and
$H_2O$ 12.94% by volume.

V. Fourth Illustrative Process for Preparing Acrylic Acid from Propane (a Steady Operating State is Described)

Reaction zone A is a tray reactor as described under II., except that connected downstream of it in this example is a further adiabatic shaft furnace reactor which has only one fixed catalyst bed and which corresponds in its configuration to the first fixed bed tray in the tray reactor in flow direction. Between the two reactors, an indirect heat exchanger is connected. The heterogeneously catalyzed partial propane dehydrogenation is carried out in the tray reactor in straight pass with dehydrogenation cycle gas mode. The loading of the total amount of catalyst (calculated without inert material) of all trays with propane is 1500 l (STP)/l·h. In the downstream shaft furnace reactor, essentially only a heterogeneously catalyzed combustion of molecular hydrogen is effected.

6.93 m³ (STP)/h of reaction gas A charge gas mixture (starting mixture; P=2.46 bar) are fed to the first catalyst bed of the tray reactor in flow direction and have the following contents:
propane 60.54% by volume,
propylene 10.38% by volume,
ethylene 0.28% by volume,
methane 0.87% by volume,
$H_2$ 2.44% by volume,
$O_2$ 1.19% by volume,
$N_2$ 16.48% by volume,
$H_2O$ 6.82% by volume,
CO 0% by volume, and
$CO_2$ 0.01% by volume.

The reaction gas A charge gas mixture is a mixture of a first (1.47 m³ (STP)/h) and a second (5.46 m³ (STP)/h) gas mixture which is obtained by combining the two gas mixtures by means of a static mixer.

The first gas mixture has a temperature of 500° C. and a pressure of 2.46 bar and is composed of:
1.06 m³ (STP)/h of crude propane which comprises propane (fresh propane) to an extent of >98% by volume (T=237° C.; P=2.90 bar),
and
0.41 m³ (STP)/h of compressed air (T=159° C.; P=2.66 bar).

Indirect heat exchange (in the intermediate cooler, heat exchanger disposed between the two reactors) with reaction gas A conducted out of the tray reactor and in the direction of the downstream shaft reactor establishes the temperature of 500° C.

The second gas mixture is composed of:
3.48 m³ (STP)/h of dehydrogenation cycle gas (T=554° C.; P=2.37 bar)
and
1.98 m³ (STP)/h of propane cycle gas (T=500° C.; P=2.97 bar).

It has a pressure of 2.46 bar and a temperature of 529° C.

Indirect heat exchange with product gas A conducted out of the downstream shaft reactor establishes the temperature of the propane cycle gas. The dehydrogenation cycle gas flow is effected according to the jet pump principle (cf. DE-A 10211275), the propane cycle gas heated to 500° C. functioning as the motive jet.

The entrance temperature of the reaction gas A charge gas mixture and the bed height of the first catalyst bed flowed through by the reaction gas A charge gas mixture in flow direction in the tray reactor are adjusted such that reaction gas A leaves this catalyst bed with a temperature of 522° C. and a pressure of 2.44 bar with the following contents:
propane 53.77% by volume,
propylene 14.45% by volume,
ethylene 0.29% by volume,
methane 1.26% by volume,
$H_2$ 4.31% by volume,
$O_2$ 0% by volume,
$N_2$ 15.91% by volume,
$H_2O$ 8.88% by volume,
CO 0% by volume,
$CO_2$ 0.01% by volume.

The leaving amount is 7.18 m³ (STP)/h. Beyond the first catalyst bed of the tray reactor, 0.64 m³ (STP)/h of air is metered into reaction gas A (T=159° C., P=2.66 bar). The metered addition is effected by throttling, so that the resulting pressure of the resulting reaction gas A is still 2.44 bar.

The bed height of the second catalyst bed of the tray reactor is such that reaction gas A leaves the second catalyst bed with a temperature of 539° C. and a pressure of 2.41 bar with the following contents:
propane 43.71% by volume,
propylene 17.02% by volume,
ethylene 0.51% by volume,
methane 1.52% by volume,
$H_2$ 4.53% by volume,
$O_2$ 0% by volume,
$N_2$ 20.35% by volume,
$H_2O$ 11.37% by volume,
CO 0% by volume, and
$CO_2$ 0.01% by volume.

The leaving amount is 8.04 m³ (STP)/h.

Upstream of the static mixer disposed upstream of the third catalyst bed of the tray reactor, 0.63 m³ (STP)/h of air is metered into this reaction gas A (T=159° C., throttled in at a pressure of 2.66 bar). The resulting pressure of the resulting reaction gas A is still 2.41 bar.

The bed height of the third catalyst bed of the tray reactor is such that reaction gas A leaves the third catalyst bed with a temperature of 554° C. and a pressure of 2.37 bar with the following contents:
propane 35.58% by volume,
propylene 19.15% by volume,
ethylene 0.57% by volume,
methane 1.72% by volume,
$H_2$ 4.82% by volume,
$O_2$ 0% by volume,
$N_2$ 23.83% by volume,
$H_2O$ 13.31% by volume,
CO 0% by volume, and
$CO_2$ 0.01% by volume.

The leaving amount is 8.89 m³ (STP)/h.

A flow divider divides reaction gas A into two portions of identical composition at the outlet of the tray reactor. The first portion is 3.49 m³ (STP)/h and the second portion is 5.40 m³ (STP)/h. The first portion is recycled into reaction zone A as a constituent of the reaction gas A charge gas mixture. For the purpose of dehydrogenation cycle gas flow of the first portion, the propane cycle gas heated as described is used as the motive jet to operate a jet pump, the conveying direction of the motive jet decompressed through a motive nozzle via a mixing zone and a diffuser pointing in the direction of the entrance to reaction zone A, and the suction nozzle pointing in the direction of the first flow portion of reaction gas A and the "suction nozzle—mixing zone—diffuser" connection forming the sole connecting line between the first portion of reaction gas A to be recycled and the access to reaction zone A.

The second portion of reaction gas A is conducted out of reaction zone A and cooled from 554° C. to 473° C. by a first indirect heat exchange with the first gas mixture, composed of crude propane and molecular oxygen, involved in the reaction gas A starting mixture (charge gas mixture) in the intermediate cooler disposed between the tray reactor and the shaft reactor downstream thereof. This heats the first gas mixture from 229° C. to 500° C.; the working pressures are essentially retained.

6406 m³ (STP)/h of air are then metered into the second portion, cooled as described, of reaction gas A (T=159° C., throttled to 2.66 bar). The gas mixture is then conducted through the downstream shaft reactor.

The bed height of the ("fourth") catalyst bed disposed in the downstream shaft reactor is such that reaction gas A leaves this catalyst bed as product gas A with a temperature of 580° C. and a pressure of 2.26 bar with the following contents:
propane 32.53% by volume,
propylene 17.48% by volume,
ethylene 0.52% by volume,
methane 1.57% by volume,
$H_2$ 0% by volume,
$O_2$ 0% by volume,
$N_2$ 30.08% by volume,
$H_2O$ 16.79% by volume,
CO 0% by volume, and
$CO_2$ 0.01% by volume.

In a downstream (second) indirect heat exchange with propane cycle gas from separation zone IV, product gas A (5.92 m³ (STP)/h) is cooled from 580° C. to 388° C. Conversely, the temperature of the propane cycle gas rises from 69° C. to 500° C.

Subsequently, 0.82 m³ (STP)/h of steam is removed by condensation from the product gas A cooled to 388° C. To this end, the product gas A cooled to 388° C. is first conducted in indirect heat exchange to 5.10 m³ (STP)/h of product gas A* (T=40° C.; P=2.01 bar) from which the appropriate amount of steam has already been removed by condensation beforehand, and thus cooled to 112° C. The temperature of product gas A* is simultaneously increased to 358° C. In a downstream air cooler, product gas A (T=112° C.; P=2.26 bar) is cooled to 54° C. by indirect heat exchange with outside air (the working pressure of product gas A falls at the same time to 2.06 bar) and thereafter already has biphasicity.

Direct cooling with sprayed aqueous condensate which has been cooled (to 29° C.) and removed beforehand from product gas A by appropriate direct cooling removes the aforementioned amount of steam from product gas A by condensation to obtain a product gas A* (P=2.01 bar, T=40° C., 5.10 m³ (STP)/h). This is heated to 358° C. as described above. 8.55 m³ (STP)/h of air (T=159° C., P=2.66 bar) are then throttled into the product gas A*. This forms a reaction gas B starting mixture (charge gas mixture) which has a temperature of 283° C. and a working pressure of 1.96 bar.

The reaction gas B starting mixture (charge gas mixture) has the following contents:
propane 14.11% by volume,
propylene 7.58% by volume,
ethylene 0.23% by volume,
methane 0.68% by volume,
$H_2$ 0% by volume,
$O_2$ 12.69% by volume,
$N_2$ 60.9% by volume,
$H_2O$ 2.75% by volume,
CO 0% by volume, and
$CO_2$ 0.03% by volume.

This is used to charge reaction zone B which has the same structure as that from II.

The propylene loading on the catalyst charge of the first oxidation stage is selected to be 130 l(STP)/l·h. The salt melts (53% by weight of $KNO_3$, 40% by weight of $NaNO_2$, 7% by weight of $NaNO_3$) have the following entrance temperatures:
$T_A$=327° C. $T_B$=329° C.
$T_C$=267° C. $T_D$=268° C.

Sufficient air (159° C., 2.66 bar) is metered (throttled) into the product gas mixture of the first oxidation stage that the molar $O_2$: acrolein ratio in the resulting charge gas mixture for the second oxidation stage is 1.01.

The acrolein loading on the catalyst charge of the second oxidation stage is 110 l(STP)/l·h. The pressure at the entrance to the second oxidation stage is 1.68 bar. Reaction gas B leaves the intermediate cooler with a temperature of 260° C. and the entrance temperature of the charge gas mixture into the second oxidation stage is 253° C.

The product gas mixture of the first oxidation stage has the following contents:
acrolein 6.40% by volume,
acrylic acid 0.44% by volume,
propane 14.09% by volume,
propylene 0.39% by volume,
methane 0.68% by volume,
$H_2$ 0% by volume,
ethylene 0.23% by volume,
$O_2$ 4.18% by volume,
$N_2$ 60.87% by volume,
$H_2O$ 10.64% by volume,
CO 0.33% by volume, and
$CO_2$ 0.78% by volume.

Before entry into the aftercooler, the temperature of the product gas of the first oxidation stage is 335° C.

The product gas mixture of the second oxidation stage (product gas B) has a temperature of 270° C. and a pressure of 1.55 bar, and also the following contents:
acrolein 0.03% by volume,
acrylic acid 5.97% by volume,
acetic acid 0.18% by volume,
propane 13.0% by volume,
propylene 0.36% by volume,
methane 0.63% by volume,
ethylene 0.21% by volume,
$H_2$ 0% by volume,
$O_2$ 2.60% by volume,
$N_2$ 64.2% by volume,
$H_2O$ 10.29% by volume,
CO 0.48% by volume and
$CO_2$ 1.08% by volume.

As described in WO 2004/035514, product gas B (14.81 m³ (STP)/h) is fractionally condensed in a tray column (separation zone II).

As the first fuel, 13.8 g/h of high boilers (polyacrylic acids (Michael adducts), etc.) are fed to the residue incineration.

From the second collecting tray above the feed of product gas B into the tray column, 2.80 kg/h of a condensed crude acrylic acid are withdrawn which has a temperature of 15° C. and 96.99% by weight of acrylic acid. As described in WO 2004/035514, this is suspension-crystallized after addition of a small amount of water, the suspension crystals are separated from the mother liquor in hydraulic scrubbing columns and the mother liquor is recycled into the condensation column as described in WO 2004/035514. The purity of the washed suspension crystals is >99.87% by weight of acrylic acid and is suitable immediately for preparing water-"superabsorbing" polymers for use in the hygiene sector.

The amount of acid water condensate withdrawn from the third collecting tray above the feed of product gas B into the condensation column but not recycled into the condensation column is 1.19 kg/h, has a temperature of 34° C. and has the following contents:
    0.35% by weight of acrolein,
    4.95% by weight of acrylic acid,
    5.31% by weight of acetic acid and
    88.40% by weight of water.

At the top of the condensation column, 12.56 m³ (STP)/h of residual gas leave separation zone II with a temperature of 33° C. and a pressure of 1.20 bar and the following contents:
    acrolein 0.02% by volume,
    acrylic acid 0.02% by volume,
    acetic acid 0% by volume,
    propane 15.35% by volume,
    propylene 0.42% by volume,
    ethylene 0.25% by volume,
    methane 0.74% by volume,
    $H_2$ 0% by volume,
    $O_2$ 3.07% by volume,
    $N_2$ 75.64% by volume,
    $H_2O$ 1.68% by volume,
    CO 0.55% by volume, and
    $CO_2$ 1.27% by volume.

In the first compressor stage of a multistage radial compressor, the residual gas is compressed from 1.20 bar to 6.93 bar, in the course of which the temperature of the residual gas rises to 217° C.

In an indirect heat exchanger, it is cooled to 111° C. without condensate being formed (coolant is the "propane-scrubbed" residual gas (also referred to hereinafter as "offgas" which, after being heated from 30° C. to 138° C. in an indirect heat exchanger, is decompressed starting from 20 bar in the first expansion stage of a multistage expansion turbine and cooled at the same time). This heats the offgas (10.39 m³ (STP)/h). In a second expansion stage, the offgas is decompressed to 1.10 bar (it then has a temperature of 78° C.) and then fed to residue incineration.

In an indirect air cooler, the compressed residual gas (P=6.93 bar and T=111° C.) is cooled to 59° C. In a second compressor stage, it is compressed from 6.93 bar to 20 bar, which simultaneously heats it to 168° C. In a downstream indirect heat exchanger, it is cooled to 101° C. (coolant is the "propane-scrubbed" residual gas which is heated at the same time from 30° C. to 138° C.) without condensate being formed. In a further indirect heat exchanger downstream, the residual gas at 101° C. is cooled to 35° C. (coolant is surface water at approx. 25° C.).

This condenses 159.7 g/h of water out of the residual gas. This aqueous condensate is likewise fed to residue incineration and incinerated therein together with the other residues mentioned with supply of 5.59 m³ (STP)/h of air. The hot combustion gases are cooled to obtain steam (52 bar, 267° C., 3.78 kg/h) and released into the environment.

The residual gas which now still comprises 12.37 m³ (STP)/h of propane (20 bar, 35° C.) is conducted into the lower section of a column with random packing (separation zone III).

At the top of this scrubbing column, 66.37 kg/h of technical tetradecane from Haltermann, Germany (as described in II) are introduced with an introduction temperature of 30° C. (P=20 bar).

At the top of the scrubbing column, "propane-scrubbed" residual gas (offgas) escapes, which, at a pressure of 20 bar and a temperature of 30° C. and an amount of 10.39 m³ (STP)/h, has the following contents:
    propane 0.19% by volume,
    propylene 0.01% by volume,
    ethylene 0.29% by volume,
    methane 0.89% by volume,
    $H_2$ 0% by volume,
    $O_2$ 3.70% by volume,
    $N_2$ 91.38% by volume,
    $H_2O$ 0.32% by volume,
    CO 0.67% by volume, and
    $CO_2$ 1.53% by volume.

This offgas is decompressed as described and subjected to indirect heat exchange and then fed to residue incineration or incinerated by means of a flare.

70.25 kg/h of absorbate which have a pressure of 20 bar and a temperature of 41° C. are withdrawn from the bottom of the "propane scrubbing column" which is neither externally cooled nor heated. It comprises 5.41% by weight of propane and 0.14% by weight of propylene.

Before the absorbate is conducted to the top of the downstream desorption column, it is heated to 69° C. in an indirect heat exchanger. The heat carrier used is the liquid effluent from the desorption column (66.37 kg/h) which has a temperature of 80° C. at a pressure of 2.97 bar and still comprises 0.03% by weight of dissolved propane. By means of a pump, it is compressed back to 20 bar, and, after indirect cooling with surface water (25° C.) to 30° C., it is recycled to the propane absorption at the top of the "propane scrubbing column".

After being heated to 69° C., the absorbate (for example in an inverse pump or by means of a valve) is decompressed to a pressure of 2.97 bar (the mechanical energy released in the case of the inverse pump is appropriately also used to recompress absorbent freed of propane in the desorption column (the liquid effluent of the desorption column)), and the biphasic mixture obtained is conducted into the desorption column at the top.

Disposed in the desorption column is a heating coil through which steam of temperature 152° C., P=5.00 bar in an amount of 1.3 kg/h is conducted in cocurrent with the absorbate descending in the desorption column.

At the top of the desorption column, 1.98 m³ (STP)/h of propane cycle gas which have a temperature of 69° C. and a working pressure of 2.97 bar escape. After heating to 500° C. by indirect heat exchange with product gas A of temperature T=580° C., the propane cycle gas is used as the motive jet to operate the jet pump, with which the dehydrogenation cycle gas and the propane cycle gas are fed to the charging of reaction zone A with reaction gas A starting mixture.

The propane cycle gas has the following contents:
    propane 96.42% by volume and
    propylene 2.58% by volume.

VI. First Comparative Example of a Process for Preparing Acrylic Acid from Propane (a Steady Operating State is Described)

Reaction zone A consists of an adiabatic shaft furnace reactor with only one fixed catalyst bed whose configuration corresponds to the first fixed bed tray in flow direction in the tray reactor from II.

The heterogeneously catalyzed partial propane dehydrogenation is carried out in the shaft reactor in straight pass with dehydrogenation cycle gas mode. The loading of the total amount of catalyst (calculated without inert material) with propane is 1500 l (STP)/l·h.

24.87 m³ (STP)/h of reaction gas A charge gas mixture (starting mixture; T=450° C.; P=2.82 bar) are fed to the shaft furnace reactor and have the following contents:
propane 22.3% by volume,
propylene 3.65% by volume,
ethane 0.07% by volume,
methane 0.17% by volume,
$H_2$ 4.18% by volume,
$O_2$ 2.09% by volume,
$N_2$ 60.32% by volume,
$H_2O$ 5.05% by volume,
CO 0% by volume, and
$CO_2$ 1.17% by volume.

Reaction gas A charge gas mixture is a mixture of a first (1.69 m³ (STP)/h) and a second (23.18 m³ (STP)/h) gas mixture which is obtained by combining the two gas mixtures by means of a static mixer.

The first gas mixture is a mixture of 0.013 m³ (STP)/h of steam (T=134° C.; P=3 bar), 1.06 m³ (STP)/h of crude propane which comprises propane (fresh propane) to an extent of >98% by volume (T=122° C.; P=3.50 bar) and 0.62 m³ (STP)/h of molecular hydrogen (purity >99% by volume; T=35° C.; P=2.20 bar), and the second gas mixture is a mixture of 11.41 m³ (STP)/h of dehydrogenation cycle gas (T=534° C.; P=2.36 bar), 11.16 m³ (STP)/h of compressed residual gas cycle gas (T=444° C.; P=2.82 bar) and 0.61 m³ (STP)/h of compressed air (T=175° C., P=3.00 bar).

Indirect heat exchange with product gas A conducted out of reaction zone A and in the direction of reaction zone B establishes the temperature of the compressed residual gas cycle gas of 444° C.

The dehydrogenation cycle gas flow is effected by the jet pump principle (cf. DE-A 102 112 75), the compressed residual gas cycle gas set to 444° C. functioning as the motive jet. The compressed air is metered (throttled) into the resulting mixture.

The bed height of the fixed catalyst bed flowed through by the reaction gas A charge gas mixture is adjusted such that product gas A leaves this catalyst bed with a temperature of 534° C. and a pressure of 2.36 bar with the following contents:
propane 17.83% by volume,
propylene 7.51% by volume,
ethane 0.15% by volume,
methane 0.37% by volume,
$H_2$ 3.76% by volume,
$O_2$ 0% by volume,
$N_2$ 59.18% by volume,
$H_2O$ 9.06% by volume,
CO 0% by volume, and
$CO_2$ 1.14% by volume.

The leaving amount is 25.35 m³ (STP)/h.

A flow divider divides product gas A at the outlet of the shaft reactor into two portions of identical composition.

The first portion is 11.41 m³ (STP)/h and the second portion is 13.94 m³ (STP)/h. The first portion is recycled into reaction zone A as a constituent of the reaction gas A charge gas mixture. For the purpose of dehydrogenation cycle gas flow of the first portion, a jet pump is operated with the compressed residual gas cycle gas heated as described as the motive jet, the conveying direction of the motive jet decompressed through a motive nozzle via a mixing zone and a diffuser pointing in the direction of the entrance into reaction zone A, and the suction nozzle pointing in the direction of the first flow portion of product gas A, and the "suction nozzle—mixing zone—diffuser" connection forming the sole connecting line between the first portion of product gas A to be recycled and the access to reaction zone A.

The second portion of product gas A is conducted out of reaction zone A and cooled to 317° C. in an indirect heat exchanger disposed downstream of it by indirect heat exchange with compressed residual gas cycle gas (11.16 m³ (STP)/h; T=131° C.; P=3.00 bar) (the working pressure is essentially retained). This heats the residual gas cycle gas to 444° C. and reduces its working pressure to 2.82 bar.

Subsequently, product gas A is cooled to 221° C. in a second indirect heat exchange with "propane-scrubbed" product gas A (9.06 m³ (STP)/h; T=30° C., P=10.50 bar), which is simultaneously accompanied by a reduction in its working pressure to 2.18 bar.

This heats the "propane-scrubbed" product gas A (also referred to hereinafter as "offgas") to 287° C. and changes its working pressure to 10.10 bar. Subsequently, the offgas is decompressed from 10.10 bar to 3.50 bar in the first expansion stage of a multistage expansion turbine, and cooled at the same time from 287° C. to 176° C. The offgas leaving the first expansion stage is then conducted in indirect heat exchange to the product gas A at 221° C. The latter essentially retains its working pressure and is cooled at the same time to 215° C. This heats the offgas to 191° C. with substantial retention of its working pressure. The offgas is then decompressed to 1.23 bar in the second expansion stage of the multistage expansion turbine, which cools it to 89° C. The offgas is then fed to residue incineration.

Product gas A at 215° C. and 2.18 bar is subsequently cooled first to 60° C. in an air-cooled indirect heat exchanger and then to 39° C. in a cooling water-cooled indirect heat exchanger. By means of droplet separators, the water which condenses out in the course of the coolings is removed (0.68 kg/h).

The remaining 13.09 m³ (STP)/h of product gas A are compressed to 4.78 bar in the first compressor stage of a multistage radial compressor. This heats product gas A from 39° C. to 106° C. Subsequently, product gas A is cooled to 54° C. by means of air in an indirect heat exchanger and the water which condenses out (8.0 g/h) is removed by means of droplet separators. In a second compression stage, the remaining 13.08 m³ (STP)/h of product gas A are compressed to 10.50 bar. This is associated with heating of product gas A to 123° C. Cooling with air in an indirect heat exchanger then cools product gas A first to 54° C. and then indirect heat exchange with cooling water cools it to 29° C. By means of droplet separators, the water which condenses out in the course of the coolings is removed (0.29 kg/h). The 12.71 m³ (STP)/h of product gas A which now still remain (whose working pressure is essentially still 10.50 bar) are conducted into the lower portion of a column with random packing. Their contents are:
propane 19.55% by volume,
propylene 8.24% by volume,
ethane 0.16% by volume,
methane 0.41% by volume,
$H_2$ 4.13% by volume,
$O_2$ 0% by volume,
$N_2$ 64.9% by volume,
$H_2O$ 0.38% by volume,
CO 0% by volume, and
$CO_2$ 1.25% by volume.

At the top of the propane scrubbing column, 120.32 kg/h of technical tetradecane from Haltermann, Germany (as described in II.) are introduced with an introduction temperature of 30° C. (P=10.50 bar).

At the top of the scrubbing column, "propane-scrubbed" product gas A (offgas) escapes, which, at a pressure of 10.50 bar and a temperature of 30° C. and an amount of 9.06 m$^3$ (STP)/h, has the following contents:
propane 0.02% by volume,
propylene 0.01% by volume,
ethane 0.14% by volume,
methane 0.56% by volume,
$H_2$ 5.79% by volume,
$O_2$ 0% by volume,
$N_2$ 91.0% by volume,
$H_2O$ 0.40% by volume,
CO 0% by volume, and
$CO_2$ 1.07% by volume.

After indirect heat exchange as already described with product gas A conducted out of reaction zone A and multistage decompression to 1.23 bar in a multistage expansion turbine, the offgas is fed to residue incineration or incinerated in a flare. Before the offgas is decompressed, it may be appropriate on the industrial scale to remove the molecular hydrogen present therein. This can be effected, for example, by subjecting the offgas to a membrane separation as already described. The molecular hydrogen thus removed can be recycled fully or partly into reaction zone A (appropriately as a constituent of the reaction gas A charge gas mixture). Alternatively, it can, for example, be combusted in fuel cells.

127.37 kg/h of absorbate which have a pressure of 10.5 bar and a temperature of 40° C. are withdrawn from the bottom of the "propane scrubbing column which is neither cooled nor heated externally. It comprises 3.83% by weight of propane, 1.54% by weight of propylene, 0.1% by weight of ethane and 0.1% by weight of $CO_2$. Before the absorbate is conducted to the top of the downstream desorption column, it is decompressed to a pressure of 2.01 bar (for example in an inverse pump or by means of a valve; the mechanical energy released in the case of the inverse pump is appropriately also used to recompress absorbent freed of propane in the desorption column (the liquid effluent of the desorption column)). The biphasic mixture obtained is conducted into the desorption column at the top thereof.

8.00 m$^3$ (STP)/h of air compressed to a pressure of 3.00 bar (which heats it to 175° C.) are conducted into the desorption column (likewise a column with random packing) as stripping gas from the bottom in countercurrent to the absorbate descending from the top of the desorption column.

The liquid effluent of the desorption column (120.32 kg/h) is compressed back to 10.50 bar by means of a pump and, after indirect cooling with cooling water, recycled at a temperature of 30° C. to the propane absorption at the top of the propane scrubbing column (absorption column).

At the top of the desorption column, 11.64 m$^3$ (STP)/h of gas mixture escape at a temperature of 33° C. and a pressure of 2.01 bar, and the following contents:
propane 21.33% by volume,
propylene 8.99% by volume,
ethane 0.07% by volume,
$O_2$ 13.93% by volume,
$N_2$ 52.6% by volume,
$H_2O$ 1.53% by volume,
CO 0% by volume, and
$CO_2$ 0.55% by volume.

Indirect heat exchange with steam increases the temperature of the gas mixture to 140° C. (this reduces the working pressure to 1.91 bar).

This gas mixture is used as reaction gas B starting mixture (charge gas mixture) to charge a reaction zone B which has the same structure as that from II.

The propylene loading of the catalyst charge of the first oxidation stage is selected to be 130 l (STP)/h. The salt melts (53% by weight of $KNO_3$, 40% by weight of $NaNO_2$, 7% by weight of $NaNO_3$) have the following entrance temperatures:
$T_A$=329° C. $T_B$=330° C.
$T_C$=265° C. $T_D$=266° C.

Reaction gas B leaves the intermediate cooler in an amount of 11.66 m$^3$ (STP)/h with a temperature of 260° C., a pressure of 1.68 bar and the following contents:
acrolein 7.51% by volume,
acrylic acid 0.51% by volume,
propane 21.3% by volume,
propylene 0.53% by volume,
ethane 0.07% by volume,
$O_2$ 3.92% by volume,
$N_2$ 52.52% by volume,
$H_2O$ 10.81% by volume,
CO 0.38% by volume, and
$CO_2$ 1.43% by volume.

2.17 m$^3$ (STP)/h of air compressed to 3 bar in a radial compressor (which heats it to 175° C.) are metered (throttled) into it, so that the entrance temperature of the reaction gas into the second oxidation stage is 252° C. at an entrance pressure of 1.68 bar (acrolein loading=110 l (STP)/l·h).

The product gas mixture of the second oxidation stage (product gas B) has a temperature of 270° C. and a pressure of 1.55 bar and the following contents:
acrolein 0.03% by volume,
acrylic acid 6.62% by volume,
acetic acid 0.2% by volume,
propane 18.51% by volume,
propylene 0.46% by volume,
ethane 0.06% by volume,
$O_2$ 2.95% by volume,
$N_2$ 58.0% by volume,
$H_2O$ 10.0% by volume,
CO 0.52% by volume, and
$CO_2$ 1.64% by volume.

Product gas B (13.42 m$^3$ (STP)/h) is fractionally condensed in a tray column as described in WO 2004/035514.

13.8 g/h of high boilers (polyacrylic acids (Michael adducts) etc.) are fed to residue incineration.

From the second collecting tray above the feed of product gas B into the tray column, 2.82 kg/h of condensed crude acrylic acid are withdrawn, which have a temperature of 15° C. and 96.99% by weight of acrylic acid. After addition of a small amount of water, this is suspension-crystallized as described in WO 2004/035514, the suspension crystals are separated from the mother liquor in hydraulic scrubbing columns and the mother liquor is recycled into the condensation column as described in WO 2004/035514. The purity of the washed suspension crystals is >99.87% by weight of acrylic acid and is suitable immediately for the preparation of water-"superabsorbing" polymers for use in the hygiene sector.

The amount of acid water condensate which is withdrawn from the third collecting tray above the feed of product gas B into the condensation column and is not recycled into the condensation column is 1.04 kg/h and has a temperature of 33° C. It is likewise fed to residue incineration.

At the top of the condensation column, 11.16 m³ (STP)/h of residual gas leave the condensation column with a temperature of 33° C. and a pressure of 1.20 bar and the following contents:
propane 22.06% by volume,
propylene 0.46% by volume,
$O_2$ 3.54% by volume,
$N_2$ 69.75% by volume,
$H_2O$ 1.76% by volume,
CO 0% by volume, and
$CO_2$ 1.43% by volume.

The residual gas in its entirety is compressed to 3 bar (this heats it to 131° C.) and, as described, after indirect heat exchange with product gas A conducted out of reaction zone A, recycled into reaction zone A as residual gas cycle gas (as the motive jet for the jet pump used for dehydrogenation cycle gas flow).

VII. Second Comparative Example of a Process for Preparing Acrylic Acid from Propane (a Steady Operating State is Described)

Reaction zone A consists of an adiabatic shaft furnace reactor with only one fixed catalyst bed whose configuration corresponds to the first fixed bed tray in flow direction in the tray reactor from II.

The heterogeneously catalyzed partial propane dehydrogenation is carried out in the shaft reactor in straight pass with dehydrogenation cycle gas mode. The loading of the total amount of catalyst (calculated without inert material) with propane is 1500 l (STP)/l·h.

23.79 m³ (STP)/h of reaction gas A charge gas mixture (starting mixture; T=456° C.; P=2.82 bar) are fed to the shaft furnace reactor and have the following contents:
propane 19.31% by volume,
propylene 3.82% by volume,
ethane 0.11% by volume,
methane 0.33% by volume,
$H_2$ 4.27% by volume,
$O_2$ 2.14% by volume,
$N_2$ 62.72% by volume,
$H_2O$ 5.11% by volume,
CO 0% by volume, and
$CO_2$ 1.22% by volume.

Reaction gas A charge gas mixture is a mixture of a first (1.69 m³ (STP)/h) and a second (22.10 m³ (STP)/h) gas mixture which is obtained by combining the two gas mixtures by means of a static mixer.

The first gas mixture is a mixture of 0.013 m³ (STP)/h of steam (T=134° C.; P=3 bar), 1.08 m³ (STP)/h of crude propane which comprises propane (fresh propane) to an extent of >98% by volume (T=122° C.; P=3.50 bar) and 0.60 m³ (STP)/h of molecular hydrogen (purity >99% by volume; T=35° C.; P=2.20 bar), and the second gas mixture is a mixture of 10.93 m³ (STP)/h of dehydrogenation cycle gas (T=546° C.; P=2.82 bar), 10.52 m³ (STP)/h of compressed residual gas cycle gas (P=3 bar; T=455° C.) and 0.65 m³ (STP)/h of compressed air (T=175° C., P=3.00 bar).

Indirect heat exchange with product gas A conducted out of reaction zone A and in the direction of reaction zone B establishes the temperature of the compressed residual gas cycle gas of 455° C.

The dehydrogenation cycle gas flow is effected by the jet pump principle (cf. DE-A 102 112 75), the compressed residual gas cycle gas set to 455° C. functioning as the motive jet. The compressed air is metered (throttled) into the resulting mixture.

The bed height of the fixed catalyst bed flowed through by the reaction gas A charge gas mixture is such that product gas A leaves this catalyst bed with a temperature of 546° C. and a pressure of 2.39 bar with the following contents:
propane 14.60% by volume,
propylene 7.84% by volume,
ethane 0.24% by volume,
methane 0.70% by volume,
$H_2$ 3.79% by volume,
$O_2$ 0% by volume,
$N_2$ 61.44% by volume,
$H_2O$ 9.19% by volume,
CO 0% by volume, and
$CO_2$ 1.19% by volume.

The leaving amount is 24.29 m³ (STP)/h.

A flow divider divides product gas A at the outlet of the shaft reactor into two portions of identical composition.

The first portion is 10.93 m³ (STP)/h and the second portion is 13.36 m³ (STP)/h. The first portion is recycled into reaction zone A as a constituent of the reaction gas A charge gas mixture. For the purpose of dehydrogenation cycle gas flow of the first portion, a jet pump is operated with the compressed residual gas cycle gas heated as described as the motive jet, the conveying direction of the motive jet decompressed through a motive nozzle via a mixing zone and a diffuser pointing in the direction of the entrance into reaction zone A, and the suction nozzle pointing in the direction of the first flow portion of product gas A, and the "suction nozzle—mixing zone—diffuser" connection forming the sole connecting line between the first portion of product gas A to be recycled and the access to reaction zone A.

The second portion of product gas A is conducted out of reaction zone A and cooled to 330° C. in an indirect heat exchanger disposed downstream of it by indirect heat exchange with compressed residual gas cycle gas (10.52 m³ (STP)/h; T=135° C.; P=3.00 bar) (the working pressure is essentially retained). This heats the residual gas cycle gas to 455° C. and reduces its working pressure to 2.82 bar.

Subsequently, product gas A is cooled to 220° C. in a second indirect heat exchange with "propane-scrubbed" product gas A (9.06 m³ (STP)/h; T=30° C., P=10.50 bar), which is simultaneously accompanied by a reduction in its working pressure to 2.21 bar.

This heats the "propane-scrubbed" product gas A (also referred to hereinafter as "offgas") to 300° C. and changes its working pressure to 10.10 bar. Subsequently, the offgas is decompressed from 10.10 bar to 3.50 bar in the first expansion stage of a multistage expansion turbine, and cooled at the same time from 300° C. to 187° C. The offgas leaving the first expansion stage is then conducted in indirect heat exchange to the product gas A at 220° C. The latter essentially retains its working pressure and is cooled at the same time to 219° C. This heats the offgas to 190° C. with substantial retention of its working pressure. The offgas is then decompressed to 1.23 bar in the second expansion stage of the multistage expansion turbine, which cools it to 88° C. The offgas is then fed to residue incineration.

Product gas A at 219° C. and 2.21 bar is subsequently cooled first to 60° C. in an air-cooled indirect heat exchanger and then to 39° C. in a cooling water-cooled indirect heat exchanger. By means of droplet separators, the water which condenses out in the course of the coolings is removed (0.68 kg/h).

The remaining 12.52 m³ (STP)/h of product gas A are compressed to 4.81 bar in the first compressor stage of a multistage radial compressor. This heats product gas A from 39° C. to 108° C. Subsequently, product gas A is cooled to 54°

C. by means of air in an indirect heat exchanger and the water which condenses out (5.7 g/h) is removed by means of droplet separators. In a second compression stage, the remaining 12.51 m³ (STP)/h of product gas A are compressed to 10.50 bar. This is associated with heating of product gas A to 126° C. Cooling with air in an indirect heat exchanger then cools product gas A first to 54° C. and then indirect heat exchange with cooling water cools it to 29° C. By means of droplet separators, the water which condenses out in the course of the coolings is removed (0.28 kg/h). The 12.17 m³ (STP)/h of product gas A which now still remain (whose working pressure is essentially still 10.50 bar) are conducted into the lower portion of a column with random packing. Their contents are:

propane 16.0% by volume,
propylene 8.60% by volume,
ethane 0.26% by volume,
methane 0.77% by volume,
$H_2$ 4.17% by volume,
$O_2$ 0% by volume,
$N_2$ 67.48% by volume,
$H_2O$ 0.39% by volume,
CO 0% by volume, and
$CO_2$ 1.31% by volume.

At the top of the propane scrubbing column, 115.96 kg/h of technical tetradecane from Haltermann, Germany (as described in II.) are introduced with an introduction temperature of 30° C. (P=10.50 bar).

At the top of the scrubbing column, "propane-scrubbed" product gas A (offgas) escapes, which, at a pressure of 10.50 bar and a temperature of 30° C. and an amount of 9.06 m³ (STP)/h, has the following contents:

propane 0.02% by volume,
propylene 0.01% by volume,
ethane 0.22% by volume,
methane 1.04% by volume,
$H_2$ 5.59% by volume,
$O_2$ 0% by volume,
$N_2$ 90.60% by volume,
$H_2O$ 0.39% by volume,
CO 0% by volume, and
$CO_2$ 1.12% by volume.

After indirect heat exchange as already described with product gas A conducted out of reaction zone A and multistage decompression to 1.23 bar in a multistage expansion turbine, the offgas is fed to residue incineration. Before the offgas is decompressed, it may be appropriate on the industrial scale to remove the molecular hydrogen present therein. This can be effected, for example, by subjecting the offgas to a membrane separation as already described. The molecular hydrogen thus removed can be recycled fully or partly into reaction zone A (appropriately as a constituent of the reaction gas A charge gas mixture). Alternatively, it can, for example, be combusted in fuel cells.

121.93 kg/h of absorbate which have a pressure of 10.5 bar and a temperature of 40° C. are withdrawn from the bottom of the "propane scrubbing column" which is neither cooled nor heated externally. It comprises 3.14% by weight of propane, 1.61% by weight of propylene, 0.01% by weight of ethane and 0.09% by weight of $CO_2$. Before the absorbate is conducted to the top of the downstream desorption column, it is decompressed to a pressure of 1.98 bar (for example in an inverse pump or by means of a valve; the mechanical energy released in the case of the inverse pump is appropriately also used to recompress absorbent freed of propane in the desorption column (the liquid effluent of the desorption column)). The biphasic mixture obtained is conducted into the desorption column at the top thereof.

7.88 m³ (STP)/h of air compressed to a pressure of 3.00 bar (which heats it to 175° C.) are conducted into the desorption column (likewise a column with random packing) as stripping gas from the bottom in countercurrent to the absorbate descending from the top of the desorption column.

The liquid effluent of the desorption column (115.94 kg/h) is compressed back to 10.50 bar by means of a pump and, after indirect cooling with cooling water, recycled at a temperature of 30° C. to the propane absorption at the top of the propane scrubbing column (absorption column).

At the top of the desorption column, 10.97 m³ (STP)/h of gas mixture escape at a temperature of 33° C. and a pressure of 1.98 bar, and the following contents:

propane 17.77% by volume,
propylene 9.53% by volume,
ethane 0.11% by volume,
$O_2$ 14.54% by volume,
$N_2$ 54.91% by volume,
$H_2O$ 1.59% by volume,
CO 0% by volume, and
$CO_2$ 0.55% by volume.

Indirect heat exchange with steam increases the temperature of the gas mixture to 140° C. (this reduces the working pressure to 1.88 bar).

This gas mixture is used as reaction gas B starting mixture (charge gas mixture) to charge a reaction zone B which has the same structure as that from II.

The propylene loading of the catalyst charge of the first oxidation stage is selected to be 130 l (STP)/h. The salt melts (53% by weight of $KNO_3$, 40% by weight of $NaNO_2$, 7% by weight of $NaNO_3$) have the following entrance temperatures:

$T_A$=32300 $T_B$=327° C.
$T_C$=262° C. $T_D$=265° C.

Reaction gas B leaves the intermediate cooler in an amount of 10.99 m³ (STP)/h with a temperature of 260° C., a pressure of 1.67 bar and the following contents:

acrolein 7.98% by volume,
acrylic acid 0.53% by volume,
propane 17.74% by volume,
propylene 0.56% by volume,
ethane 0.1% by volume,
$O_2$ 3.92% by volume,
$N_2$ 54.82% by volume,
$H_2O$ 11.44% by volume,
CO 0.41% by volume, and
$CO_2$ 1.49% by volume.

2.21 m³ (STP)/h of air compressed to 3 bar in a radial compressor (which heats it to 175° C.) are metered (throttled) into it, so that the entrance temperature of the reaction gas into the second oxidation stage is 251° C. at an entrance pressure of 1.67 bar (acrolein loading=110 l (STP)/l·h).

The product gas mixture of the second oxidation stage (product gas B) has a temperature of 270° C. and a pressure of 1.55 bar and the following contents:

acrolein 0.03% by volume,
acrylic acid 6.94% by volume,
acetic acid 0.21% by volume,
propane 15.25% by volume,
propylene 0.48% by volume,
ethane 0.09% by volume,
$O_2$ 2.95% by volume,
$N_2$ 60.31% by volume,
$H_2O$ 10.49% by volume,
CO 0.55% by volume, and
$CO_2$ 1.69% by volume.

Product gas B (12.79 m³ (STP)/h) is fractionally condensed in a tray column as described in WO 2004/035514.

13.8 g/h of high boilers (polyacrylic acids (Michael adducts) etc.) are fed to residue incineration.

From the second collecting tray above the feed of product gas B into the tray column, 2.82 kg/h of condensed crude acrylic acid are withdrawn, which have a temperature of 15° C. and 96.99% by weight of acrylic acid. After addition of a small amount of water, this is suspension-crystallized as described in WO 2004/035514, the suspension crystals are separated from the mother liquor in hydraulic scrubbing columns and the mother liquor is recycled into the condensation column as described in WO 2004/035514. The purity of the washed suspension crystals is >99.87% by weight of acrylic acid and is suitable immediately for the preparation of water-"superabsorbing" polymers for use in the hygiene sector.

The amount of acid water condensate which is withdrawn from the third collecting tray above the feed of product gas B into the condensation column and is not recycled into the condensation column is 1.06 kg/h and has a temperature of 33° C. It is likewise fed to residue incineration.

At the top of the condensation column, 10.52 m$^3$ (STP)/h of residual gas leave the condensation column with a temperature of 33° C. and a pressure of 1.20 bar and the following contents:

propane 18.36% by volume,
propylene 0.49% by volume,
$O_2$ 3.58% by volume,
$N_2$ 73.32% by volume,
$H_2O$ 1.73% by volume,
CO 0% by volume, and
$CO_2$ 1.51% by volume.

The residual gas in its entirety is compressed to 3 bar (this heats it to 135° C.) and, as described, after indirect heat exchange with product gas A conducted out of reaction zone A, recycled into reaction zone A as residual gas cycle gas (as the motive jet for the jet pump used for dehydrogenation cycle gas flow).

U.S. Provisional Patent Application No. 60/802,786, filed on May 24, 2006, is incorporated into the present application by literature reference.

With regard to the abovementioned teachings, numerous changes and deviations from the present invention are possible. It can therefore be assumed that the invention, within the scope of the appended claims, can be performed differently from the way described specifically herein.

What is claimed is:

1. A process for preparing acrolein or acrylic acid or a mixture thereof from propane, in which
    A) at least two gaseous propane-comprising feed streams, of which at least one comprises fresh propane, are fed to a first reaction zone A to form a reaction gas A;
    in reaction zone A, reaction gas A is conducted through at least one catalyst bed in which partial heterogeneously catalyzed dehydrogenation of the propane forms molecular hydrogen and propylene;
    without separating off said molecular hydrogen, molecular oxygen is fed to reaction zone A and, in reaction zone A, oxidizes at least a portion of molecular hydrogen present in reaction gas A to steam, and product gas A which comprises propylene, propane and steam is withdrawn from reaction zone A;
    B) in a first separation zone I, steam present in product gas A is optionally removed by condensation partly or fully by indirect and/or direct cooling of product gas A to leave a product gas A*;
    C) in a reaction zone B, product gas A or product gas A* is used, with feeding of molecular oxygen, to charge at least one oxidation reactor with a reaction gas B comprising propane, propylene and molecular oxygen, and the propylene present therein is subjected to a heterogeneously catalyzed partial gas phase oxidation to give a product gas B comprising acrolein or acrylic acid or a mixture thereof as the target product, and also unconverted propane;
    D) product gas B is conducted out of reaction zone B and, in a second separation zone II, target product present therein is removed to leave a propane-comprising residual gas;
    E) a portion of residual gas having the composition of the residual gas is optionally recycled as a propane-comprising feed stream into reaction zone A;
    F) in a separation zone III, propane present in residual gas which has not been recycled into reaction zone A and from which any steam present therein optionally has been removed beforehand partly or fully by condensation and/or any molecular hydrogen present therein optionally has been removed beforehand partly or fully by means of a separating membrane is absorbed into an organic solvent by absorption from the residual gas to form a propane-comprising absorbate; and
    G) in a separation zone IV, the propane is removed from the absorbate and recycled into reaction zone A as a propane-comprising feed stream;
    which comprises
    oxidizing at least sufficient molecular hydrogen to steam in reaction zone A that the amount of hydrogen oxidized to steam in reaction zone A is at least 20 mol % of the amount of molecular hydrogen formed in reaction zone A.

2. The process according to claim 1, wherein at least some of the heat energy generated by the oxidation of molecular hydrogen in reaction zone A is used to heat gaseous feed streams fed to reaction zone A by indirect heat exchange with reaction gas A or product gas A or reaction gas A and product gas A as heat carriers.

3. The process according to claim 1 or 2, wherein the amount of hydrogen oxidized to steam in reaction zone A is at least 30 mol % of the amount of molecular hydrogen formed in reaction zone A.

4. The process according to claim 1 or 2, wherein the amount of hydrogen oxidized to steam in reaction zone A is at least 40 mol % of the amount of molecular hydrogen formed in reaction zone A.

5. The process according to claim 1 or 2, wherein the amount of hydrogen oxidized to steam in reaction zone A is from 20 to 90 mol % of the amount of molecular hydrogen formed in reaction zone A.

6. The process according to claim 1 or 2, wherein the amount of hydrogen oxidized to steam in reaction zone A is from 30 to 70 mol % of the amount of molecular hydrogen formed in reaction zone A.

7. The process according to claim 1 or 2, wherein reaction gas B comprises molecular hydrogen.

8. The process according to claim 1 or 2, wherein reaction gas B does not comprise any molecular hydrogen.

9. The process according to claim 1 or 2, wherein the product gas A withdrawn from reaction zone A is used as such to charge the at least one oxidation reactor in reaction zone B.

10. The process according to claim 1 or 2, wherein at least 5 mol % of the steam present in product gas B is removed by condensation in separation zone I.

11. The process according to claim 1 or 2, wherein at least 25 mol % of the steam present in product gas B is removed by condensation in separation zone I.

12. The process according to claim 1 or 2, wherein at least 50 mol % of the steam present in product gas B is removed by condensation in separation zone I.

13. The process according to claim 1 or 2, wherein from 5 to 98 mol % of the steam present in product gas B is removed by condensation in separation zone I.

14. The process according to claim 1 or 2, wherein the working pressure in reaction zone A is from >1 to 5 bar.

15. The process according to claim 1 or 2, wherein the following relationships apply to the working pressures P in the different zones of the process, determined in each case at the entrance into the particular zone:

$$P_{reaction\ zone\ A} > P_{separation\ zone\ I} >$$
$$P_{reaction\ zone\ B} > P_{separation\ zone\ II} <$$
$$P_{separation\ zone\ III} > P_{separation\ zone\ IV} >$$
$$P_{reaction\ zone\ A}.$$

16. The process according to claim 1 or 2, wherein molecular hydrogen is combusted with molecular oxygen in reaction zone A not later than when 90 mol % of the total amount of molecular hydrogen formed in reaction zone A has been formed.

17. The process according to claim 1 or 2, wherein molecular hydrogen is combusted with molecular oxygen in reaction zone A not later than when 75 mol % of the total amount of molecular hydrogen formed in reaction zone A has been formed.

18. The process according to claim 1 or 2, wherein molecular hydrogen is combusted with molecular oxygen in reaction zone A not later than when 65 mol % of the total amount of molecular hydrogen formed in reaction zone A has been formed.

19. The process according to claim 1 or 2, wherein steam present in product gas A in a separation zone I is removed at least partly and this removal is brought about by indirect and direct cooling of product gas A.

20. The process according to claim 1 or 2, wherein a portion of residual gas having the composition of the residual gas is recycled as a propane-comprising feed stream into reaction zone A, and the residual gas comprises molecular oxygen.

21. The process according to claim 1 or 2, wherein the molecular oxygen fed to reaction zone A is also fed as a constituent of air.

22. The process according to claim 1 or 2, wherein the molecular oxygen fed to reaction zone A is also fed as a constituent of a gas which comprises not more than 50% by volume of constituents other than molecular oxygen.

23. The process according to claim 1 or 2, wherein the removal of the propane from the absorbate in separation zone IV is performed by stripping with a steam-comprising gas and the propane-laden stripping gas is recycled as a propane-comprising feed stream into reaction zone A.

24. The process according to claim 1 or 2, wherein reaction zone A is configured adiabatically.

25. The process according to claim 1 or 2, wherein, based on a single pass through reaction zone A, from 10 to 40 mol % of the total amount of propane fed to reaction zone A is converted with dehydrogenation in reaction zone A.

26. The process according to claim 1 or 2, wherein reaction zone A comprises at least one tray reactor.

27. The process according to claim 1 or 2, wherein the reaction gas A which forms in reaction zone A has the following contents:
from 50 to 80% by volume of propane,
from 0.1 to 20% by volume of propylene,
from 0 to 10% by volume of $H_2$,
from 0 to 20% by volume of $N_2$, and
from 5 to 15% by volume of $H_2O$.

28. The process according to claim 1 or 2, wherein the reaction gas A which forms in reaction zone A has the following contents:
from 55 to 80% by volume of propane,
from 0.1 to 20% by volume of propylene,
from 2 to 10% by volume of $H_2$,
from 1 to 5% by volume of $O_2$,
from 0 to 20% by volume of $N_2$, and
from 5 to 15% by volume of $H_2O$.

29. The process according to claim 1 or 2, wherein the product gas A withdrawn from reaction zone A has the following contents:
from 30 to 50% by volume of propane,
from 15 to 30% by volume of propylene,
from 0 to 10% by volume of $H_2$,
from 10 to 25% by volume of $H_2O$,
from 0 to 1% by volume of $O_2$, and
from 0 to 35% by volume of $N_2$.

30. The process according to claim 1 or 2, wherein product gas A is cooled by indirect heat exchange with the propane-comprising feed stream which has been removed in separation zone IV and recycled into reaction zone A.

31. The process according to claim 1 or 2, wherein the heterogeneously catalyzed partial gas phase oxidation is a two-stage partial oxidation of propylene to acrylic acid.

32. The process according to claim 31, wherein the reaction gas fed to the second oxidation stage has the following contents:
from 3 to 25% by volume of acrolein,
from 5 to 65% by volume of molecular oxygen,
from 6 to 70% by volume of propane,
from 0 to 20% by volume of $H_2$,
from 8 to 65% by volume of $H_2O$, and
from 0 to 70% by volume of $N_2$.

33. The process according to claim 1 or 2, wherein the residual gas has the following contents:
from 1 to 20% by volume of $H_2O$,
from 0 to 80% by volume of $N_2$,
from 10 to 90% by volume of propane,
from 0 to 20% by volume of $H_2$,
from 0 to 10% by volume of $O_2$,
from 1 to 20% by volume of $CO_2$, and
from $\geq 0$ to 5% by volume of CO.

34. The process according to claim 1 or 2, wherein the propane-comprising feed stream which has been removed in separation zone IV and recycled into reaction zone A has the following contents:
from 80 to 99.99 mol % of propane,
from 0 to 5 mol % of propylene, and
from 0 to 20 mol % of $H_2O$.

35. The process according to claim 1 or 2, wherein a portion of residual gas having the composition of the residual gas is recycled as a propane-comprising feed stream into reaction zone A, and this portion of residual gas, based on the total amount of residual gas, is up to 10% by weight.

36. The process according to claim 1 or 2, wherein the molecular oxygen fed to reaction zone B is also fed as a constituent of a gas which does not comprise more than 50% by volume of constituents other than molecular oxygen.

37. The process according to claim 1 or 2, wherein the molecular oxygen fed to reaction zone B is also fed as a constituent of air.

* * * * *